(12) United States Patent
Roberts et al.

(10) Patent No.: US 7,498,480 B2
(45) Date of Patent: Mar. 3, 2009

(54) CYTOPLASMIC GENE INHIBITION OR GENE EXPRESSION IN TRANSFECTED PLANTS BY A TOBRAVIRAL VECTOR

(75) Inventors: Peter D. Roberts, Benicia, CA (US); Monto H. Kumagai, Kailiua, HI (US); Andrew A. Vaewhongs, Vacaville, CA (US)

(73) Assignee: Novici Biotech LLC, Vacaville, CA (US)

( * ) Notice: Subject to any disclaimer, the term of this patent is extended or adjusted under 35 U.S.C. 154(b) by 742 days.

(21) Appl. No.: 10/634,221

(22) Filed: Aug. 4, 2003

(65) Prior Publication Data

US 2004/0088757 A1     May 6, 2004

Related U.S. Application Data

(60) Division of application No. 09/771,035, filed on Jan. 25, 2001, now Pat. No. 6,700,040, which is a continuation-in-part of application No. PCT/US00/20261, filed on Jul. 21, 2000, which is a continuation-in-part of application No. 09/232,170, filed on Jan. 15, 1999, now abandoned, which is a continuation-in-part of application No. 09/008,186, filed on Jan. 16, 1998, now abandoned.

(51) Int. Cl.
*C12N 15/83* (2006.01)
*C12N 5/04* (2006.01)
*C12N 15/82* (2006.01)

(52) U.S. Cl. .................. 800/278; 435/320.1; 435/69.1; 800/285; 800/286; 800/298

(58) Field of Classification Search ........................ None
See application file for complete search history.

(56) References Cited

U.S. PATENT DOCUMENTS 5,922,602 A    7/1999   Kumagai et al.

6,369,296 B1    4/2002   Ratcliff et al.

FOREIGN PATENT DOCUMENTS

WO     WO 98/36083     8/1998
WO     WO 99/50429     10/1999

OTHER PUBLICATIONS

McFarlane, S.A., J. Gen. Virol., 1999, 80:2799-2807.*
McFarlane, S.A., J. Gen. Virol., 1999, vol. 80, pp. 2799-2807.*
Ratcliff et al., Plant J., 2001, vol. 25, pp. 237-245.*
Sablowski et al. (1995) Proc Natl. Sci. USA 92:6901-6905.
Baulcombe (1999) Current Opinion in Plant Biology 2:109-113.
MacFarlane et al. (2000) Virology 267(1):29-35.
Ratcliff et al. (1999) Plant Cell 11:1207-1215.
Baulcombe (1996) Plant Molecular Biology 32:79-88.
Marathe et al. (2000) Plant Molecular Biology 43(2-3):295-306.

* cited by examiner

*Primary Examiner*—Elizabeth F. McElwain
*Assistant Examiner*—Li Zheng
(74) *Attorney, Agent, or Firm*—Wayne P. Fitzmaurice

(57) ABSTRACT

This invention is directed to a monopartite RNA viral vector comprising modified tobravirus RNA-1 comprising an inserted foreign RNA sequence. This invention is also directed to a bipartite RNA viral vector derived from a tobravirus, wherein the vector comprises one or more foreign RNA sequences. The invention is directed to a method of silencing one or more endogenous plant host genes and a method of simultaneously silencing a plant host gene and expressing a foreign gene in a plant host. Such methods comprise infecting a plant host with a bipartite vector comprising modified tobravirus RNA-1 and RNA-2. The invention is further directed to a method of compiling a plant functional gene profile, a method of changing the phenotype or biochemistry of a plant host, and a method of determining the presence of a trait in a plant host, using a monopartite or bipartite viral vector derived from a tobravirus.

17 Claims, 35 Drawing Sheets

Tobacco Rattle Virus Silencing Vector

RNA-1: LSB-1

RNA-2: PpK20

```
ATAAAACATTTCAATCCTTTGAACGCGGTAGAACGTGCTAATTGGATTTTGGTGAGAA
CGCGGTAGAACGTACTTATCACCTACAGTTTTATTTTGTTTTTCTTTTTGGTTTAATCTA
TCCAGCTTAGTACCGAGTGGGGGAAAGTGACTGGTGTGCCTAAAACCTTTTCTTTGAT
ACTTTGTAAAAATACATACAGATACAATGGCGAACGGTAACTTCAAGTTGTCTCAATT
GCTCAATGTGGACGAGATGTCTGCTGAGCAGAGGAGTCATTTCTTTGACTTGATGCTG
ACTAAACCTGATTGTGAGATCGGGCAAATGATGCAAAGAGTTGTTGTTGATAAAGTCG
ATGACATGATTAGAGAAAGAAAGACTAAAGATCCAGTGATTGTTCATGAAGTTCTTTC
TCAGAAGGAACAGAACAAGTTGATGGAAATTTATCCTGAATTCAATATCGTGTTTAAA
GACGACAAAAACATGGTTCATGGGTTTGCGGCTGCTGAGCGAAAACTACAAGCTTTAT
TGCTTTTAGATAGAGTTCCTGCTCTGCAAGAGGTGGATGACATCGGTGGTCAATGGTC
GTTTTGGGTAACTAGAGGTGAGAAAAGGATTCATTCCTGTTGTCCAAATCTAGATATT
CGGGATGATCAGAGAGAAATTTCTCGACAGATATTTCTTACTGCTATTGGTGATCAAG
CTAGAAGTGGTAAGAGACAGATGTCGGAGAATGAGCTGTGGATGTATGACCAATTTC
GTGAAAATATTGCTGCGCCTAACGCGGTTAGGTGCAATAATACATATCAGGGTTGTAC
ATGTAGGGGTTTTTCTGATGGTAAGAAGAAAGGCGCGCAGTATGCGATAGCTCTTCAC
AGCCTGTATGACTTCAAGTTGAAAGACTTGATGGCTACTATGGTTGAGAAGAAAACTA
AAGTGGTTCATGCTGCTATGCTTTTTGCTCCTGAAAGTATGTTAGTGGACGAAGGTCC
ATTACCTTCTGTTGACGGTTACTACATGAAGAAGAACGGGAAGATCTATTTCGGTTTT
GAGAAAGATCCTTCCTTTTCTTACATTCATGACTGGGAAGAGTACAAGAAGTATCTAC
TGGGGAAGCCAGTGAGTTACCAAGGGGATGTGTTCTACTTCGAACCGTGGCAGGTGA
GAGGAGACACAATGCTTTTTTCGATCTACAGGATAGCTGGAGTTCCGAGGAGGTCTCT
ATCATCGCAAGAGTACTACCGAAGAATATATATCAGTAGATGGGAAAACATGGTTGT
TGTCCCAATTTTCGATCTGGTCGAATCAACGCGAGAGTTGGTCAAGAAAGACCTGTTT
GTAGAGAAACAATTCATGGACAAGTGTTTGGATTACATAGCTAGGTTATCTGACCAGC
AGCTGACCATAAGCAATGTTAAATCATACTTGAGTTCAAATAATTGGGTCTTATTCAT
AAACGGGGCGGCCGTGAAGAACAAGCAAAGTGTAGATTCTCGAGATTTACAGTTGTT
GGCTCAAACTTTGCTAGTGAAGGAACAAGTGGCGAGACCTGTCATGAGGGAGTTGCG
TGAAGCAATTCTGACTGAGACGAAACCTATCACGTCATTGACTGATGTGCTGGGTTTA
ATATCAAGAAAACTGTGGAAGCAGTTTGCTAACAAGATCGCAGTCGGCGGATTCGTT
GGCATGGTTGGTACTCTAATTGGATTCTATCCAAAGAAGGTACTAACCTGGGCGAAGG
ACACACCAAATGGTCCAGAACTATGTTACGAGAACTCGCACAAAACCAAGGTGATAG
TATTTCTGAGTGTTGTGTATGCCATTGGAGGAATCACGCTTATGCGTCGAGACATCCG
AGATGGACTGGTGAAAAAACTATGTGATATGTTTGATATCAAACGGGGGGCCCATGT
CTTAGACGTTGAGAATCCGTGCCGCTATTATGAAATCAACGATTTCTTTAGCAGTCTGT
```

FIG. 3A

ATTCGGCATCTGAGTCCGGTGAGACCGTTTTACCAGATTTATCCGAGGTAAAAGCCAA
GTCTGATAAGCTATTGCAGCAGAAGAAAGAAATCGCTGACGAGTTTCTAAGTGCAAA
ATTCTCTAACTATTCTGGCAGTTCGGTGAGAACTTCTCCACCATCGGTGGTCGGTTCAT
CTCGAAGCGGACTGGGTCTGTTGTTGGAAGACAGTAACGTGCTGACCCAAGCTAGAG
TTGGAGTTTCAAGAAAGGTAGACGATGAGGAGATCATGGAGCAGTTTCTGAGTGGTC
TTATTGACACTGAAGCAGAAATTGACGAGGTTGTTTCAGCCTTTTCAGCTGAATGTGA
AGAGGGGAAACAAGCGGTACAAAGGTGTTGTGTAAACCTTTAACGCCACCAGGATT
TGAGAACGTGTTGCCAGCTGTCAAACCTTTGGTCAGCAAAGGAAAAACGGTCAAACG
TGTCGATTACTTCCAAGTGATGGGAGGTGAGAGATTACCAAAAAGGCCGGTTGTCAGT
GGAGACGATTCTGTGGACGCTAGAAGAGAGTTTCTGTACTACTTAGATGCGGAGAGA
GTCGCTCAAAATGATGAAATTATGTCTCTGTATCGTGACTATTCGAGAGGAGTTATTC
GAACTGGAGGTCAGAATTACCCGCACGGACTGGGAGTGTGGGATGTGGAGATGAAGA
ACTGGTGCATACGTCCAGTGGTCACTGAACATGCTTATGTGTTCCAACCAGACAAACG
TATGGATGATTGGTCGGGATACTTAGAAGTGGCTGTTTGGGAACGAGGTATGTTGGTC
AACGACTTCGCGGTCGAAAGGATGAGTGATTATGTCATAGTTTGCGATCAGACGTATC
TTTGCAATAACAGGTTGATCTTGGACAATTTAAGTGCCCTGGATCTAGGACCAGTTAA
CTGTTCTTTTGAATTAGTTGACGGTGTACCTGGTTGTGGTAAGTCGACAATGATTGTCA
ACTCAGCTAATCCTTGTGTCGATGTGGTTCTCTCTACTGGGAGAGCAGCAACCGACGA
CTTGATCGAGAGATTCGCGAGCAAAGGTTTTCCATGCAAATTGAAAAGGAGAGTGAA
GACGGTTGATTCTTTTTTGATGCATTGTGTCGATGGTTCTTTAACCGGAGACGTGTTGC
ATTTCGACGAAGCTCTCATGGCCCATGCTGGTATGGTGTACTTTTGCGCTCAGATAGCT
GGTGCTAAACGATGTATCTGTCAAGGAGATCAGAATCAAATTTCTTTCAAGCCTAGGG
TATCTCAAGTTGATTTGAGGTTTTCTAGTCTGGTCGGAAAGTTTGACATTGTTACAGAA
AAAAGAGAAACTTACAGAAGTCCAGCAGATGTGGCTGCCGTATTGAACAAGTACTAT
ACTGGAGATGTCAGAACACATAACGCGACTGCTAATTCGATGACGGTGAGGAAGATT
GTGTCTAAAGAACAGGTTTCTTTGAAGCCCGGTGCTCAGTACATAACTTTCCTTCAGTC
TGAGAAGAAGGAGTTGGTAAATTTGTTGGCATTGAGGAAAGTGGCAGCTAAAGTGAG
TACAGTACACGAGTCGCAAGGAGAGACATTCAAAGATGTAGTCCTAGTCAGGACGAA
ACCTACGGATGACTCAATCGCTAGAGGTCGGGAGTACTTAATCGTGGCGTTGTCGCGT
CACACACAATCACTTGTGTATGAAACTGTGAAGAGGACGATGTAAGCAAAGAGATC
AGGGAAAGTGCCGCGCTTACGAAGGCGGCTTTGGCAAGATTTTTTGTTACTGAGACCG
TCTTATGACGGTTTCGGTCTAGGTTTGATGTCTTTAGACATCATGAAGGGCCTTGCGCC
GTTCCAGATTCAGGTACGATTACGGACTTGGAGATGTGGTACGACGCTTTGTTTCCGG
GAAATTCGTTAAGAGACTCAAGCCTAGACGGGTATTTGGTGGCAACGACTGATTGCA

FIG. 3B

ATTTGCGATTAGACAATGTTACGATCAAAAGTGGAAACTGGAAAGACAAGTTTGCTG
AAAAAGAAACGTTTCTGAAACCGGTTATTCGTACTGCTATGCCTGACAAAAGGAAGA
CTACTCAGTTGGAGAGTTTGTTAGCATTGCAGAAAAGGAACCAAGCGGCACCCGATCT
ACAAGAAAATGTGCACGCGACAGTTCTAATCGAAGAGACGATGAAGAAGCTGAAATC
TGTTGTCTACGATGTGGGAAAAATTCGGGCTGATCCTATTGTCAATAGAGCTCAAATG
GAGAGATGGTGGAGAAATCAAAGCACAGCGGTACAGGCTAAGGTAGTAGCAGATGT
GAGAGAGTTACATGAAATAGACTATTCGTCTTACATGTATATGATCAAATCTGACGTG
AAACCTAAGACTGATTTAACACCGCAATTTGAATACTCAGCTCTACAGACTGTTGTGT
ATCACGAGAAGTTGATCAACTCGTTGTTCGGTCCAATTTTCAAAGAAATTAATGAACG
CAAGTTGGATGCTATGCAACCACATTTTGTGTTCAACACGAGAATGACATCGAGTGAT
TTAAACGATCGAGTGAAGTTCTTAAATACGGAAGCGGCTTACGACTTTGTTGAGATAG
ACATGTCTAAATTCGACAAGTCGGCAAATCGCTTCCATTTACAACTGCAGCTGGAGAT
TTACAGGTTATTTGGGCTGGATGAGTGGGCGGCCTTCCTTTGGGAGGTGTCGCACACT
CAAACTACTGTGAGAGATATTCAAAATGGTATGATGGCGCATATTTGGTACCAACAAA
AGAGTGGAGATGCTGATACTTATAATGCAAATTCAGATAGAACACTGTGTGCGCTCTT
GTCTGAATTACCATTGGAGAAAGCAGTCATGGTTACATATGGAGGAGATGACTCACTG
ATTGCGTTTCCTAGAGGAACGCAGTTTGTTGATCCGTGTCCAAAGTTGGCTACTAAGT
GGAATTTCGAGTGCAAGATTTTTAAGTACGATGTCCCAATGTTTTGTGGGAAGTTCTT
GCTTAAGACGTCATCGTGTTACGAGTTCGTGCCAGATCCGGTAAAAGTTCTGACGAAG
TTGGGGAAAAAGAGTATAAAGGATGTGCAACATTTGGCCGAGATCTACATCTCGCTG
AATGATTCCAATAGAGCTCTTGGGAACTACATGGTGGTATCCAAACTGTCCGAGTCTG
TTTCAGACCGGTATTTGTACAAAGGTGATTCTGTTCATGCGCTTTGTGCGCTATGGAAG
CATATTAAGAGTTTTACAGCTCTGTGTACATTATTCCGAGACGAAAACGATAAGGAAT
TGAACCCGGCTAAGGTTGATTGGAAGAAGGCACAGAGAGCTGTGTCAAACTTTTACG
ACTGGTAATATGGAAGACAAGTCATTGGTCACCTTGAAGAAGAAGACTTTCGAAGTCT
CAAAATTCTCAAATCTAGGGGCCATTGAATTGTTTGTGGACGGTAGGAGGAAGAGAC
CGAAGTATTTTCACAGAAGAAGAGAAACTGTCCTAAATCATGTTGGTGGGAAGAAGA
GTGAACACAAGTTAGACGTTTTTGACCAAAGGGATTACAAAATGATTAAATCTTACGC
GTTTCTAAAGATAGTAGGTGTACAACTAGTTGTAACATCACATCTACCTGCAGATACG
CCTGGGTTCATTCAAATCGATCTGTTGGATTCGAGACTTACTGAGAAAAGAAAGAGAG
GAAAGACTATTCAGAGATTCAAAGCTCGAGCTTGCGATAACTGTTCAGTTGCGCAGTA
CAAGGTTGAATACAGTATTTCCACACAGGAGAACGTACTTGATGTCTGGAAGGTGGGT
TGTATTTCTGAGGGCGTTCCGGTCTGTGACGGTACATACCCTTTCAGTATCGAAGTGTC
GCTAATATGGGTTGCTACTGATTCGACTAGGCGCCTCAATGTGGAAGAACTGAACAGT

FIG. 3C

TCGGATTACATTGAAGGCGATTTTACCGATCAAGAGGTTTTCGGTGAGTTCATGTCTTT
GAAACAAGTGGAGATGAAGACGATTGAGGCGAAGTACGATGGTCCTTACAGACCAGC
TACTACTAGACCTAAGTCATTATTGTCAAGTGAAGATGTTAAGAGAGCGTCTAATAAG
AAAAACTCGTCTTAATGCATAAAGAAATTTATTGTCAATATGACGTGTGTACTCAAGG
GTTGTGTGAATGAAGTCACTGTTCTTGGTCACGAGACGTGTAGTATCGGTCATGCTAA
CAAATTGCGAAAGCAAGTTGCTGACATGGTTGGTGTCACACGTAGGTGTGCGGAAAA
TAATTGTGGATGGTTTGTCTGTGTTGTTATCAATGATTTTACTTTTGATGTGTATAATTG
TTGTGGCCGTAGTCACCTTGAAAAGTGTCGTAAACGTGTTGAAACAAGAAATCGAGA
AATTTGGAAACAAATTCGACGAAATCAAGCTGAAAACATGTCTGCGACAGCTAAAAA
GTCTCATAATTCGAAGACCTCTAAGAAGAAATTCAAAGAGGACAGAGAATTTGGGAC
ACCAAAAAGATTTTTAAGAGATGATGTTCCTTTCGGGATTGATCGTTTGTTTGCTTTTT
GATTTTATTTTATATTGTTATCTGTTTCTGTGTATAGACTGTTTGAGATTGGCGCTTGGC
CGACTCATTGTCTTACCATAGGGGAACGGACTTTGTTTGTGTTGTTATTTTATTTGTAT
TTTATTAAAATTCTCAATGATCTGAAAAGGCCTCGAGGCTAAGAGATTATTGGGGGGT
GAGTAAGTACTTTTAAAGTGATGATGGTTACAAAGGCAAAAGGGGTAAAACCCCTCG
CCTACGTAAGCGTTATTACGCCC-3' (SEQ ID NO: X).

. tsp of PEBV coat protein sgp
ataattatactgatttgtctctcgttgatagagtctatcattctgttactaaaaatttgacaactcggtttgctgaccta ctggttactgtatcacttacccgagttaacgccCTGCAGCTCGAG  [Zeocin resistance gene] CGGCCGC
                                 *PstI*   *XhoI*                        *NotI* pK20-2b-X/N-Pme1
5828 bp 40K
22k
Xho I
Zeo R
Not I
Pme1
TRV RNA-2(+1)
pUC18

22K — 557 nt — T7 promoter

FIG. 5 tsp of PEBV coat protein sgp
ataattatactgatttgtctctcgttgatagagtctatcattctgttactaaaaatttgacaactcggtttgctgaccta Start codon of PDS
ctggttactgtatcacttacccgagttaacgccctgcag ATG CCC CAA ATT GGA CTT GTT
                                        Met pro gln ile gly leu val pK20-2b-PDS(+)
7168 bp

40 K
PDS (+)
TRV RNA-2 (+4862)
22 K
pUC18
TRV RNA-2 (+1)

22 K — 557 nt — T7 Promoter

FIG. 7

```
740 AT #120  27  TCCGAAACATTCTTCGTAGTGAAGCAAAATGGGGTTGAGTTTCGCCAAGCTGTTTAGCAG
                 ||||||||||||||||||||||||||||||||||||||||||||||||||||||||||||
AA042085         TCCGAAACATTCTTCGTAGTGAAGCAAAATGGGGTTGAGTTTCGCCAAGCTGTTTAGCAG

740 AT #120  27  GCTTTTTGCCAAGAAGGAGATGCGAATTCTGATGGTTGGTCTCTTGATGCTGCTGGTAAGAC
                 ||||||||||||||||||||||||||||||||||||||||||||||||||||||||||||
AA042085         GCTTTTTGCCAAGAAGGAGATGCGAATTCTGATGGTTGGTCTTGATGCTGCTGGTAAGAC

740 AT #120  27  CACAATCTTGTACAAGCTCAAGCTCGGAGAGATTGTCACCACCATCCCTACTATTGGTTT
                 ||||||||||||||||||||||||||||||||||||||||||||||||||||||||||||
AA042085         CACAATCTTGTACAAGCTCAAGCTCGGAGAGATTGTCACCACCATCCCTACTATTGGTTT

740 AT #120  27  CAATGTGGAAACTGTGGAATACAAGAACATTAGTTTCACCGTGTGGGATGTCGGGGGTCA
                 ||||||||||||||||||||||||||||||||||||||||||||||||||||||||||||
AA042085         CAATGTGGAAACTGTGGAATACAAGAACATTAGTTTCACCGTGTGGGATGTCGGGGGGTCA

740 AT #120  27  GGACAAGATCCGTCCCTTGTGGAGACACTACTTCCAGAACACTCAAGGTCTAATCTTTGT
                 ||||||||||||||||||||||||||||||||||||||||||||||||||||||||||||
AA042085         GGACAAGATCCGTCCCTTGTGGAGACACTACTTCCAGAACACTCAAGGTCTAATCTTTGT

740 AT #120  27  TGTTGATAGCAATGACAGAGACAGAGTTGTTGAGGCTCGAGATGAACTCCACAGGATGCT
                 ||||||||||||||||||||||||||||||||||||||||||||||||||||||||||||
AA042085         TGTTGATAGCAATGACAGAGACAGAGTTGTTGAGGCTCGAGATGAACTCCACAGGATGCT

740 AT #120  27  GAATGAGGACGAGCTGCGTGATGCTGTGTTGCTTGTGTTT
                 ||||| |||| |||||||||||||||||||||||||||||
AA042085         GNATGAGNACGAGCTGCGTGATGCTGTGTTGCTTGTGTTT
```

FIG. 14

**Nucleotide sequence alignment of 740 AT #120 to *Oryza sativa* D17760**

```
740 AT 120    27  AAATGGGGTTGAGTTTCGCCAAGCTGTTTAGCAGGCTTTTTGCCAAGAAGGAGATGCGAA   86
                    |   ||||  | ||||| ||   |||||||| ||| |||||||||  ||| ||||
D17760       166  AGATGGGGCTCACGTTCACGAAGCTGTTCAGCCGCCTCTTCGCCAAGAAGCAGATGAGGA  225

740 AT 120    87  TTCTGATGGTTTGGTCTTGATGCTGCTGGTAAGACCACAATCTTGTACAAGCTCAAGCTCG  146
                   ||| |||| | |||| || || ||  |||| |  ||||| |||  ||||||||||||||
D17760       226  TCCTCATGGTCGGTCTCGATGCGGCTCGTAAAACCACCATCCTCTACAAGCTCAAGCTCG  285

740AT 120    147  GAGAGATTGTCACCACCATCCCTACTATTGGTTTCAATGTGGAAACTGTGGAATACAAGA  206
                   | ||||| |||||||| ||||| ||||  |||||  ||||| |||||||||| ||||||
D17760       286  GCGAGATCGTCACCACTATCCCCACCATCGGTTTTAATGTCGAAACTGTTGAGTACAAGA  345

740 AT 120   207  ACATTAGTTTCACCGTGTGGGATGTCGGGGGTCAGGACAAGATCCGTCCCTTGTGGAGAC  266
                   |||| || |||||||| ||||| ||||| |||||||||||||| |||||| ||||| ||
D17760       346  ACATTAGCTTCACCGTTTGGGATGTTGGTGGTCAGGACAAGATCAGGCCCCTGTGGAGGC  405

740 AT 120   267  ACTACTTCCAGAACACTCAAGGTCTAATCTTTGTTGTTGATAGCAATGACAGAGACAGAG  326
                   |||| ||||||||| ||||||  ||| | |||| ||||||| ||||||||||||| |||
D17760       406  ACTATTTCCAGAACACCCAGGGCCTCATTTTTGTGGTTGATAGCAATGACAGAGAGCGTG  465

740 AT 120   327  TTGTTGAGGCTCGAGATGAACTCCACAGGATGCTGAATGAGGACGAGCTGCCTGATGCTG  386
                   |||||||||||| ||||||||| |||||| |||||||||||||||||||| ||||||||
D17760       466  TTGTTGAGGCCAGGGATGAGCTCCACCGGATGCTGAATGAGGAGGATGAGCTACGTGCTG  525
```

FIG. 15A

```
740 AT 120 387  TGTTGCTTGTGTTTGCCAACAAGCAAGATCTTCCAAATGCTATGAACGCTGCTGAAATCA 446
                ||| ||| ||| |||||||||||||||||||||||| ||||||||||||||||| ||||
D17760     526  TGCTGCTGGTGTTTGCAAACAAGATCTTCCTAATGCCATGAACGCTGCTGAGATCA 585

740 AT 120 447  CAGATAAGCTTGGCCCTTCACTCCCTCCGTCAGCGTCATTGGTATATCCAGAGCACACATGTG 506
                |||| |||||||| |||||||||||| ||||||| ||| ||||| ||||||||||||||||
D17760     586  CCGACAAGCTTGGTCTGCACTCCCTTGCGCCAGCGGACATCCAGTGGTACATCCAGAGCACACATGTG 645

740 AT 120 507  CCACTTCAGGTGAAGGGCTTTATGAAGGTCTGGACTGGCTCTCCAACAACATCGCTGGCA 566
                |||||||||| ||||| |||| |||||| |||||||| ||||||||||||| ||||| |
D17760     646  CTACCCTCGGTGAGGGGTTGTATGAGGGCTTGACTGGCTTGCCAACAACATTGCCAACA 705

740 AT 120 567  AGGCATGATG 576
                ||||  ||||
D17760     706  AGGCTTGAAG 715
```

FIG. 15B

```
740 AT #120   TGGTCTTGATGCTGCTGGTAAGACCACAATCTTGTACAAGCTCAAGCTCGGAGAGATTGT
              |||||||||||  ||||||||  |||||  ||  ||||||||||||||||| |||||||| ||
Nb  ARF #3    CGGTCTTGATGCAGCTGGTAAAACCACCATATTGTACAAGCTCAAGCTGGGAGAGATAGT

740 AT #120   CACCACCATCCCTACTATTGGTTTCAATGTGGAAACTGTGGAATACAAGAACATTAGTTT
              ||||| || ||||| ||||| ||||||||||| ||||| |||||||||||||||| || ||
Nb  ARF #3    TACCACTATTCCTACCATTGGATTCAATGTGGAGACTGTTGAATACAAGAACATAAGCTT

740 AT #120   CACCGTGTGGGATGTCGGGGGTCAGGACAAGATCCGTCCCTTGTGGAGACACTACTTCCA
              ||| || |||||||| || ||||||||||||||||| || ||||||||| |||||||||
Nb  ARF #3    CACGGTCTGGGATGTTGGTGGTCAGGACAAGATCCGACCATTGTGGAGGCATTACTTCCA

740 AT #120   GAACACTCAAGGTCTAATCTTTGTTGTTGATAGCAATGACAGAGACAGAGTTGTTGAGGC
              ||||| |||||| || |||||||| ||  |||||| |||| |||| |||| ||||||||||
Nb  ARF #3    AAACACACAAGGACTTATCTTTGTGGTCGATAGTAATGATCGTGATCGTGTTGTTGAGGC

740 AT #120   TCGAGATGAACTCCACAGGATGCTGAATGAGGACGAGCTGCGTGATGCTGTGTTGCTTGT
              | |||||||| || ||| |||||| |||||||| ||||| ||  || | |||||||| |||||||
Nb  ARF #3    TAGAGATGAGCTGCACCGGATGTTGAATGAGGATGAACTGAGGGATGCTGTGCTGCTTGT

740 AT #120   GTTTGCCAACAAGCAAGATCTTCCAAATGCTATGAACGCTGCTGAAATCACAGATAAGCT
              ||||||  ||||||||||||||||||||||||||||| ||||||||| || || || |||||
Nb  ARF #3    GTTTGCTAACAAGCAAGATCTTCCAAATGCTATGAATGCTGCTGAGATTACTGACAAGCT

740 AT #120   TGGCCTTCACTCCCTCCGTCAGCGTCATTGG
              ||| |||||  || ||||||||  ||||| |||
Nb  ARF #3    TGGTCTTCATTCTCTCCGTCAACGTCACTGG
```

FIG. 17

. tsp of PEBV coat protein sgp
ataattatactgatttgtctctcgttgatagagtctatcattctgttactaaaaatttgacaactcggtttgctgaccta ctggttactgtatcacttacccgagttaacgcc<u>CTGCAG</u><u>CTCGAG</u><u>GCGGCCGC</u>
                                         Pst I    Xho I   Not I pK20-2b-120-RZ
6277 bp 40K, 22K, 120, RZ, pUC18, TRV RNA-2(+1), 22K, 557 nt, T7 promoter

FIG. 18

GAAACCGGGCGAAGCAGCAGTCAGGTCACACAATTTAGCCGAGGATGTATCTCCAGTTTA
CATCAATGAGAATGGTGACAAAGTTTACACCACTAAGAAAGAGTCACCACTGGGT
TTGGCCACAGAATCCGCTCACCCAGCCCCGCTTTTCCCCGATGATAAATATTCAA
GGCAAAGAGAGTGCTTCTGAAGAAGCGATTGGTTTGCTTCCAACCCAAAAGCCACC
TCAAAGTACTAAAGTTTTGCTATTGTATTGCTTTCTACTCATGGTTATTA
TGTTTCTCTGTCGTTGTTGACGTGACTCTTGTATTGCAACTCAAATTGC
ATGGCAGCAATTCAAACCTCATATCTAATTG

FIG. 21

GCCCACGCGTCCGATGAGGCCAAGTTGACCCTTCATGGACTTGTACAGCACTACA
TTAAATTGAGTGAAAACCGAGAAAAACTAAATGATCTGCTGGACGCCTT
AAACTTCAACCAAGTTGTTATATTTGTCAAGAGTGTAAGTCGGGCAGCACAGCTG
GATAAATTACTAGTGGAGTGTAATTTCCATCTATCTGCATCCACTCTGGCATGA
CGCAGGAAGAAAGATTGACTCGCTACAAGGGTTTCAAGAGGCCACAAGAGAAT
TCTGTGTCGCAACTGATCTGGTTGGGTAGGGCATTGACATCGAAAGGGTCAACATT
GTTATTAACTATGACATGCCAGATTCTGCAGACACGTATCTTCACAGAGTGGGTC
GAGCTGGTAGGTTTGGAACTAAAGGCCTTGCCATCACATTGTGTCATCTGCATC
AGATTCTGATGTTCTAAATCAGGTTTGAAGAAGTTTGAAGTAGACATAAAGAG
CTTCCTGAGCCAGATATATCAAGTCATTAGCCATCTTCTACGCCATCTCGAGAGC
TTCCAGCAATATCAAGTCATTTAAAAGATGGGGAACTGCCTCCTACTATATGCTCTTGCTA
TTGTTGTTAATTTGAAGAATTGGGGGGCTCCTACTCTCTTTCCCTCCAGTTTAAGAGGAGCACCTA
GCTGCTGTACCCCTTGTTGAACTACTCTTTCCTCCCAGTTTAAGAGGAGCACCTGA
ACAAATG

FIG. 23

GGTCAAATCCAAATTAGCACCTCTCAAGTTCTACAACTCTGATATTCACAAAGCA
CCATTCATTTGCCATCTTTCGCCAGAAGTATGATCGAGTCTTAATCAAGTGAAC
AATGAACACTGGTGGTACAATCATTGGACCAAGATCGAGTCTTATCAAGTGAAT
AAATAAAGTGAAATGCAACGCATTGTATGAATCCAGTAATTATCATAATTCG
GATTCACCAATTAGTGTAAATTCTTTCTGTGGTTTGGTTTTTCATATAAATT
TTCTTGCTGTGTTGTTTGATATGACGTTTCAACTCAATCCACGCAAATCATTTCAT
T

FIG. 25

```
GGCCTTTTACTTGAACTGGGCTGTCCACTCCTTCAGAATCACCAACGTCGGCATT
CAAGACACCACCCAGATCCACACACATGTGCTACTTCCAACTTCAATGACATTA
TCCACTCTATCATTGACATGGATGCTGATGTCACAATTGAGAACTCACGGTC
CGATGAGAAGCTCCTCAGTTTTCAGGGAGGAGTTAAGTATGGTGCTGGAATT
GGCCCCGGTGTCTATGATATCCACTCCCCTAGAATACCATCAACGGAAGAGATTG
CTGACAGAGTTAACAAGATGCTTGCTGTGTTCTTGACACCAACATCTTGTGGTCAA
CCCAGATTGTGGTCTCAAGACTCGCAAGTACGCTGAGGTAAAGCCAGCCCTCGAG
AACATGGTTTCTGCTGCCAAGGCCATCCGCACCCAACTTGCCAGCACCAAGTGAG
TCAGATGAAGGAGTCGCGACATATCAAGATTCCCTTTTCATGAAACAGAAAATT
CTATGTTGATTTTAATCATTGTGTTGGCAACAAATATTGTGTAGGTTAGCT
CTGCCCGCTGGGCATTTCTTCTTGTGTTTGAGCCATTCCTTTCGGAAGAAAA
TATATCCAATGTATTATGATGTTTTATGGGTCGATTTTGGTTAC
```

FIG. 27

GGATGTGTTGATCAATGGGGAAAAGAGAGCTGCTGAGGACGAGGAGATGGTCCTGAT
GGCAAGAAAATTCGCCCTGGAATATCAAACTCTGTCATTGAGACTCTTACGGAAT
GTAATGCTGCTCTTTCACACGCAAAGATATACCCAACTGAATAGTTATCCTCTCACAAA
CTCTGTGGATGCTCTGGAAAGATATACCCAACTGAATAGTTATCCTCTCACAAA
ACCAACAAACCTGGTATTTGTCTTTGGATATTCATTATCCTAAGGACTTAATTG
CTACTGGTGGTGTTGATTCAAATGCTGTGGTCTTTGATCGTCCTTCAGGACAAAT
GAGGGTGAACTAGTGGTCTCTGGCTCAGCAGATAAGACAGTTCGTTTGTGGCAAA
GTTCTGAAAATGGGAACTATGACTGTAGGCATGTCTTGAAAGATCATACAGCAGA
GGTGCAAGCTGTCACTGTCCATGCCAACCAATAACTATTTTGACTGCTTCTCTT
GATAGCACACATGGTGCTTTTATGATCTTGCTTATGCCTTATGCCTTGCACAGGTGG
CAGATGCTACAGAATCTGAGGGTTACACATCCGCAAGCTTTCCCACCCCTGATTGG
TCTTGATCCTTGGGAACAGGGACCCTCAGGGTCTCTGGTTCTGGTTCAGATTTGGGATTGT
AAAAAGTCCAGG

FIG. 29

GCTCCCAGCCCTAAGTTTGAGTACACTCCTTGGTTAATTGTCGGA
TNGGAAATCCCGGTAACAAGTATCATGGGACTCGCCACAATGTTGGTTTTGAAA
TGATTGATCGAGTTTCTCAAGAGGAGGAATCGTATTAAACACAATACAGTCAAA
GGCTTTGATAGGAATAGGTTCGATAGGGGAGGTACCCTGTGGTATTGGCAAGCCT
CAAGCCTACATGAATTTCAGTGCTGCGGAGAATCGGTCGGACCACTTGCTGCATATTATC
AGGTGCCTCTGCGTCACATCCTCCTTTGGTTTATGATGAGCTTACCAAATGG
TGTTCTGAGGCTTCAGCCTAAAGGAGGACATGGCCAGCATAATGGGGTGAAAAGT
GTGATGGAGCATTTGGATTGTCGCAGGGAATTCCCGATTTGCATAGGCATAG
GAAATCCACCTGGAACTATGGACATGAAGGCATATCTTCTACAGAAATTCAGTGA
TACAGAGCGGAAGCAGGTGGATGCAGCACTTAATCAAGGAGTTGATGCTGTCAGG
ACGGTAGTATTGGAAGGCTTTGGTAGTAAAATTTCACGATTAATATAGGACAGA
AATACAAGTATCACAAAGTTTGATGAATCTAAAATGAAGGTGTAAAGA
GCACGAAGATTTACTGATAACTTCAAGTCTAAAATTAAGGGTGTAAAAGACCC
CAAGG

FIG. 31

CYTOPLASMIC GENE INHIBITION OR GENE EXPRESSION IN TRANSFECTED PLANTS BY A TOBRAVIRAL VECTOR

This application is a Division of U.S. application Ser. No. 09/771,035, filed Jan. 25, 2001, now Pat. No. 6,700,040, which is a Continuation-in-Part of PCT/US00/20261, filed Jul. 21, 2000; which is a Continuation-in-Part of U.S. application Ser. No. 09/232,170, filed on Jan. 15, 1999 now abandoned; which is a Continuation-in-Part of U.S. application Ser. No. 09/008,186, filed on Jan. 16, 1998 now abandoned; All the above applications are incorporated herein by reference.

FIELD OF THE INVENTION

The present invention relates generally to the field of molecular biology and genetics. Specifically, the present invention relates to a method for transiently expressing a foreign gene in the cytoplasm of a plant host using a tobravirus vector.

BACKGROUND OF THE INVENTION

Great interest exists in launching genome projects in human and non-human genome project. The human genome has between 2.8 million and 3.5 million base pairs, about 3 percent of which are made of genes. In June 2000, the Human Genome Project and biotech company Celera Genomics announced that a rough draft of the human genome has been completed see National Center for Biotechnology Information (NCBI) database website). This information, however, will only represent a reference sequence of the human genome. The remaining task lies in the determination of sequence functions, which are important for the study, diagnosis, and treatment of human diseases.

The Mouse genome is also being sequenced. Genbank provides about 1.2% of the 3-billion-base mouse genome see Mouse Genome Informatics (MGI) database website) and a rough draft of the mouse genome is expected to be available by 2003 and a finished genome by 2005. In addition, the Drosophilia Genome Project has recently been completely sequenced-(see Berkeley Drosophila Genome Project database website).

Valuable and basic agricultural plants, including corn, soybeans and rice are also targets for genome projects because the information obtained thereby may prove very beneficial for increasing world food production and improving the quality and value of agricultural products. The United States Congress is considering launching a corn genome project. By helping to unravel the genetics hidden in the corn genome, the project could aid in understanding and combating common diseases of grain crops. It could also provide a big boost for efforts to engineer plants to improve grain yields and resist drought, pests, salt, and other extreme environmental conditions. Such advances are critical for a world population expected to double by 2050. Currently, there are four species which provide 60% of all human food: wheat, rice, corn, and potatoes, and the strategies for increasing the productivity of these plants is dependent on rapid discovery of the presence of a trait in these plants, and the function of unknown gene sequences in these plants.

One strategy that has been proposed to assist in such efforts is to create a database of expressed sequence tags (ESTs) that can be used to identify expressed genes. Accumulation and analysis of expressed sequence tags (ESTs) have become an important component of genome research. EST data may he used to identify gene products and thereby accelerate gene cloning. Various sequence databases have been established in an effort to store and relate the tremendous amount of sequence information being generated by the ongoing sequencing efforts. Some have suggested sequencing 500,000 ESTs for corn and 100,000 ESTs each for rice, wheat, oats, barley, and sorghum. Efforts at sequencing the genomes of plant species will undoubtedly rely upon these computer databases to share the sequence data as it is generated. *Arabidopsis thaliana* may be an attractive target discovery of a trait and for gene function discovery because a very large set of ESTs have already been produced in this organism, and these sequences tag more than 50% of the expected *Arabidopsis genes*.

Potential use of the sequence information so generated is enormous if gene function can be determined. It may become possible to engineer commercial seeds for agricultural use to convey any number of desirable traits to food and fiber crops and thereby increase agricultural production and the world food supply. Research and development of commercial seeds has so far focused primarily on traditional plant breeding, however there has been increased interest in biotechnology as it relates to plant characteristics. Knowledge of the genomes involved and the function of genes contained therein for both monocotyledonous and dicotyledonous plants is essential to realize positive effects from such technology.

The impact of genomic research in seeds is potentially far reaching. For example, gene profiling in cotton can lead to an understanding of the types of genes being expressed primarily in fiber cells. The genes or promoters derived from these genes may be important in genetic engineering of cotton fiber for increased strength or for "built-in" fiber color. In plant breeding, gene profiling coupled to physiological trait analysis can lead to the identification of predictive markers that will be increasingly important in marker assisted breeding programs. Mining the DNA sequence of a particular crop for genes important for yield, quality, health, appearance, color, taste, etc., are applications of obvious importance for crop improvement.

Work has been conducted in the area of developing suitable vectors for expressing foreign DNA and RNA in plant and animal hosts. Ahlquist (U.S. Pat. Nos. 4,885,248 and 5,173,410) describes preliminary work done in devising transfer vectors which might be useful in transferring foreign genetic material into a plant host for the purpose of expression therein. Additional aspects of hybrid RNA viruses and RNA transformation vectors are described by Ahlquist et al. in U.S. Pat. Nos. 5,466,788, 5,602,242, 5,627,060 and 5,500,360. Donson et al., U.S. Pat. Nos. 5,316,931, 5,589,367 and 5,866,785 demonstrate for the first time plant viral vectors suitable for the systemic expression of foreign genetic material in plants. Donson et al. describe plant viral vectors having heterologous subgenomic promoters for the systemic expression of foreign genes. Carrington et al., U.S. Pat. No. 5,491,076, describe particular potyvirus vectors also useful for expressing foreign genes in plants. The expression vectors described by Carrington et al. are characterized by utilizing the unique ability of viral polyprotein proteases to cleave heterologous proteins from viral polyproteins. These include Potyviruses such as Tobacco Etch Virus. Additional suitable vectors are described in U.S. Pat. Nos. 5,811,653 and 5,977,438. Condreay, et al., (*Proc. Natl. Acad. Sci. USA* 96:127-132) disclose using baculoviruses to deliver and express gene efficiently in cells types of human, primate and rodent origin. Price et al., (*Proc. Natl. Acad. Sci. USA* 93:9465-9570 (1996)) disclose infecting insect, plant and mammalian cells with Nodaviruses.

Construction of plant RNA viruses for the introduction and expression of non-viral foreign genes in plants has also been demonstrated by Brisson et al., *Methods in Enzymology* 118: 659 (1986), Guzman et al., Communications in Molecular Biology: Viral Vectors, Cold Spring Harbor Laboratory, pp. 172-189 (1988), Dawson et al., *Virology* 172:285-292 (1989), Takamatsu et al., *EMBO J.* 6:307-311 (1987), French et al., *Science* 231:1294-1297(1986), and Takamatsu et al., *FEBS Letters* 269:73-76(1990). However, these viral vectors have not been shown capable of systemic spread in the plant and expression of the non-viral foreign genes in the majority of plant cells in the whole plant. Moreover, many of these viral vectors have not proven stable for the maintenance of non-viral foreign genes. However, the viral vectors described by Donson et al., in U.S. Pat. Nos. 5,316,931, 5,589,367, and 5,866,785, Turpen in U.S. Pat. Nos. 5,811,653 and 5,977,438, Carrington, et al. in U.S. Pat. No. 5,491,076, have proven capable of infecting plant cells with foreign genetic material and systemically spreading in the plant and expressing the non-viral foreign genes contained therein in plant cells locally or systemically. Morsy et al., (*Proc. Natl. Acad. Sci. USA,* 95:7866-7871 (1998)) develop a helper-dependent adenoviral vectors having up to 37 Kb insert capacity and being easily propagated.

With the recent advent of technology for cloning, genes can be selectively turned off. One method is to create antisense RNA or DNA molecules that bind specifically with a targeted gene's RNA message, thereby interrupting the precise molecular mechanism that expresses a gene as a protein. The antisense technology which deactivates specific genes provides a different approach from a classical genetics approach. Classical genetics usually studies the random mutations of all genes in an organism and selects the mutations responsible for specific characteristics. Antisense approach starts with a cloned gene of interest and manipulates it to elicit information about its function.

The expression of virus-derived positive sense or antisense RNA in transgenic plants provides an enhanced or reduced expression of an endogenous gene. In most cases, introduction and subsequent expression of a transgene will increase (with a positive sense RNA) or decrease (with an antisense RNA) the steady-state level of a specific gene product (*Curr. Opin. Cell Biol.* 7: 399-405 (1995)). There is also evidence that inhibition of endogenous genes occurs in transgenic plants containing sense RNA (Van der Krol et al., *Plant Cell* 2(4):291-299 (1990), Napoli et al., *Plant Cell* 2:279-289 (1990) and Fray et al., *Plant Mol. Biol.* 22:589-602 (1993)).

Post-transcriptional gene silencing (PTGS) in transgenic plants is the manifestation of a mechanism that suppresses RNA accumulation in a sequence-specific manner. There are three models to account for the mechanism of PTGS: direct transcription of an antisense RNA from the transgene, an antisense RNA produced in response to over expression of the transgene, or an antisense RNA produced in response to the production of an aberrant sense RNA product of the transgene (Baulcombe, *Plant Mol. Biol.* 32:79-88 (1996)). The post-transcriptional gene silencing mechanism is typified by the highly specific degradation of either the transgene mRNA or the target RNA, by RNA having either the same or complementary nucleotide sequences. In cases that the silencing transgene is the same sense as the target endogenous gene or viral genomic RNA, it has been suggested that a plant-encoded RNA-dependent RNA polymerase makes a complementary strand from the transgene mRNA and that the small cRNAs potentiate the degradation of the target RNA. Antisense RNA and the hypothetical cRNAs have been proposed to act by hybridizing with the target RNA to either make the hybrid a substrate for double-stranded (ds) RNases or arrest the translation of the target RNA (Baulcombe, *Plant Mol. Biol.* 32: 79-88 (1996)). It is also proposed that this down-regulation or "co-suppression" by the sense RNA might be due to the production of antisense RNA by readthrough transcription from distal promoters located on the opposite strand of the chromosomal DNA (Grierson et al., *Trends Biotechnol.* 9:122-123 (1993)).

Kumagai, et al. (*Proc. Natl. Acad. Sci.* USA 92:1679 (1995)) report that gene expression in transfected *Nicotiana benthamiana* was cytoplasmic inhibited by viral delivery of a RNA of a known sequence derived from cDNA encoding tomato phytoene desaturase in a positive sense or an antisense orientation. The plant host, *Nicotiana benthamiana*, and the donor plant, tomato (*Lycopersicon esculentum*), belong to the same family. There is also evidence that inhibition of endogenous genes occurs in transgenic plants containing sense RNA (Van der Krol et al., *Plant Cell* 2(4):291-299 (1990), Napoli et al., *Plant Cell* 2:279-289 (1990) and Fray et al., *Plant Mol. Biol.* 22:589-602 (1993)).

U.S. Pat. No. 5,922,602 (Kumagai, et al.) discloses a silencing vector comprising dual subgenomic promoters. Kumagai, et al. teach a genetic vector comprising: (a) a first viral subgenomic promoter operably joined to a first nucleic acid sequence that codes for a plant viral coat protein wherein the transcription of the first nucleic acid sequence is regulated by the first plant viral subgenomic promoter; (b) a second plant viral subgenomic promoter operably joined to a second nucleic acid sequence which codes for an anti-sense RNA or a co-suppressor RNA specific for a gene of interest in a plant wherein transcription of the second nucleic acid sequence is regulated by the second plant viral subgenomic promoter; and (c) an origin of replication that initiates replication of the genetic vector in the cytoplasm of a plant cell.

WO 99/36516 (BIOSOURCE TECHNOLOGIES, INC.) discloses a method of determining the function of nucleic acid sequences, changing the phenotypic or biochemical characteristics, and silencing endogenous genes by transfecting a plant host with a recombinant viral nucleic acid comprising a foreign nucleic acid sequence. The recombinant viral nucleic acid is derived from a monopartite plus sense single-stranded RNA virus.

MacFarlane and Popovich (Virology 267:29-35 (2000)) constructed viral vectors from infectious cDNA clones of each of the three tobraviruses, tobacco rattle virus (TRV), pea early-browning virus (PEBV), and pepper ringspot virus (PepRSV). RNA2 of each of the three viruses was modified to carry an additional coat protein subgenomic promoter and was used to express green fluorescent protein (GFP). The TRV-GFP construct was prepared by removal of 3' part of the 2b gene and the entire 2c gene. The PEBV-GFP construct was prepared by removal of 2b and 2c genes. The PepRSV-GFP was prepared by removal of 3' part of the 2b gene and the entire 2c gene. The modified RNA2 constructs that MacFarlane and Popovich teach do not have the entire 2b gene.

The present invention provides a method for either silencing an endogenous gene of a plant host or expressing a foreign gene in a plant host using a monopartite or a bipartite plant viral vector derived from a tobravirus.

SUMMARY OF THE INVENTION

This invention is directed to a bipartite RNA viral vector comprising: (a) modified tobravirus RNA-1 comprising an inserted foreign RNA sequence that codes for all or part of a protein; the inserted sequence is operably linked to the 3' end of the stop codon of the RNA sequence that codes for a 16 k Da cysteine-rich protein of RNA-1; and (b) tobravirus RNA-2. The tobravirus RNA-2 may comprise a promoter-gene construct inserted in place of the 2C gene, wherein the promoter-gene construct comprises a second foreign RNA sequence.

The invention is also directed to a monopartite RNA viral vector comprising: modified tobravirus RNA-1 comprising an inserted foreign RNA sequence; the inserted sequence is operably linked to the 3' end of the stop codon of the RNA sequence which codes for a 16 k Da cysteine-rich protein of RNA-1. The foreign RNA is either in a positive sense or an anti-sense orientation, and is either a complete open reading frame or a partial open reading frame.

The invention is directed to a method of simultaneously silencing one or more endogenous host genes and a method of simultaneously silencing a plant host gene and expressing a foreign gene. Such method comprises infecting a plant host with a bipartite vector comprising tobravirus RNA-1 and RNA-2, wherein the RNA-1 comprises a first foreign RNA sequence that codes for all or part of a first protein, and the RNA-2 comprises a second foreign RNA sequence that codes for all or part of a second protein.

The invention is further directed to a method of compiling a plant functional gene profile, a method of changing the phenotype or biochemistry of a plant host, and a method of determining the presence of a trait in a plant host. Such methods comprise the steps of preparing a library of DNA or RNA sequences from a donor plant, and constructing recombinant viral nucleic acids comprising an unidentified nucleic acid insert obtained from said library, wherein said recombinant viral nucleic acids are obtained from a tobravirus.

BRIEF DESCRIPTION OF THE FIGURES

FIGS. 3A-3D lists the DNA sequence of the TRV RNA-1 clone pLSB-1 (SEQ ID NO: 1).

FIG. 5 depicts the plasmid pK20-2b-.X/N-PmeI. This plasmid contains the T7 promoter, the TRV RNA-2 22-, 40-kDa ORFs, the Pea Early Browning Virus (PEBV) subgenomic promoter, followed by the XhoI and NotI restriction sites, a PmeI site for linearizing the plasmid prior to transcription, and part of the pUC18 plasmid. The transcriptional start point (tsp) of the subgenomic RNA from the PEBV coat promoter is indicated with a period (.). (SEQ ID NO: 3).

FIG. 7 depicts the plasmids pK20-2b-PDS(+)-SmaI. This plasmid contains the T7 promoter, the TRV RNA-2 22-, 40-kDa ORFs, the Pea Early Browning Virus (PEBV) subgenomic promoter, followed by the N. benthamiana Phytoene Desaturase ORF in the sense orientation, a SmaI site for linearizing the plasmid prior to transcription, and part of the pUC18 plasmid. The transcriptional start point (tsp) of the subgenomic RNA from the PEBV coat promoter is indicated with a period (.). (SEQ ID NOS. 4 and 5).

FIG. 14 depicts the nucleotide sequence comparison of A. thaliana 740 AT #120 and A. thaliana est AA042085. (SEQ ID NOS: 9 and 10).

FIGS. 15A-15B depicts the nucleotide sequence comparison of A. thaliana 740 AT #120 and O. sativa est D17760. (SEQ ID NOS: 11 and 12).

FIG. 17 depicts the nucleotide sequence comparison of A. thaliana 740 AT #120 and N. benthamiana Nb ARF #3. (SEQ ID NOS: 13 and 14).

FIG. 18 depicts the plasmid pK20-2b-120(+)-RZ. (SEQ ID NO: 2).

FIG. 21 shows the sequence of pk20-B12 encoded protein. (SEQ ID NO. 17)

FIG. 23 shows the sequence of pK20-D11 encoded protein. (SEQ ID NO. 18).

FIG. 25 shows the sequence of pK20-F12(1) encoded protein. (SEQ ID NO. 19).

FIG. 27 shows the sequence of pK 20-B4(3) encoded protein. (SEQ ID NO. 20).

FIG. 29 shows the sequence of pK20-F12(4) encoded protein. (SEQ ID NO. 21).

FIG. 31 shows the sequence of pK20-G2(4) encoded protein. (SEQ ID NO. 22).

DETAILED DESCRIPTION OF THE INVENTION

Figure 1A:
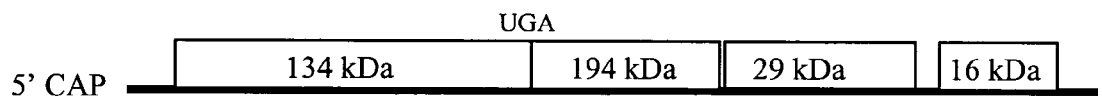
FIG. 1 depicts the tobacco rattle virus gene silencing vector. (A) TRV RNA-1 (LSB-1) contains a replicase gene which produces two proteins, a 134 kDa putative methyl transferase/nucleotide binding/helicase, and 194 kDa kDa putative RNA-dependent RNA polymerase by read-through translation of the UGA termination codon of the 134 kDa open reading frame. Downsteam is a 29 kDa movement protein (mp, 1a gene), and a 16 kDa Cysteine Rich Protein (CRP, 1b gene). (B) TRV RNA-2 encodes a 22 kDa coat protein (cp, 2a gene), a 40 kDa 2b gene required for nematode transmissibility and a 33 kDa 2c gene of unknown function.

The present invention is directed to a monopartite RNA viral vector derived from a tobravirus. The monopartite RNA viral vector comprises modified tobravirus RNA-1 that comprises an inserted foreign RNA sequence coding for all or part of a protein. The foreign RNA sequence can be inserted any place in RNA-1 as long as it does not affect the replication or infectivity of the viral vector. For example, the foreign RNA sequence can be inserted upstream (to the 5' end) or down stream (to the 3' end) of the 16 k Da cystein-rich protein. Preferably, the inserted sequence is operably linked to the 3' end of the the stop codon of the RNA sequence which codes for a 16 k Da cysteine-rich protein of RNA-1. The foreign RNA is either in a positive sense or an anti-sense orientation, and is either a complete open reading frame or a partial open reading frame. When the foreign RNA encodes for all of a protein, the RNA vector can be either an expression vector that expresses a foreign protein, or a silencing vector that inhibits the expression of an endogenous host gene. When the foreign RNA encodes a part of a protein, the RNA vector is likely to be a silencing vector, but it is also possible to be an expression vector depending on whether the construct contains an ATG codon in the correct reading frame.

The present invention is directed to a bipartite RNA viral vector comprising: (a) modified tobravirus RNA-1 comprising a first inserted foreign RNA sequence that codes for all or part of a protein; the inserted sequence is operably linked to the 3' end of the stop codon of the RNA sequence which codes for a 16 k Da cysteine-rich protein of RNA-1; and (b) tobravirus RNA-2. The presence of tobravirus RNA-2 improves the infectivity of the RNA viral vector. The presence of tobravirus RNA-2 also improves the efficiency of silencing an endogenous gene or expressing a foreign protein. The tobravirus RNA-2 optionally comprises a promoter-gene construct inserted in place of the 2C gene, wherein the promoter-gene construct comprises a second foreign RNA sequence coding for all or part of a protein. The tobravirus RNA-2 may also comprise a subgenomic promoter operably linked to the 5' end of the second foreign RNA sequence. Each of the first and second foreign RNAs is either in a positive sense or an antisense orientation, and is either a complete open reading frame or a partial open reading frame. Each of the first and second foreign RNAs either expresses a protein or inhibits the expression of an endogenous host gene. The foreign RNAs are obtained from either an eukaryotic or a prokaryotic species.

The present invention is also directed to a bipartite RNA viral vector, comprising: (a) tobravirus RNA-1; and (b) modified tobravirus RNA-2: wherein said modified tobravirus RNA-2 comprises at least one promoter-gene construct comprising a subgenomic promoter and a foreign RNA sequence, wherein said subgenomic promoter is operably linked to the 5' end of said foreign RNA sequence. and said promoter-gene construct is inserted in place of the 2c gene and without removal of the 2b gene of a tobravirus. The modified tobravirus RNA-2 may further comprise a polylinker having restriction enzyme Not I, Pst I, and XhoI sites.

The present invention is directed to a method of silencing one or more plant host genes. The method comprises the steps of infecting a plant host with the monopartite RNA viral vector or the bipartite viral vector of this invention, whereby the foreign RNA sequences cause silencing of one or more endogenous plant host genes. When the bipartite RNA vector comprises first and second foreign RNA sequences, more than one plant host genes are simultaneously silenced. The present invention provides methods that are able to silence multiple genes using two different RNAs and express more than one protein in a transfected plant. The method may further comprise a step of allowing the viral vectors to infect the plant host systemically.

The present invention is directed to a method of simultaneously silencing a plant host genes and expressing a foreign gene. The method comprises infecting a plant host with the bipartite RNA vector that comprises first and second foreign RNA sequences according to this invention, whereby the first foreign RNA sequence causes silencing of an endogenous gene of a plant host, and the second foreign RNA is expressed in the plant host, or vice versa. The method may further comprise a step of allowing the viral vectors to infect the plant host systemically.

The present invention is directed to a method of compiling a plant functional gene profile by directional cloning of a library of DNA or RNA sequences from a donor plant. The method comprises: a) preparing a library of DNA or RNA sequences from a donor plant, and constructing recombinant viral nucleic acids comprising an unidentified nucleic acid insert obtained from said library in either a positive sense or an antisense orientation, wherein said recombinant viral nucleic acids are obtained from a tobravirus; b) infecting a plant host with one or more said recombinant viral nucleic acids; c) transiently expressing said unidentified nucleic acid in the plant host; d) determining one or more phenotypic or biochemical changes in the plant host; e) identifying an associated trait relating to a phenotypic or biochemical change; f) identifying said recombinant viral nucleic acid that results in said one or more changes in the plant host; g) repeating steps b)-f) until at least one nucleic acid sequence associated with said trait is identified, whereby a functional gene profile of the plant host or of the plant donor is compiled. The DNA or RNA sequences from a donor plant can be cDNAs, genomic DNAs, a pool of RNAs or synthetic nucleic acids.

The present invention is directed to a method of compiling a plant functional gene profile by non-directional cloning of a library of DNA or RNA sequences from a donor plant. The method comprises: a) preparing a library of DNA or RNA sequences from a donor plant, and constructing recombinant viral nucleic acids comprising an unidentified nucleic acid insert obtained from said library, wherein recombinant viral nucleic acids are obtained from a tobravirus; b) infecting a plant host with one or more said recombinant viral nucleic acids; c) transiently expressing said recombinant nucleic acid in the plant host; d) determining one or more changes in a phenotypic or biochemical trait in the plant host; e) identifying said recombinant viral nucleic acid that results in said one or more changes in the plant host; f) determining the sequence of said unidentified nucleic acid insert; and g) repeating steps b)-f) until at least one nucleic acid sequence associated with said trait is identified, whereby a functional gene profile of the plant host or the plant donor is compiled.

The invention is directed to a method of changing phenotype or a biochemistry of a plant host using recombinant viral nucleic acids comprising an unidentified nucleic acid insert. The method comprises: (a) preparing a library of DNA and RNA sequences of a plant donor; (b) constructing recombinant viral nucleic acids comprising an unidentified nucleic acid insert obtained from said library, wherein said recombinant viral nucleic acids are obtained from a tobravirus; (c) infecting said plant host with one or more said recombinant viral nucleic acids, (d) expressing transiently said unidentified nucleic acid in said plant host; and (e) changing one or more phenotypic or biochemical characteristics in said plant host.

The invention is directed to a method of changing phenotype or a biochemistry of a plant host using recombinant viral nucleic acids comprising a known nucleic acid insert. The method comprises: (a) infecting a plant host with a monopartite or a bipartite viral vector comprising one or more foreign RNA sequences of this invention; (b) expressing transiently the foreign RNA sequence in said plant host; and (c) changing one or more phenotypic or biochemical characteristics in said plant host.

The present invention comprises a method of determining the presence of a trait in a plant host. The method comprises: (a) preparing a library of DNA and RNA sequences of a plant donor; (b) constructing recombinant viral nucleic acids comprising an unidentified nucleic acid insert obtained from said library in an antisense or a positive sense orientation, wherein said recombinant viral nucleic acid are obtained from a tobravirus; (c) infecting said plant host with one or more said recombinant viral nucleic acids, and expressing transiently said unidentified nucleic acid in said plant host such that one or more phenotypic or biochemical changes occurs; (d) determining one or more biochemical or phenotypic traits relating to said changes in said plant host; and (e) comparing said one or more biochemical or phenotypic traits to a plant host that is uninfected.

The present method has the advantages that the nucleic acid sequence does not need to be known, identified, isolated, or characterized prior to infecting a plant host with a recombinant viral nucleic acid comprising the nucleic acid sequence. Once changes in the plant host is observed, the nucleic acid sequence can be determined by further identifying the recombinant viral nucleic acid that results in changes in the host, and analyzing the sequence of the nucleic acid insert in the recombinant viral nucleic acid that results in changes in the host.

The present invention provides a method of infecting a plant host by a recombinant plant viral nucleic acid derived from a tobravirus which contains one or more non-native nucleic acid sequences, or by a recombinant plant virus containing a recombinant plant viral nucleic acid derived from a tobravirus. The non-native nucleic acids are subsequently transcribed or expressed in the infected plant host. The products of the non-native nucleic acid sequences result in changing phenotypic traits in the plant host, affecting biochemical pathways within the plant, or affecting endogenous gene expression within the plant.

In one embodiment, a nucleic acid is introduced into a plant host by way of a recombinant viral nucleic acid. Such recombinant viral nucleic acids are stable for the maintenance and transcription or expression of non-native nucleic acid sequences and are capable of systemically transcribing or expressing such non-native sequences in the plant host. Preferred recombinant plant viral nucleic acids useful in the present invention comprise a native plant viral subgenomic promoter, a plant viral coat protein coding sequence, and at least one non-native nucleic acid sequence.

The viral vectors used in accordance with the present invention may be encapsidated by the coat proteins encoded by the recombinant plant virus. The recombinant plant viral nucleic acid or recombinant plant virus is used to infect a plant host. The recombinant plant viral nucleic acid is capable of replication in the host, localized or systemic spread in the host, and transcription or expression of the non-native nucleic acid in the host to affect a phenotypic or biochemical change in the host.

The first step in producing recombinant plant viral nucleic acids is to modify the nucleotide sequences of the plant viral nucleotide sequence by known conventional techniques such that one or more non-native subgenomic promoters are inserted into the plant viral nucleic acid without destroying the biological function of the plant viral nucleic acid. The subgenomic promoters are capable of transcribing or expressing adjacent nucleic acid sequences in a plant host infected by the recombination plant viral nucleic acid or recombinant plant virus. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a nonnative coat protein coding sequence, under control of one of the native or non-native subgenomic promoters. The coat protein is involved in the systemic infection of the plant host.

The chimeric genes and vectors and recombinant plant viral nucleic acids used in this invention are constructed using techniques well known in the art. Suitable techniques have been described in Sambrook et al. (2nd ed.), Cold Spring Harbor Laboratory, Cold Spring Harbor (1982, 1989); *Methods in Enzymol*. (Vols. 68, 100, 101, 118, and 152-155) (1979, 1983, 1986 and 1987); and *DNA Cloning*, D. M. Clover, Ed., IRL Press, Oxford (1985). Medium compositions have been described by Miller, J., *Experiments in Molecular Genetics*, Cold Spring Harbor Laboratory, New York (1972), as well as the references previously identified, all of which are incorporated herein by reference. DNA manipulations and enzyme treatments are carried out in accordance with manufacturers' recommended procedures in making such constructs.

The present invention is not intended to be limited to any particular viral constructs, but rather to include all operable constructs. Specifically, those skilled in the art may choose to transfer DNA or RNA of any size up to and including an entire genome in a plant into a host organism in order to practice the present invention. Those skilled in the art will understand that the recited embodiments are representative only. All operable constructs useful to produce localized or systemic expression of nucleic acids in a plant are within the scope of the present invention.

Preferred plant viruses useful for this invention are bipartite viruses such as bipartite RNA viruses. However, the invention should not be construed as limited to using these particular viruses, but rather the present invention is contemplated to include all suitable viruses. For general information concerning plant viruses, see Matthews, *Plant Virology*, $3^{rd}$ Ed., Academic Press. San Diego (1991). The most preferred tobraviruses are characterized below.

Tobraviruses include tobacco rattle tobraviruses (TRV), pea early-browning viruses (PEBV) and pepper ringspot viruses. These viruses have two positive-sense, single-stranded genomic RNAs that are separated encapsidated in rod-shaped particles. RNA1 encodes the viral proteins that are responsible for replication and movement of the virus in plants. RNA1 can cause infection in plants in the complete absence of the second RNA (RNA2). RNA2 varies in size, according to virus isolate, and encodes the virus coat protein and sometimes one or more other, nonstructural proteins. (Harrison, B. D., and Robinson, D. J. Tobraviruses. In *"The Plant Viruses"* M. H. V. van Regenmortel and H. Fraenkel-Conrat, Eds., Vol. 2, pp. 339-369. Plenum Press, New York. (1986))

Tobraviruses have a number of features that make them attractive as gene expression vectors. The smaller viral RNA, RNA2, is nonessential for systemic infection of plants by the virus, which means that it can be extensively modified without affecting virus viability. The CP gene subgenomic RNA promoters of these viruses are, to an extent, interchangeable, which allows the construction of relatively stable constructs containing additional promoters. This raises the possibility that constructs might be built that can express more than one nonviral protein. Tobraviruses, particularly TRV, have a wide host range, suggesting that they could be used as gene vectors in many plant species. Lastly, in contrast to many other plant viruses, tobraviruses are adapted for efficient movement into the root system. This property makes them particularly useful as delivery vectors for testing a wide variety of proteins that may be active in plant-soil/pathogen interactions. Tobraviruses are able to replicate in Arabidopsis, a model plant that has been completely sequenced and has a wealth of genetic mutants.

Figure 1B:
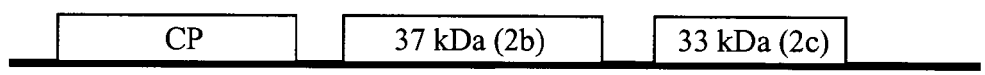

TRV is able to infect a wide range of plant hosts, including *Arabidopsis thaliana, Nicotiana* species, *Brassica campestris, Capsicum annuum, Chenopodium amaranticolor, Glycine max, Lycopersicon esculentum, Narcissus pseudonarcissus, Petunia X hybrida, Pisum sativum, Solanum tuberosum, Spinacia oleracea, Vicia faba*, see web page for The Universal Virus Database of the International Committee on Taxonomy of Viruses (ICTVdB). TRV RNA 1 (FIG. 1A) encodes proteins involved in viral replication (Replicase, 134/194 kDa) and movement (Movement Protein (MP) 29 kDa), as well as Cysteine Rich Protein (CRP, 16 kDa). TRV RNA-2a (FIG. 1B) encodes 22 kDa coat protein that encapsidates RNA-1 and RNA-2 separately into rod shaped particles. The 2b gene encodes for a 40 kDa protein that is required for nematode transmissibility. The 2c gene encodes a 33 kDa protein whose function is not known (MacFarlane, *J Gen. Virol.* 80.2799-807 (1999)). In one embodiment of the invention, the invention provides a monopartite RNA viral vector derived from a tobravirus. The monopartite RNA viral vector comprises tobravirus RNA-1 that comprises an inserted foreign RNA sequence coding for all or part of a protein. The foreign RNA sequence can be inserted any place in RNA-1 as long as the insertion does not affect the replication and infectivity of the viral vector. For example, the foreign RNA sequence can be inserted upstream or downstream of the RNA sequence encoding a 16k Da cysteine-rich protein of RNA-1. In a preferred embodiment, the inserted foreign RNA sequence is operably linked to the 3' end of the stop codon of the RNA sequence which codes for a 16k Da cysteine-rich protein of RNA- 1. Currently, there are no published reports of multipartite viruses being modified for use as a monopartite silencing system. A monopartite silencing system would be useful for high throughput genomics screening whereby thousands of hosts are inoculated with a virus containing a library of different genes. Viral induced gene silencing of the gene library would create host gene knockouts. Having one DNA template to use for transcribing infectious RNA instead of two would simplify the process of creating gene knockouts. This could make a genomics screening project using a viral vector derived from a tobravirus more economically feasible. In addition, because the 2a (coat protein) and 2b genes from RNA-2 are required for nematode transmissibility (MacFarlane, 1999), an RNA-1 only system would be safer for outdoor field trials.

In another embodiment of the invention, the invention provides a bipartite RNA viral vector derived from a tobravirus. The bipartite RNA viral vector comprising: (a) modified tobravirus RNA-1 comprising a first inserted foreign RNA sequence that codes for all or part of a protein; the inserted sequence is operably linked to the 3' end of the stop codon of the RNA sequence which codes for a 16 k Da cysteine-rich protein of RNA-1; and (b) tobravirus RNA-2. The presence of tobravirus RNA-2 improves the infectivity of the bipartite RNA vector compared with a monopartite RNA vector. The presence of tobravirus RNA-2 also improves the efficiency of silencing of a plant host gene or a gene of interest, and the efficiency of expressing a foreign protein in a plant host.

In another embodiment of the invention, the invention provides a bipartite RNA viral vector derived from a tobravirus. The bipartite RNA viral vector comprises (a) modified tobravirus RNA-1 comprising a first foreign RNA sequence, operably linked to 3'-end of the stop codon of the RNA sequence which codes for a 16 k Da cysteine-rich protein of RNA-1; and (b) modified tobravirus RNA-2 comprising a promoter-gene construct, which comprises subgenomic promoter operably linked to the 5' end of a second foreign RNA sequence, wherein said promoter-gene construct is inserted in place of the 2C gene.

The present invention provides a monopartite RNA vector or a bipartite vector derived from a tobravirus comprising a foreign RNA sequence that encodes for all or part of a protein involved in the regulation of plant growth. In one embodiment of the invention, the protein involves activating, processing or degrading RNAs. In another embodiment of the invention, the protein involves modifying DNAs. Some of such proteins are characterized below.

The small nucleolar ribonucleoprotein particles containing H/ACA-type snoRNAs (H/ACA snoRNPs) are crucial transacting factors intervening in eukaryotic ribosome biogenesis. Most of these particles generate the site-specific pseudouridylation of rRNAs while a subset are required for 18S rRNA synthesis. Nhp2p (22kDa) and Nop 10p (10 kDa) are conserved, essential and present in the dense fibrillar component of the nucleolus. Nhp2p and Nop 10p are specifically associated with all H/ACA snoRNAs and are essential to the function of H/ACA snoRNPs. Cells lacking Nhp2p or Nop 10p are impaired in global rRNA pseudouridylation and are in the A1 and A2 cleavage steps of the pre-rRNA required for the synthesis of mature 18S rRNA. (Henras, et al., *EMBO. J.* 17:7078-90 (1998)).

Structural modulation of RNA is fundamental to proper execution of a large number of intracellular processes, including mRNA maturation, ribosome assembly and translation and often involves a group of proteins, designated RNA helicases, that can unwind RNA:RNA and/or RNA:DNA duplexes. A large number of RNA helicases have been identified and grouped into three families based on their amino acid sequence, i.e., DEAD, DEA/IH and DECH box families. DEAD box proteins have been found in all the prokaryotes and eukaryotes examined thus far. They share a central core region with seven conserved motifs that are speaced similarly, while the N- and -C-terminal regions of the core differ in both sequence and length among family members. (Okanami, et al., *Nucl. Acid Res.* 26:2638-43 (1998)).

The eukaryotic translation initiation factor 4A, for example, is a member of the DEA(D/H)-box RNA helicase family. (Caruthers, et al., *Proc. Natl. Acad. Sci.*, USA 97:13080-5 (2000). Dbp5p/Rat8p is a yeast nuclear poreassociated DEAD-box protein essential for RNA export. (Snay-Hodge, et al, *EMBO. J.* 17:2663-76 (1998)). The DEAD box RNA helicase family in *Arabidopsis thaliana* have been described by Aubourg, et al. (*Nucl. Acid Res.* 27:628-36 (1991) and Okanami, et al. (*Nucl. Acid Res.* 26:2638-43 (1998)).

Telomerase is a ribonucleoprotein reverse transcriptase. The RNA subunit contains a templating sequence complementary to the G-rich strand of the telomere, whereas the telomerase reverse transcriptase (TERT) harbors the catalytic activity for telomere repeat synthesis. Telomerase is an essential enzyme that maintains telomeres on eukaryotic chromosomes. In mammals, telomerase is required for the lifelong proliferative capacity of normal regenerative and reproductive tissues and for sustained growth in a dedifferentiated state. Fitzgerald, et al. (*J. Biol Chem.* 275:15962-8 (2000)) have reported the cloning and characterization of the Arabidopsis telomerase reverse transcriptase (TERT) gene. It is known that Nop 10 interacts with telomerase.

Plants synthesize S-methylmethionine (SMM) from S-adenoslymethionine and methionine in a reaction mediated by S-methyltransferase, and use SMM as a methyl donor for methionine synthesis from homocysteine. These reactions comprise the SMM cycle. (Ranocha, et al. *Proc. Natl. Acad. Sci.* 21:15962-8 (2000)). S-methyltransferase also methylates DNA; the methylated DNA cannot be transcribed into RNA by silencing.

The present invention is directed to a method of simultaneously silencing a plant host gene and expressing a foreign gene, and a method of simultaneously silencing more than one endogenous host gene using a bipartite RNA viral vector derived from a tobravirus. The method comprises infecting a plant host with a bipartite vector comprising modified tobravirus RNA-1 and RNA-2, wherein the RNA-1 comprises a first foreign RNA sequence that codes for all or part of a first protein, and the RNA-2 comprises a second foreign RNA sequence that codes for all or part of a second protein. Being able to simultaneously silence one gene in TRV RNA-1 (or RNA-2) and overexpress or silence another gene in TRV RNA-2 (or RNA-1) provides several benefits. It expands the number of biological products that could be produced in plants. Many biological products are secondary metabolites, which may require several enzymatic steps for the plant to manufacture. A multiple gene expression and silencing viral system would be able to modify pathways to make these important products. Secondary metabolites contribute to tastes, scents and colors in food. They also serve as pharmaceuticals (e.g. morphine, vinblastine, taxol) and as defense compounds for plants. In addition, a multiple gene expression and silencing system could allow us to improve the feasibility of expressing gene products in plants by, for example, shutting down expression of endogenous proteases that destroy the desired product, or by reducing levels of endogenous contaminants that hinder purification of the desired product. This system could also redirect carbon flow to the desired products to increase their yield. Furthermore, a multiple gene expression and silencing system could allow us to suppress plant glycosylation patterns of expressed proteins to reduce the likelihood of an allergic reaction in a patient treated with those compounds.

The present invention is directed to a method of altering an alkaloid content in a plant host comprising the steps of infecting a plant host with a monopartite RNA viral vector that comprises modified tobravirus RNA-1. The modified tobravirus RNA-1 comprises a foreign RNA sequence operably linked to the stop codon of the RNA sequence that codes for a 16 k Da cysteine-rich protein of RNA-1. The foreign RNA sequence is involved in the biosynthesis of secondary metabolites, such as alkaloids. For example, the foreign RNA sequence may encode all or part of the putrescine N-methyltransferase. The present invention is also directed to a method of altering an alkaloid content in a plant host comprising the steps of infecting a plant host with a bipartite RNA viral vector that comprises the above modified tobravirus RNA-1 and tobravirus RNA-2.

The present invention is further directed to a method of altering an alkaloid content in a plant host. The method comprises the steps of infecting a plant host with a bipartite RNA viral vector that comprises: (a) tobravirus RNA-1; (b) modified tobravirus RNA-2 that comprises one or more promoter-gene constructs comprising a subgenomic promoter and a foreign RNA sequence, wherein said subgenomic promoter is operably linked to the 5' end of said foreign RNA sequence, and said promoter-gene construct is inserted in place of the 2 C gene of a tobravirus. The foreign RNA sequence is involved in the biosynthesis of secondary metabolites, such as alkaloids. For example, the foreign RNA sequence may encode all or part of the putrescine N-methyltransferase. The invention is exemplified by transfecting *N. benthamiana* plants with a bipartite RNA viral vector that comprises a foreign RNA sequence. The transfected plants showed an 8-fold decrease in the accumulation of the alkaloid nicotine. The protein encoded by the foreign RNA was shown to have high identities and positives with *N. tabacum* putrescine N-methyltransferase. This is the first time that the alkaloid content in a plant was altered by cytoplasmic inhibition of an endogenous gene using a viral RNA vector. The present invention is also directed to a plant host which has an altered alkaloid content, prepared by the above method.

The recombinant plant viral nucleic acid is prepared by cloning a viral nucleic acid. If the viral nucleic acid is DNA, it can be cloned directly into a suitable vector using conventional techniques. One technique is to attach an origin of replication to the viral DNA which is compatible with the cell to be transfected. If the viral nucleic acid is RNA, a full-length DNA copy of the viral genome is first prepared by well-known procedures. For example, the viral RNA is transcribed into DNA using reverse transcriptase to produce subgenomic DNA pieces, and a double-stranded DNA made using DNA polymerases. The cDNA is then cloned into appropriate vectors and cloned into a cell to be transfected. Alternatively, the cDNA is ligated into the vector and is directly transcribed into infectious RNA in vitro, the infectious RNA is then inoculated onto the plant host. The cDNA pieces are mapped and combined in a proper sequence to produce a full-length DNA copy of the viral RNA genome, if necessary. A DNA sequence for a subgenomic promoter, such as a subgenomic coat protein promoter, may optionally be inserted into the nucleic acid at a non-essential site, according to the particular embodiment of the invention utilized. Nonessential sites are those that do not affect the biological properties of the plant viral nucleic acids. Since the RNA genome is the infective agent, the cDNA is positioned adjacent a suitable promoter so that the RNA is produced in the production cell. The RNA can be capped by the addition of a nucleotide in a 5'-5' linkage using conventional techniques (Dawson et al., *Proc. Natl. Acad. Sci. USA,* 83:1832 (1986). One or more nucleotides may be added between the transcription start site of the promoter and the start of the cDNA of a viral nucleic acid to construct an infectious viral vector. In a preferred embodiment of the present invention, the inserted nucleotide sequence contains a G at the 5'-end. In one embodiment, the inserted nucleotide sequence is GNN, GTN, or their multiples, $(GNN)_x$ or $(GTN)_x$. The capped RNA can be packaged in vitro with added coat protein from TMV to make assembled virions. These assembled virions can then be used to inoculate plants or plant tissues.

Alternatively, an uncapped RNA may be employed in the embodiments of the present invention. Contrary to the practiced art in scientific literature and in an issued patent (Ahlquist et al., U.S. Pat. No. 5,466,788), uncapped transcripts for virus expression vectors are infective on both plants and in plant cells. Capping is not a prerequisite for establishing an infection of a virus expression vector in plants, although capping increases the efficiency of infection.

One feature of the recombinant plant viral nucleic acids useful in the present invention is that they comprise one or more non-native nucleic acid sequences capable of being transcribed in a plant host. These nucleic acid sequences may be native nucleic acid sequences that occur in a plant host. Preferably, these nucleic acid sequences are non-native nucleic acid sequences that do not normally occur in a plant host. These nucleic acid sequences are derived from a donor plant, which may be the same or different from the plant host. The donor plant and the plant host may be genetically remote or unrelated: they may belong to different genus, family, order, class, subdivision, or division. Donor plants and plant hosts include plants of commercial interest, such as food crops, seed crops, oil crops, ornamental crops and forestry crops. For example, wheat, rice, corn, potatoes, barley, tobaccos, soybean canola, maize, oilseed rape, Arabidopsis, Nicotiana can be selected as a donor plant or a plant host. Plant hosts include those capable of being infected by an infectious RNA or a virus containing a recombinant viral nucleic acid. Preferred plant hosts include Nicotiana, such as, *Nicotiana benthamiana*, and *Nicotiana cleavlandii*, and *Arabidopsis*. Plant are grown from seed in a mixture of "Peat-Lite Mix™ (Speedling, Inc. Sun City, Fla.) and Nutricote™ controlled release fertilizer 14-14-14 (Chiss-Asahi Fertilizer Co., Tokyo, Japan). Plants are grown in a controlled environment provided 16 hours of light and 8 hours of darkness. Sylvania "Gro-Lux/Aquarium" wide spectrum 40 watt flourescent grow lights. (Osram Sylvania Products, Inc. Danvers, Mass.) are used. Temperatures are kept at around 80° F. during light hours and 70° F. during dark hours. Humidity is between 60 and 85%.

To prepare a DNA insert comprising a nucleic acid sequence of a donor plant, the first step is to construct a library of cDNAs, genomic DNAs, or a pool of RNAs of the plant of interest. Full-length cDNAs can be obtained from public or private repositories, for example, cDNA library of *Arabidopsis thaliana* can be obtained from the Arabidopsis Biological Resource Center. Alternatively, cDNA library can be prepared from a field sample by methods known to a person of ordinary skill, for example, isolating mRNAs and transcribing mRNAs into cDNAs by reverse transcriptase (see, e.g., Sambrook et al., *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, New York (1987)). Genomic DNAs represented in BAC (bacterial artificial chromosome), YAC (yeast artificial chromosome), or TAC (transformation-competent artificial chromosome, Liu et al., *Proc. Natl. Acad. Sci. USA,* 96:6535-6540 (1999)) libraries can be obtained from public or private repositories. for example, the Arabidopsis Biological Resource Center. The BAC/YAC/TAC DNAs or cDNAs can be mechanically size-fractionated or digested by an enzyme to smaller fragments. The fragments are ligated to adapters with cohesive ends, and shotgun-cloned into recombinant viral nucleic acid vectors. Alternatively, the fragments can be blunt-end ligated into recombinant viral nucleic acid vectors. Recombinant plant viral nucleic acids containing a nucleic acid sequence derived from the cDNA library or genomic DNA library is then constructed using conventional techniques.

The recombinant viral nucleic acid vectors produced comprise one or more nucleic acid inserts derived from a donor plant. The nucleic acid sequences of the recombinant viral nucleic acids are transcribed as RNAs in a plant host; the RNA are capable of regulating the expression of one or more phenotypic traits by an antisense or a positive sense mechanism, by inhibition of an endogenous plant host gene or by expression of a protein in a plant host. The nucleic acid sequence may also code for the expression of more than one phenotypic trait. Sequences from wheat, rice, corn, potato, barley, tobacco, soybean, canola, maize, oilseed rape, Arabidopsis, and other crop species may be used to assemble the DNA libraries. This method may thus be used to search for useful dominant gene phenotypes from DNA libraries through the gene expression.

For a multipartite viral vector construct, more than one nucleic acid is prepared when creating the recombinant plant viral nucleic acid. In this case, each nucleic acid would require its own origin of assembly. Each nucleic acid could be prepared to contain a subgenomic promoter and a non-native nucleic acid.

In some embodiments of the instant invention, methods to increase the representation of gene sequences in virus expression libraries may also be achieved by bypassing the genetic bottleneck of propagation in bacterial cells. For example, cell-free methods may be used to assemble sequence libraries or individual arrayed sequences into virus expression vectors and reconstruct an infectious virus, such that the final ligation product can be transcribed and the resulting RNA can be used for plant, plant tissue or plant cell inoculation/infection. A more detailed discussion is presented in a co-owned U.S. application Ser. No. 09/359,303 (now abandoned) , which is incorporated herein by reference.

Techniques of Infecting a Plant

The host can be infected with a recombinant viral nucleic acid or a recombinant plant virus by conventional techniques. Suitable techniques include, but are not limited to, leaf abrasion, abrasion in solution, high velocity water spray, and other injury of a host as well as imbibing host seeds with water containing the recombinant viral RNA or recombinant plant virus. More specifically, suitable techniques include:

(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.

(c) Vacuum Infiltration. Inoculations may be accomplished by subjecting a host organism to a substantially vacuum pressure environment in order to facilitate infection.

(d) High Speed Robotics Inoculation. Especially applicable when the organism is a plant, individual organisms may be grown in mass array such as in microtiter plates. Machinery such as robotics may then be used to transfer the nucleic acid of interest.

(e) High Pressure Spray of Single Leaves. Single plant inoculations can also be performed by spraying the leaves with a narrow, directed spray (50 psi, 6-12 inches from the leaf) containing approximately 1% carborundum in the buffered vector solution.

(f) Ballistics (High Pressure Gun) Inoculation. Single plant inoculations can also be performed by particle bombardment. A ballistics particle delivery system (BioRad Laboratories, Hercules, (A) can be used to transfect plants such as *N. benthamiana* as described previously (Nagar et al., *Plant Cell,* 7:705-719 (1995)).

Determine Biochemical or Phenotypic Changes in a Plant Host

After a host is infected with a recombinant viral nucleic acid comprising a nucleic acid insert derived from a cDNA library or a genomic library, one or more biochemical or phenotypic changes in a plant host is determined. The biochemical or phenotypic changes in the infected plant host is correlated to the biochemistry or phenotype of a plant host that is uninfected. Optionally, the biochemical or phenotypic changes in the infected plant host is further correlated to a plant host that is infected with a viral vector that contains a control nucleic acid of a known sequence in an antisense orientation; the control nucleic acid has similar size but is different in sequence from the nucleic acid insert derived from the library. For example, if the nucleic acid insert derived from the library is identified as encoding a GTP binding protein, a nucleic acid derived from a gene encoding green fluorescent protein can be used as a control nucleic acid. Green fluorescent protein is known not be have the same effect as the GTP binding protein when expressed in plants.

Those of skill in the art will readily understand that there are many methods to determine phenotypic or biochemical change in a plant and to determine the function of a nucleic acid, once the nucleic acid is localized or systemic expressed in a plant host. In a preferred embodiment, the phenotypic or biochemical trait may be determined by observing phenotypic changes in a host by methods including visual, morphological, macroscopic or microscopic analysis. For example, growth change such as stunting, hyperbranching, and necrosis; structure change such as vein banding, ring spot, etching; color change such as bleaching, chlorosis, or other color; and other changes such as marginal, mottled, patterening, punctate, and reticulate are easily detected. In another embodiment, the phenotypic or biochemical trait may be determined by complementation analysis, that is, by observing the endogenous gene or genes whose function is replaced or augmented by introducing the nucleic acid of interest. A discussion of such phenomenon is provided by Napoli et al., The Plant Cell 2:279-289 (1990). In a third embodiment, the phenotypic or biochemical trait may be determined by analyzing the biochemical alterations in the accumulation of substrates or products from enzymatic reactions according to any means known by those skilled in the art. In a fourth embodiment, the phenotypic or biochemical trait may be determined by observing any changes in biochemical pathways which may be modified in a host organism as a result of expression of the nucleic acid. In a fifth embodiment, the phenotypic or biochemical trait may be determined utilizing techniques known by those skilled in the art to observe inhibition of endogenous gene expression in the cytoplasm of cells as a result of expression of the nucleic acid. In a sixth embodiment, the phenotypic or biochemical trait may be determined utilizing techniques known by those skilled in the art to observe changes in the RNA or protein profile as a result of expression of the nucleic acid. In a seventh embodiment, the phenotypic or biochemical trait may be determined by selection of organisms such as plants capable of growing or maintaining viability in the presence of noxious or toxic substances, such as, for example herbicides and pharmaceutical ingredients.

Phenotypic traits in plant cells, which may be observed microscopically, macroscopically or by other methods, include improved tolerance to herbicides, improved tolerance to extremes of heat or cold, drought, salinity or osmotic stress; improved resistance to pests (insects, nematodes or arachnids) or diseases (fungal, bacterial or viral), production of enzymes or secondary metabolites; male or female sterility; dwarfness; early maturity; improved yield, vigor, heterosis, nutritional qualities, flavor or processing properties, and the like. Other examples include the production of important proteins or other products for commercial use, such as lipase, melanin, pigments, alkaloids, antibodies, hormones, pharmaceuticals, antibiotics and the like. Another useful phenotypic trait is the production of degradative or inhibitory enzymes, for example, enzymes preventing or inhibiting the root development in malting barley, or enzymes determining response or non-response to a systemically administered drug in a human. The phenotypic trait may also be a secondary metabolite whose production is desired in a bioreactor.

Biochemical changes can also be determined by analytical methods, for example, in a high-throughput, fully automated fashion using robotics. Suitable biochemical analysis may include MALDI-TOF, LC/MS, GC/MS, two-dimensional IEF/SDS-PAGE, ELISA or other methods of analyses. The clones in the plant viral vector library may then be functionally classified based on metabolic pathway affected or visual/selectable phenotype produced in the plant. This process enables the rapid determination of gene function for unknown nucleic acid sequences of a plant origin. Furthermore, this process can be used to rapidly confirm function of full-length DNA's of unknown gene function. Functional identification of unknown nucleic acid sequences in a plant library may then rapidly lead to identification of similar unknown sequences in expression libraries for other crop species based on sequence homology.

One useful means to determine the function of nucleic acids transfected into a host is to observe the effects of gene silencing. Traditionally, functional gene knockout has been achieved following inactivation due to insertion of transposable elements or random integration of T-DNA into the chromosome, followed by characterization of conditional, homozygous-recessive mutants obtained upon backcrossing. Some teachings in these regards are provided by WO 97/42210 which is herein incorporated by reference. As an alternative to traditional knockout analysis, an EST/DNA library from an organism, for example *Arabidopsis thaliana*, may be assembled into a plant viral transcription plasmid. The nucleic acid sequences in the transcription plasmid library may then be introduced into plant cells as part of a functional RNA virus which post-transcriptionally silences the homologous target gene. The EST/DNA sequences may be introduced into a plant viral vector in either the plus or minus sense orientation, and the orientation can be either directed or random based on the cloning strategy. A high-throughput, automated cloning scheme based on robotics may be used to assemble and characterize the library. Gene silencing of plant genes is induced by delivering an RNA capable of base pairing with itself to form double stranded regions. This approach could be used with any plant gene to assist in the identification of the function of a particular gene sequence.

The present invention provides a method to produce transfected plants containing viral-derived RNA in the cytoplasm. Such method is much faster than the time required to obtain genetically engineered antisense transgenic plants. Systemic infection and expression of viral antisense RNA occurs as short as four days post inoculation, whereas it takes several months or longer to create a single transgenic plant. The invention provides a method to identify genes involved in the regulation of plant growth by inhibiting the expression of specific endogenous genes or by overexpression of a protein using viral vectors, which replicate solely in the cytoplasm. This invention provides a method to characterize specific genes and biochemical pathways in donor plants or in plant hosts using an RNA viral vector.

Cytoplasmic Inhibition of Gene Expression in Transfected Plants

Nucleic acid sequences that may result in changing a host phenotype include those involved in cell growth, proliferation, differentiation and development; cell communication; and the apoptotic pathway. Genes regulating growth of cells or organisms include, for example, genes encoding a GTP binding protein, a ribosomal protein L19 protein, an S18 ribosomal protein, etc. Henry, et al. (*Cancer Res.*, 53:1403-1408 (1993)) report that the erb B-2 (or HER-2 or neu) gene was amplified and overexpressed in one-third of cancers of the breast, stomach, and ovary; and the mRNA encoding the ribosomal protein L19 was more abundant in breast cancer samples that express high levels of erbB-2. Lijsebettens, et al. (*EMBO J.*, 13:3378-3388 (1994)) report that in Arabidopsis, mutation at PFL caused pointed first leaves, reduced fresh weight and growth retardation. PFL codes for ribosomal protein S18, which has a high homology with the rat S18 protein. Genes involved in development of cells or organisms include, for example, homeobox-containing genes and genes encoding G-protein-coupled receptor proteins such as the rhodopsin family. Homeobox genes are a family of regulatory genes containing a common 183-nucleotide sequence (homeobox) and coding for specific nuclear proteins (homeoproteins) that act as transcription factors. The homeobox sequence itself encodes a 61-amino-acid domain, the homeodomain, responsible for recognition and binding of sequence-specific DNA motifs. The specificity of this binding allows homeoproteins to activate or repress the expression of batteries of downstream target genes. Initially identified in genes controlling Drosophila development, the homeobox has subsequently been isolated in evolutionarily distant animal species, plants, and fungi. Several indications suggest the involvement of homeobox genes in the control of cell growth and, when dysregulated, in oncogenesis (Cillo et al., *Exp. Cell Res.*, 248:1-9 (1999). Other nucleic acid sequences that may result in changes of an organism include gene-encoding receptor proteins such as hormone receptors, cAMP receptors, serotonin receptors, and the calcitonin family of receptors; and light-regulated DNA encoding a leucine (Leu) zipper motif (Zheng, et al., *Plant Physiol.*, 116:27-35 (1998)). Deregulation or alteration of the process of cell growth, proliferation, differentiation and development; cell communication; and the apoptotic pathways may result in cancer. Therefore, identifying the nucleic acid sequences involved in those processes and determining their functions are beneficial to the human medicine; it also provides a tool for cancer research.

One problem with gene silencing in a plant host is that many plant genes exist in multigene families. Therefore, effective silencing of a gene function may be especially problematic. According to the present invention, more than one nucleic acid may be inserted into the viral vector to effectively silence a particular gene function or to silence the function of a multigene family. It is presently believed that about 20% of plant genes exist in multigene families.

A detailed discussion of some aspects of cytoplasmic inhibition of gene expression in plants is provided in U.S. Pat. No. 5,922,602 and WO95/34668, the disclosures of which are incorporated herein by reference. RNA can reduce the expression of a target gene, or a gene of interest, through inhibitory RNA interactions with the mRNA that occur in the cytoplasm and/or the nucleus of a cell.

Isolating a Conserved Gene From a Plant

The present invention also provides a method of isolating a conserved gene such as a gene encoding a GTP binding protein, DEAD box RNA helicase, Nop 10-like small nuclear ribonucleoprotein, putrescine N-methyltransferase, methionine synthase, and PRP19-like spliceosomal protein, and CRS2 chloroplast gene from rice, barley, corn, soybean, maize, oilseed, and other plant of commercial interest, using another gene having homology with gene being isolated. Libraries containing full-length cDNAs from a donor plant such as rice, barley, corn, soybean and other important crops can be obtained from public and private sources or can be prepared from plant mRNAs. The cDNAs are inserted in viral vectors or in small subcloning vectors such as pBluescript (Strategene), pUC18, M13, or pBR322. Transformed bacteria are then plated and individual clones selected by a standard method. The bacteria transformants or DNAs are rearrayed at high density onto membrane filters or glass slides. Full-length cDNAs encoding the protein of interese can be identified by probing filters or slides with labeled nucleic acid inserts which result in changes in a plant host. Useful labels include radioactive, fluorescent, or chemiluminecent molecules, enzymes, etc.

Alternatively, genomic libraries containing sequences from rice, barley, corn, soybean and other important crops can be obtained from public and private sources, or be prepared from plant genomic DNAs. BAC clones containing entire plant genomes have been constructed and organized in a minimal overlapping order. Individual BACs are sheared to fragments and directly cloned into viral vectors. Clones that completely cover an entire BAC form a BAC viral vector sublibrary. Genomic clones can be identified by probing filters containing BACs with labeled nucleic acid inserts which result in changes in a plant host, or for example, with labeled probes prepared from DNAs encoding GTP binding protein from Arabidopsis. Useful labels include radioactive, fluorescent, or chemiluminecent molecules, enzymes, etc. BACs that hybridize to the probe are selected and their corresponding BAC viral vectors are used to produce infectious RNAs. Plants that are transfected with the BAC sublibrary are screened for change of function, for example, change of growth rate or change of color. Once the change of function is observed, the inserts from these clones or their corresponding plasmid DNAs are characterized by dideoxy sequencing. This provides a rapid method to obtain the genomic sequence for a plant protein, for example, a GTP binding protein. Using this method, once the DNA sequence in one plant such as *Arabidopsis thaliana* is identified, it can be used to identify conserved sequences of similar function that exist in other plant libraries.

Large amounts of DNA sequence information are being generated in the public domain and may be entered into a relational database. Links may be made between sequences from various species predicted to carry out similar biochemical or regulatory functions. Links may also be generated between predicted enzymatic activities and visually displayed biochemical and regulatory pathways. Likewise, links may be generated between predicted enzymatic or regulatory activity and known small molecule inhibitors, activators, substrates or substrate analogs. Phenotypic data from expression libraries expressed in transfected hosts may be automatically linked within such a relational database. Genes with similar predicted roles of interest in other crop plants may be rapidly discovered.

Definitions

In order to provide an even clearer and more consistent understanding of the specification and the claims, including the scope given herein to such terms, the following definitions are provided:

Adjacent: A position in a nucleotide sequence proximate to and 5' or 3' to a defined sequence. Generally, adjacent means within 2 or 3 nucleotides of the site of reference.

Anti-Sense Inhibition: A type of gene regulation based on cytoplasmic, nuclear or organelle inhibition of gene expression due to the presence in a cell of an RNA molecule complementary to at least a portion of the mRNA being translated. It is specifically contemplated that the RNA molecule may be from either an RNA virus or mRNA from the host cells genome or from a DNA virus. The gene regulation may either inhibit the endogenous host gene or the target gene of interest.

Cell Culture: A proliferating group of cells which may be in either an undifferentiated or differentiated state, growing contiguously or non-contiguously.

Chimeric Sequence or Gene: A nucleotide sequence derived from at least two heterologous parts. The sequence may comprise DNA or RNA.

Coding Sequence: A deoxyribonucleotide or ribonucleotide sequence which, when either transcribed and translated or simply translated, results in the formation of a cellular polypeptide or a ribonucleotide sequence which, when translated, results in the formation of a cellular polypeptide.

Compatible: The capability of operating with other components of a system. A vector or plant or animal viral nucleic acid which is compatible with a host is one which is capable of replicating in that host. A coat protein which is compatible with a viral nucleotide sequence is one capable of encapsidating that viral sequence.

Complementation Analysis: As used herein, this term refers to observing the changes produced in an organism when a nucleic acid sequence is introduced into that organism after a selected gene has been deleted or mutated so that it no longer functions fully in its normal role. A complementary gene to the deleted or mutated gene can restore the genetic phenotype of the selected gene.

Dual Heterologous Subgenomic Promoter Expression System (DHSPES): a plus stranded RNA vector having a dual heterologous subgenomic promoter expression system to increase, decrease, or change the expression of proteins, peptides or RNAs, preferably those described in U.S. Pat. Nos. 5,316,931, 5,811,653, 5,589,367, and 5,866,785, the disclosure of which is incorporated herein by reference.

Expressed sequence tags (ESTs): A partial sequence of a clone picked at random from a cDNA library and used in the identification of the gene being expressed in a particular tissue. They may be present in either the 5' or the 3' orientation. ESTs have been shown useful for identifying particular genes.

Expression: The term as used herein is meant to incorporate one or more of transcription, reverse transcription and translation.

A functional Gene Profile: The collection of genes of an organism which code for a biochemical or phenotypic trait. The functional gene profile of an organism is found by screening nucleic acid sequences from a donor organism by over expression or suppression of a gene in a host organism. A functional gene profile requires a collection or library of nucleic acid sequences from a donor organism. A functional gene profile will depend on the ability of the collection or library of donor nucleic acids to cause over-expression or suppression in the host organism. Therefore, a functional gene profile will depend upon the quantity of donor genes capable of causing over-expression or suppression of host genes or of being expressed in the host organism in the absence of a homologous host gene.

Foreign DNA or RNA: Any RNA or DNA sequence that does not normally occur in the cell or organism in which it is placed. Examples include recombinant viral nucleic acids and genes or ESTs contained therein. That is, an RNA or DNA sequence may be foreign with respect to a viral nucleic acid. Such an RNA or DNA sequence would not naturally occur in the viral nucleic acid. Also, an RNA or DNA sequence may be foreign with respect to a host organism. That is, such a RNA or DNA sequence would not naturally occur in the host organism.

Gene: A discrete nucleic acid sequence responsible for producing one or more cellular products and/or performing one or more intercellular or intracellular functions.

Gene silencing: A reduction in gene expression. A viral vector expressing gene sequences from a host may induce gene silencing of homologous gene sequences.

Homology: A degree of nucleic acid similarity in all or some portions of a gene sequence sufficient to result in gene suppression when the nucleic acid sequence is delivered in the antisense orientation.

Host: A cell, tissue or organism capable of replicating a nucleic acid such as a vector or viral nucleic acid and which is capable of being infected by a virus containing the viral vector or viral nucleic acid. This term is intended to include prokaryotic and eukaryotic cells, organs, tissues or organisms, where appropriate. Bacteria, fungi, yeast, and animal (cell, tissues, or organisms), are examples of a host.

Infection: The ability of a virus to transfer its nucleic acid to a host or introduce a viral nucleic acid into a host, wherein the viral nucleic acid is replicated, viral proteins are synthesized, and new viral particles assembled. In this context, the terms "transmissible" and "infective" are used interchangeably herein. The term is also meant to include the ability of a selected nucleic acid sequence to integrate into a genome, chromosome or gene of a target organism.

Insert: a stretch of nucleic acids, typically more than 20 base pairs long.

Multigene family: A set of genes descended by duplication and variation from some ancestral gene. Such genes may be clustered together on the same chromosome or dispersed on different chromosomes. Examples of multigene families include those which encode the histones, hemoglobins, immunoglobulins, histocompatibility antigens, actions, tubulins, keratins, collagens, heat shock proteins, salivary glue proteins, chorion proteins, cuticle proteins, yolk proteins, and phaseolins.

Non-Native: Any RNA or DNA sequence that does not normally occur in the cell or organism in which it is placed. Examples include recombinant viral nucleic acids and genes or ESTs contained therein. That is, an RNA or DNA sequence may be non-native with respect to a viral nucleic acid. Such an RNA or DNA sequence would not naturally occur in the viral nucleic acid. Also, an RNA or DNA sequence may be non-native with respect to a host organism. That is, such a RNA or DNA sequence would not naturally occur in the host organism.

Nucleic acid: As used herein the term is meant to include any DNA or RNA sequence from the size of one or more nucleotides up to and including a complete gene sequence. The term is intended to encompass all nucleic acids whether naturally occurring in a particular cell or organism or non-naturally occurring in a particular cell or organism.

Nucleic acid of interest: The term is intended to refer to the nucleic acid sequence whose function is to be determined. The sequence will normally be non-native to a viral vector but may be native or non-native to a host organism.

Phenotypic Trait: An observable, measurable or detectable property resulting from the expression or suppression of a gene or genes.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in plant or in culture. This term is intended to include a whole plant, plant cell, plant organ, protoplast, cell culture, or any group of plant cells organized into a structural and functional unit.

Positive-sense inhibition: A type of gene regulation based on cytoplasmic inhibition of gene expression due to the presence in a cell of an RNA molecule substantially homologous to at least a portion of the mRNA being translated.

Promoter: The 5'-flanking, non-coding sequence substantially adjacent a coding sequence which is involved in the initiation of transcription of the coding sequence.

Protoplast: An isolated plant or bacterial cell without some or all of its cell wall.

Recombinant Viral Nucleic Acid: Viral nucleic acid which has been modified to contain non-native nucleic acid sequences. These non-native nucleic acid sequences may be from any organism or purely synthetic, however, they may also include nucleic acid sequences naturally occurring in the organism into which the recombinant viral nucleic acid is to be introduced.

Recombinant Virus: A virus containing the recombinant viral nucleic acid.

Subgenomic Promoter: A promoter of a subgenomic mRNA of a viral nucleic acid.

Substantial Sequence Homology: Denotes nucleotide sequences that are substantially functionally equivalent to one another. Nucleotide differences between such sequences having substantial sequence homology are insignificant in affecting function of the gene products or an RNA coded for by such sequence.

Systemic Infection: Denotes infection throughout a substantial part of an organism including mechanisms of spread other than mere direct cell inoculation but rather including transport from one infected cell to additional cells either nearby or distant.

Transient Expression: Expression of a nucleic acid sequence in a host without insertion of the nucleic acid sequence into the host genome, such as by way of a viral vector. Transient expression includes expression in the cytoplasm and episomes.

Transposon: A nucleotide sequence such as a DNA or RNA sequence which is capable of transferring location or moving within a gene, a chromosome or a genome.

EXAMPLES

The following examples further illustrate the present invention. These examples are intended merely to be illustrative of the present invention and are not to be construed as being limiting.

Example 1

Figure 2:
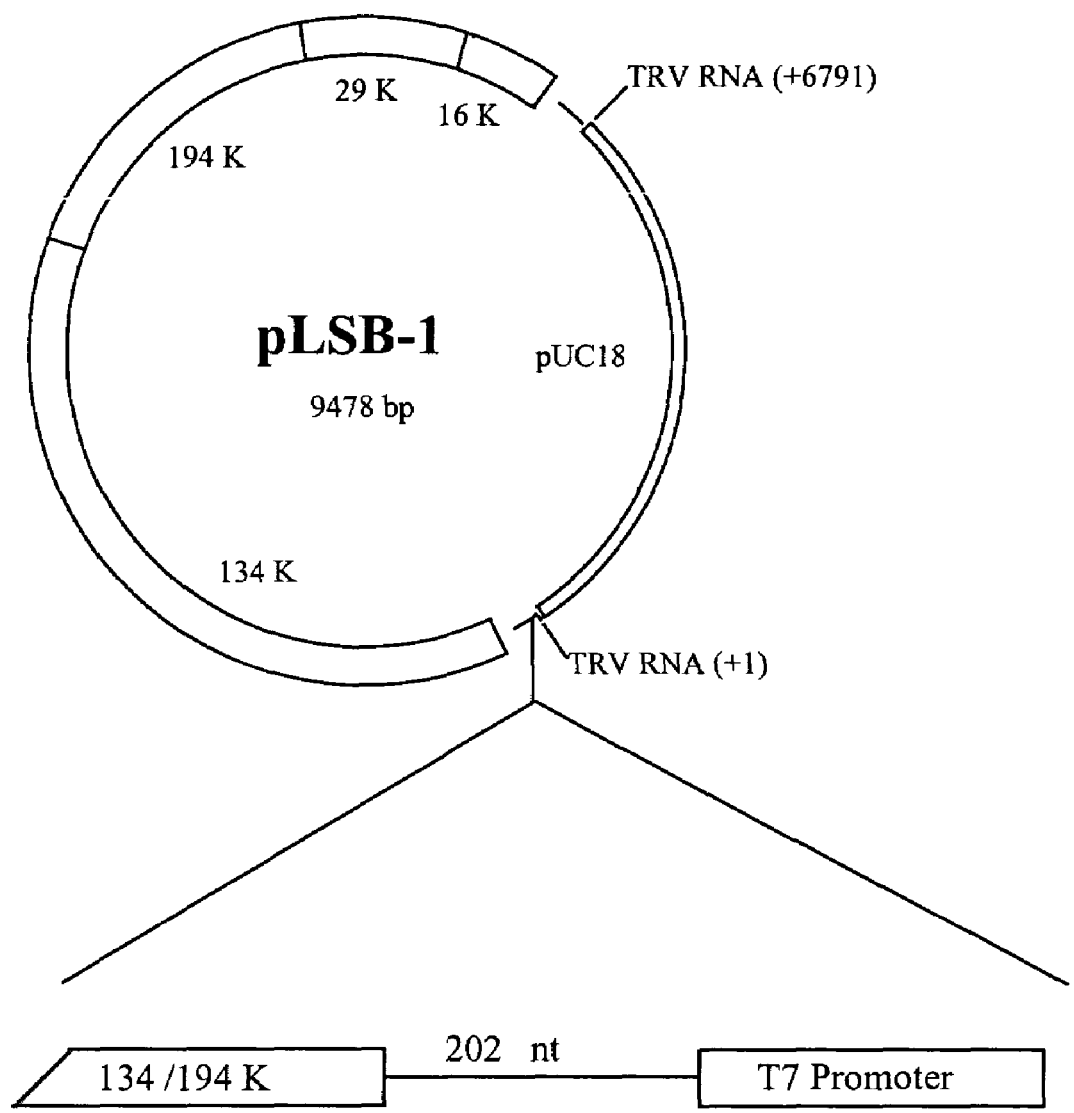
FIG. 2 depicts the expression vector pLSB-1. This plasmid contains the T7 promoter, the TRV RNA-1 134-, 194-, 29-, 16-kDa ORFs, and part of the pUC18 plasmid.

Development of a Tobraviral Vector for Cytoplasmic Inhibition of Gene Expression in Transfected Plants Nematode-transmissible TRV, PpK20, was isolated by Ploeg, Robinson, and Brown (*J. Gen. Virol.* 74:1463-6 (1993)). A single-lesion purification of this strain was used to make the NM stock (where RNA-1 is purified from the RNA-2, and is maintained as an RNA-1 only infection). Total RNA was purified from plants transfected with NM stock and mixed with infectious RNA-2 from pK20-2b-PDS(+) construct that was prepared by in vitro transcription using T7 DNA-dependent RNA polymerase. The pooled RNAs were used to mechanically coinoculate *N. benthamiana*. Crude leaf extract containing TRV virions was isolated from systemically infected tissue and used to inoculate *N. benthamiana*. Two weeks after transfection, virions were purified from systemically infected leaf tissue by PEG precipitation (Gooding G V Jr., Hebert T T. *A simple technique for purification of tobacco mosaic virus in large quantities*. Phytopathology 57(11):1285 (1967)). The TRV RNA-1 was isolated using the RNeasy Mini Kit (Qiagen®) and cDNA was synthesized using the oligonucleotide 5'-TTAATTAAGCATGCGGATC-CCGTACGGGCGTAATAACGCTTACGTAGGCGAGG GGTTTTAC-3' (SEQ ID NO: 23) and the cDNA Synthesis System (Gibco BRL®). A 6791 bp full length fragment (1-6791) from TRV RNA-1 encoding the replicase (134/194 kDa), movement protein (29 kDa) and Cysteine Rich Protein (16 kDa) was amplified from the cDNA by PCR using oligonucleotides 5'-ATGAAGAGCATGCTAATACGACTCAC TATAGATAAAACATTTCAATCCTTTGAACGC-3' (upstream) (SEQ ID NO: 24) and 5'-TTCATCTGGATC-CCGGGCGTAATAACGCTTACGTAGGCG-3' (downstream) (SEQ ID NO: 25) and cloned into the Sph I/Bam HI of pUC18 of (Yanisph-Perron, et al., *Gene* 33:103-19 (1985)) creating plasmid LSB-1 (FIG. 2).

DNA Sequencing and Computer Analysis

The nucleotide sequencing of LSB-1 was carried out by dideoxy termination using double-stranded templates (Sanger, et al. *Pro. Natl. Acad. Sci.* 74:5463-5467 (1977)). Nucleotide sequence analysis and amino acid sequence comparisons were performed using DNA Strider and SEQUENCHER® (Genecodes) programs. LSB-1 had 29 point mutations when compared to the published sequence for PpK20 RNA-1 (Visser, et al., *Virology* 263:155-65 (1999)). ACCESSION AF166084). All of these point mutations were in the replicase gene, and many coded for amino acid substitutions. The sequence of LSB-1 is shown in FIG. 3.

Isolation and Modification of TRV RNA-2 cDNA

Figure 4:
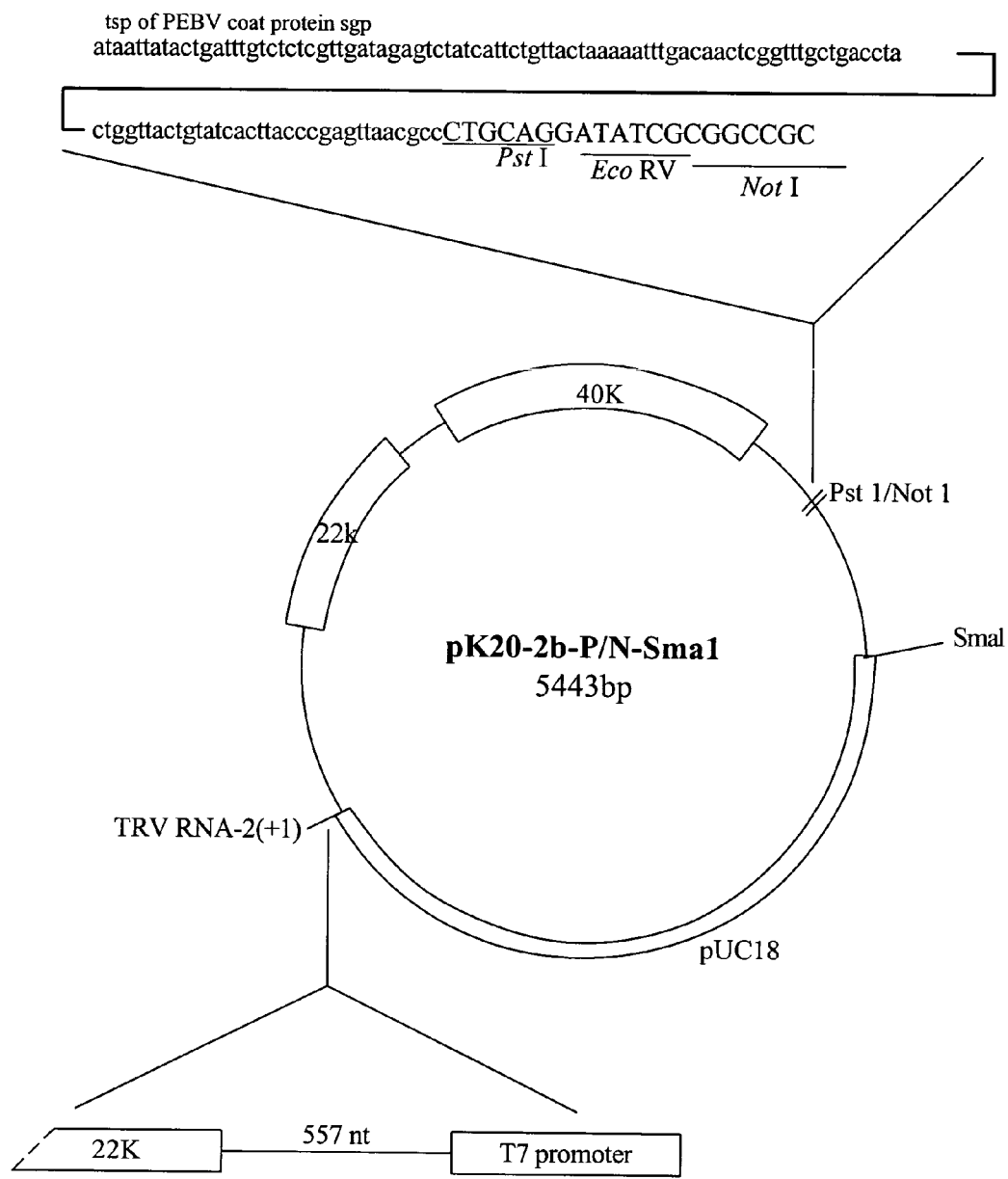
FIG. 4 depicts the plasmid pK20-2b-P/N-SmaI. This plasmid contains the T7 promoter, the TRV RNA-2 22-, 40-kDa ORFs, the Pea Early Browning Virus (PEBV) subgenomic promoter, followed by the PstI and NotI restriction sites, a SmaI site linearizing the plasmid prior to transcription, and part of the pUC18 plasmid. The transcriptional start point (tsp) of the subgenomic RNA from the PEBV coat promoter is indicated with a period (.). (SEQ ID NO: 2).

TRV RNA-2 encodes a capsid protein and two non-structural proteins, 2b and 2c. RNA-2 is not essential for infection in plants. It has been previously modified for expression of heterologous proteins. In this experiment, construct TRV-GFP, (MacFarlane and Popovich, *Virology* 267:29-35 (2000)) which has the 2b and 2c genes of TRV RNA-2 replaced with the pea early browning virus (PEBV) coat protein subgenomic promoter, was modified by PCR-directed mutagenesis. Oligonucleotides 5'-GTCCTAATCCCTAGGG ATT-TAAGG-3' (upstream, TRV2AVR2 SEQ ID NO: 26) and 5'-CTTTGGAAATTGCAGAAAC-3' (downstream, TRV4307-4289, SEQ D NO: 27) were used to PCR amplify the region between the Avr II and Pst I sites of plasmid TRV-2b-GFP (MacFarlane and Popovich, 2000), which is identical to TRV-GFP but retains the 2b gene. Oligonucleotides 5'-GTTTCTGCAATTTCCAAAG-3' (upstream, TRV4289-4307, SEQUENCE NO.28) and 5'-GAAT-TCGGGGTACCGCGGCCGCGATA TCCTGCAGGGCGT-TAACTC-3' (downstream, TRVPST/NOT PL. SEQUENCE ID NO: 29) were used to PCR amplify the region between the Pst I and the 3'-end of the PEBV coat protein subgenomic promoter of construct TRV-2b-GFP. The two resulting PCR fragments were then joined by splice overlap PCR using oligonucleotides TRV2AVR2 and TRVPST/NOT PL and cloned into TRV-GFP cut with Avr II and Kpn I. The resulting construct, pK20-2b-P/N-SmaI (FIG. 4), includes the 2b gene and has unique Pst I, EcoRV, and Not I cloning sites, with a Sma I site at the 3'-terminus of the TRV RNA-2 cDNA insert. Construct pK20-2b-N/P-SmaI, in which the Pst I and Not I sites were reversed, was constructed as described above, except oligonucleotide TRVNOT/PST PL (5'-GAA TTCGG-TACCCTGCAGGATATCGCGGCCGCG-GCGTTAACTCGG-3', SEQUENCE ID NO: 30) was used instead of oligonucleotide TRVPST/NOT PL.

Plasmid pK20-2b-P/N-SmaI was modified by adding a Pme I site immediately upstream of the Sma I site. Oligonucleotides 5'-AAGGAAAAAAGCGGCCGCGGTACCC CG-3' (upstream, TRVNOT4979-4995, SEQUENCE ID NO: 31) and 5'-CGGATCC CCCGGGTTTAAACGGG CGTAATAACGCTTACGTAG-3' (downstream, TRV23PME1 SEQUENCE ID NO: 32) were used to PCR amplify the region between the Not I and Sma I sites of pK20-2b-P/N-SmaI. The PCR fragment then was recloned into pK20-2b-P/N-SmaI cut with Not I and Sma I to form the construct pK20-2b-P/N-PmeI. The Pme I site is an eight base-pair recognition site, thereby reducing the probability of cutting within cloned inserts when compared to Sma I (six base-pair recognition site).

Plasmid pK20-2b-P/N-PmeI was further modified by adding a unique Xho I restriction site. Oligonucleotides 5'-AAACTGCAGCTCGAGCTGATTTAA-CAAATTTTAAC-3' (upstream. PST/XHO ZEO, SEQUENCE ID NO. 33) and 5'-TTTTCCTTTTGCGGCC GCGCACGTGTCAGT CCTGCTCCTCGG-3' (downstream, ZEO NOT SEQUENCE ID NO: 34) were used to PCR amplify the zeocin antibiotic resistance gene of plasmid pTEF1/Zeo (Invitrogen®). The PCR fragment was then cloned into pK20-2b-P/N-PmeI cut with Pst I and Not I to form the construct pK20-2b-X/N-Pme I (FIG. 5), containing a zeocin-resistant gene as a stuffer fragment flanked by unique Xho I and Not I sites.

Figure 6:
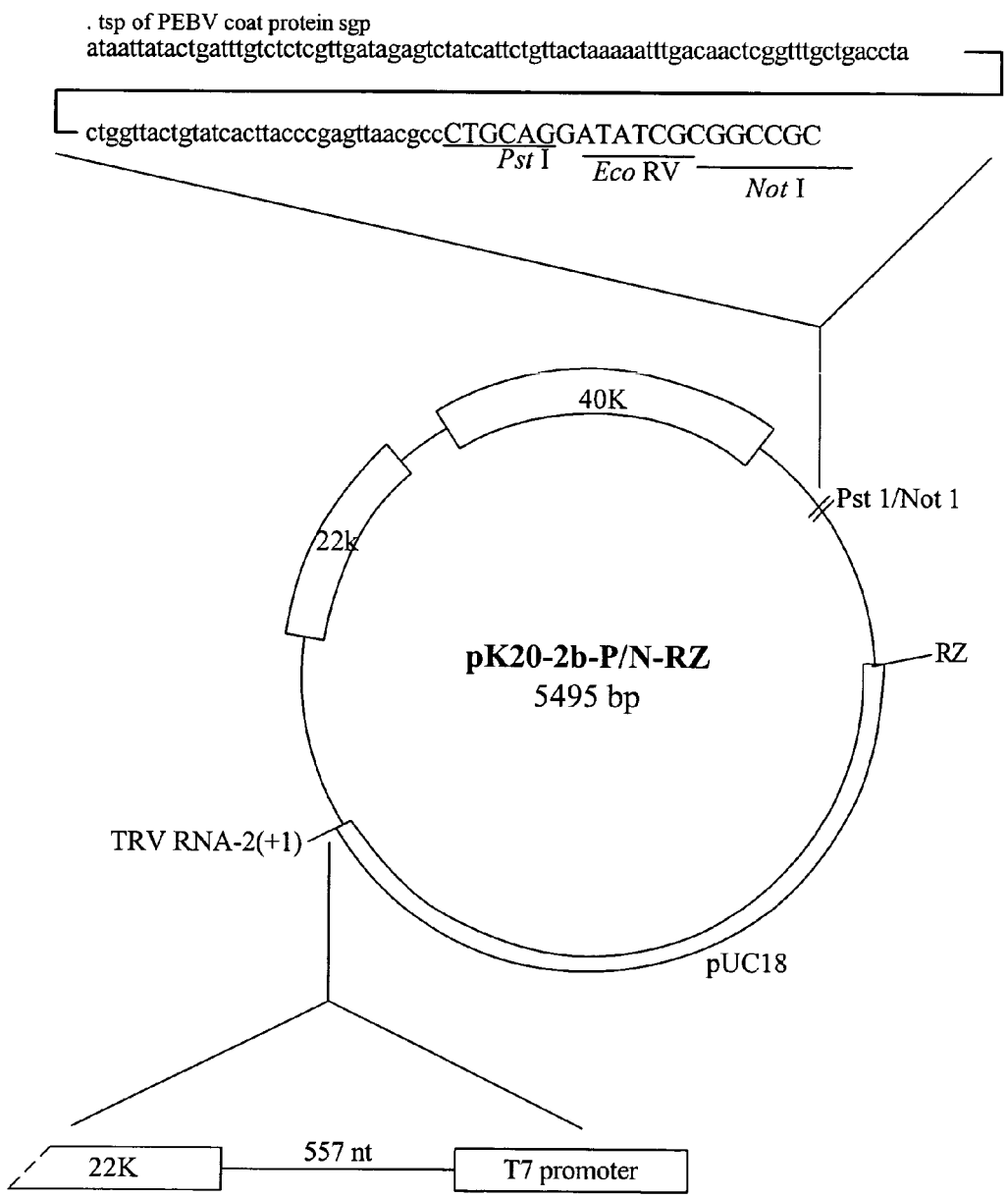
FIG. 6 depicts the plasmid pK20-2b-P/N-RZ. This plasmid contains the T7 promoter, the TRV RNA-2 22-, 40-kDa ORFs, the Pea Early Browning Virus (PEBV) subgenomic promoter, followed by the PstI and NotI restriction sites, a ribozyme for self-linearizing the plasmid during the transcription reaction, and part of the pUC18 plasmid. The transcriptional start point (tsp) of the subgenomic RNA from the PEBV coat promoter is indicated with a period (.) (SEQ ID NO: 2).

In addition, a self-cleaving ribozyme (RZ) site was introduced into pK20-2b-P/N-SmaI at the 3'-terminus of the TRV RNA-2 cDNA insert. This would preclude the necessity of linearizing the plasmid construct with a restriction enzyme prior to in vitro transcription (see below). Oligonucleotides 5'-AAGGAAAAAAGCGGCCGCGGTACC CCG-3' (upstream, TRVNOT4979-4995, SEQUENCE NO: 35) and 5'-GTTTAAACCCGGGCCCGTTTCG TCCTCACG-GACTCATCAGCCCGGAAAACACATC-CGGGGACGGGCGTAATA ACGTTACGTAG-3' (downstream, TRV23RZ, SEQUENCE ID NO: 36) were used to PCR amplify the region between the Not I and Sma I sites of pK20-2b-P/N-SmaI. The PCR fragment then was recloned into pK20-2b-P/N-SmaI cut with Not I and Sma I to form the construct pK20-2b-P/N-RZ (FIG. 6).

Construction of *N. benthamiana* Phytoene Desaturase Silencing Vector

Figure 8:
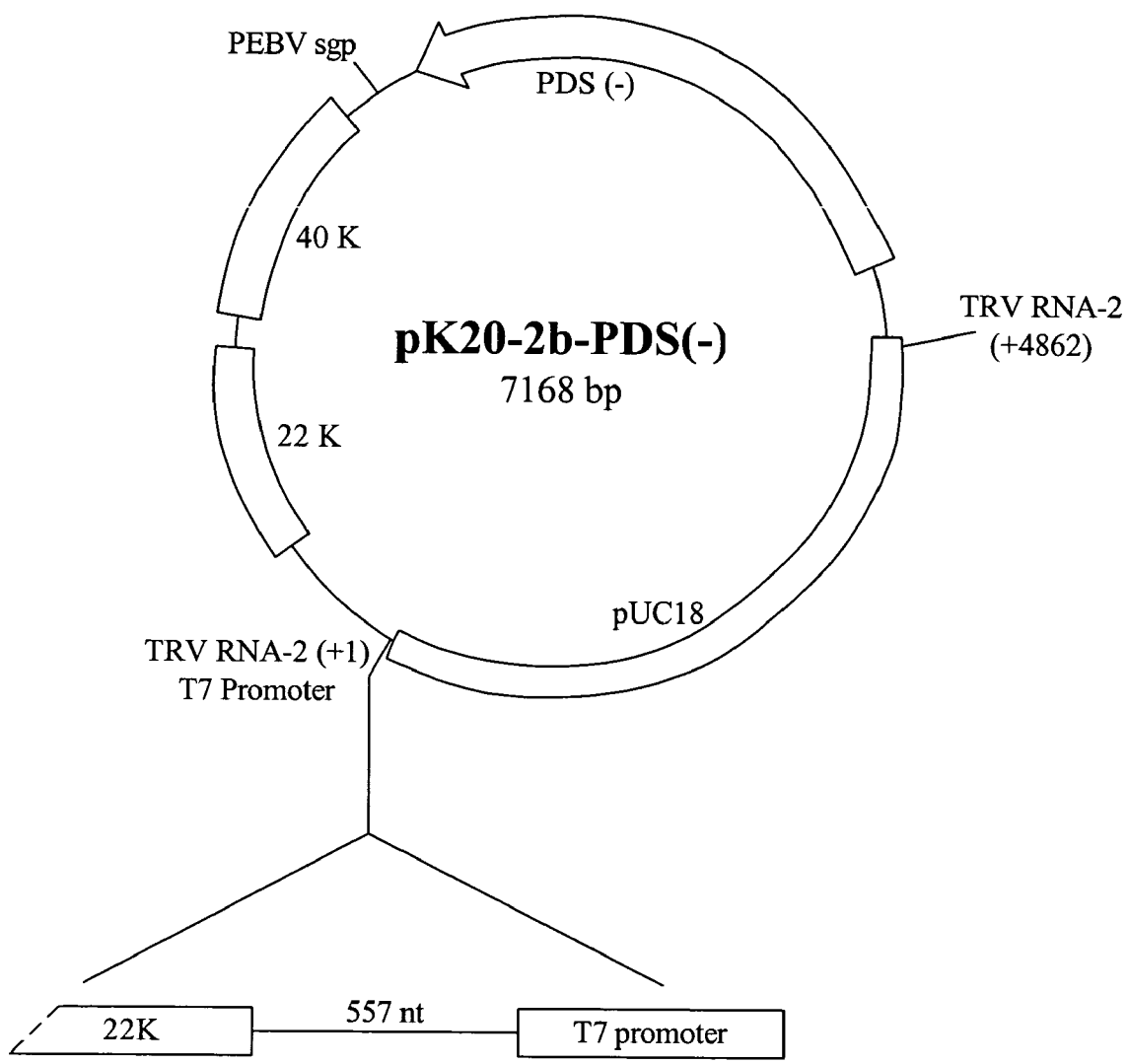
FIG. 8 depicts the plasmids pK20-2b-PDS(−). This plasmid contains the T7 promoter, the TRV RNA-2 22-, 40-kDa ORFs, the Pea Early Browning Virus (PEBV) subgenomic promoter, followed by the N. benthamiana Phytoene Desaturase ORF in the antisense orientation, a SmaI site for linearizing the plasmid prior to transcription, and part of the pUC18 plasmid. The transcriptional start point (tsp) of the subgenomic RNA from the PEBV coat promoter is indicated with a period (.).

A modified *N. benthamiana* phytoene desaturase cDNA containing unique Nsi I and Not I sites was PCR amplified from the plasmid pWPF187, which contains SEQ ID NO: 3 of U.S. Pat. No.5,539,093, Fitzmaurice, et al., 1996) using the following oligonucleotides 5'-TGGTTCTGCAGT TATG-CATGCCCCAAATTGGACTTG-3' (upstream, SEQ ID NO: 37) and 5'-TTTT CCTTTTGCGGCCGCTAAACTACGCT-TGCTTCTG-3' (downstream, SEQ ID NO: 38). The full-length phytoene desaturase cDNA was then subcloned into the Pst I/Not I sites of pK20-2b-P/N-SmaI in the positive orientation and the Not I/Pst I sites of pK20-2b-N/P-SmaI in the antisense orientation. The resulting constructs, pK20-2b-PDS(+)-SmaI (FIG. 7) and pK20-2b-PDS(−)-SmaI (FIG. 8), were linearized with Sma I and transcribed using T7 RNA polymerase (Ambion mMessage mMachine). Transcript RNA2 was mixed with transcripts from a full-length clone of TRV RNA-1 (pLSB-1).

Partial fragments of the PDS gene were also cloned into pK20-2b-P/N-SmaI. Oligonucleotides 5'-CGATAACCTG-CAGGATGCCCCAAATTGGACTTGTTTC-3' (upstream, Sse PDS 1 f, SEQUENCE ID NO: 39) and 5'-TGTGTAATG-GCGGCCG CAATATGTGCAACCCAG TCTCG-3' (downstream. Not PDS 500 r, SEQUENCE ID NO: 40) were used to PCR amplify the first 500 nucleotides of the *N. benthamiana* PDS gene and oligonucleotides 5'-CGATAACCTGCAGGA-CAG AAAACTGAAGAACACATCTG-3' (upstream, Sse PDS 1250 f, SEQUENCE ID NO: 41) and 5'-TGTGTAATG-GCGG CCGCCTAACTACGCTT GCTTCTGC-3' (downstream, Not PDS 1749 r, SEQUENCE ID NO: 42) were used to PCR amplify the last 500 nucleotides. The PCR fragments were then subcloned into the Pst I/Not I sites of pk20-2b-P/N-SmaI in the positive orientation. The resulting constructs, pK20-2b-5'PDS(+) and pK20-2b-3'PDS(+), were linearized, transcribed, and mixed with RNA-1 as described above.

Analysis of *N. benthamiana* Transfected by TRV-PDS

Infectious transcripts of TRV RNA-1 (pLSB-1) were individually mixed with transcripts from pK20-2b-PDS(+), pK20-2b-PDS(−), pK20-2b-5'PDS(+), and pK20-2b3The mixtures, designated TRV-2b-PDS(+), TRV-2b-PDS(−), TRV-2b-5'PDS(+), and TRV-2b-3'PDS(−), respectively, were used to mechanically inoculate *N. benthamiana*. Extracts from infected plants were ground in 25 mM NaPO$_4$/1% celite (pH7.2) and passaged onto *Chenopodium amaranticolor*, a local lesion host of TRV. This local lesion infectivity assay verified that the hybrid viruses spread throughout all the non-inoculated upper leaves. The viral symptoms resulting from the infection consisted of distortion of systemic leaves and plant stunting2 with mild chlorosis. Approximately 6-7 days after transfection, chlorotic areas began to develop in the upper emerging leaves. After 8-10 days, these chlorotic areas bleached white. There was no significant difference in the development and appearance of symptoms whether the PDS gene was in the positive or negative orientation, or whether the full-length or partial fragments of PDS were used. The systemically infected leaves from plants transfected with TRV-2b-PDS(+) containing the full-length PDS gene was shown to accumulate high levels of phytoene (Table 1).

Analysis of Arabidopsis Transfected with TRV-GFP and TRV-PDS

Extracts from *N. benthamiana* infected with TRV-2b-GFP were ground in 25 mM NaPO$_4$/1% celite and passaged onto Arabidopsis. After 5-7 days, systemic expression of GFP was observed. However, the GFP fluorescence begins to visibly fade after 10-13 days; after 14 days, GFP fluorescence was no longer visibly detected. This observation suggests that GFP expression by TRV was reduced in Arabidopsis after an initial phase of overexpression.

Extracts from *N. benthamiana* infected with TRV-2b-PDS (+) were ground in 25 mM NaPO$_4$/1% celite and passaged onto Arabidopsis. After 7-11 days, TRV-2b-PDS(+) induced the production of white bleached leaves in the systemic leaves, illustrating silencing of PDS gene expression.

Purification and Analysis of Carotenoids from Transfected Plants

The carotenoids were isolated from systemically infected tissue and analyzed by HPLC, GC-MS, and UV spectrum HPLC chromatography. Carotenoids were extracted in methanol and identified by their peak retention time and absorption spectra on a 5-cm Jupiter Silica C-18 analytical column using acetonitrile/methanol/2-propanol (85:10:5) as a developing solvent at a flow rate of 0.5 m/min. Phytoene from plant extracts had an identical retention time to a phytoene standard. The GC-MS spectrum of the phytoene standard matched that of the Wiley 275.L database. The phytoene peak from N. benthamiana transfected with TRV-2b-PDS(+) had an optical absorbence maxima at 285 nm, with shoulders at 276 and 298 nm. Plants transfected with TRV-2b-PDS(+) showed a sixteen-fold increase in phytoene compared to the levels in noninfected plants. Since the colored carotenoids protect chlorophyll from photooxidation, the viral derived cytoplasmic inhibition of phytoene desaturase caused the systemically infected leaves to turn white. This phenotype was also observed in plants that were treated with the herbicide norflurazon, a phytoene desaturase inhibitor. HPLC analysis of norflurazon treated plants revealed that they also accumulated phytoene. Similar data of cytoplasmic inhibition of phytoene desaturase in N. benthamiana plants transfected with the tobamoviral vector TTO1A PDS+ was presented by Kumagai. et al., Proc. Natl. Acad. Sci. USA 92:1679-1683 (1995).

Example 2

Figure 9:
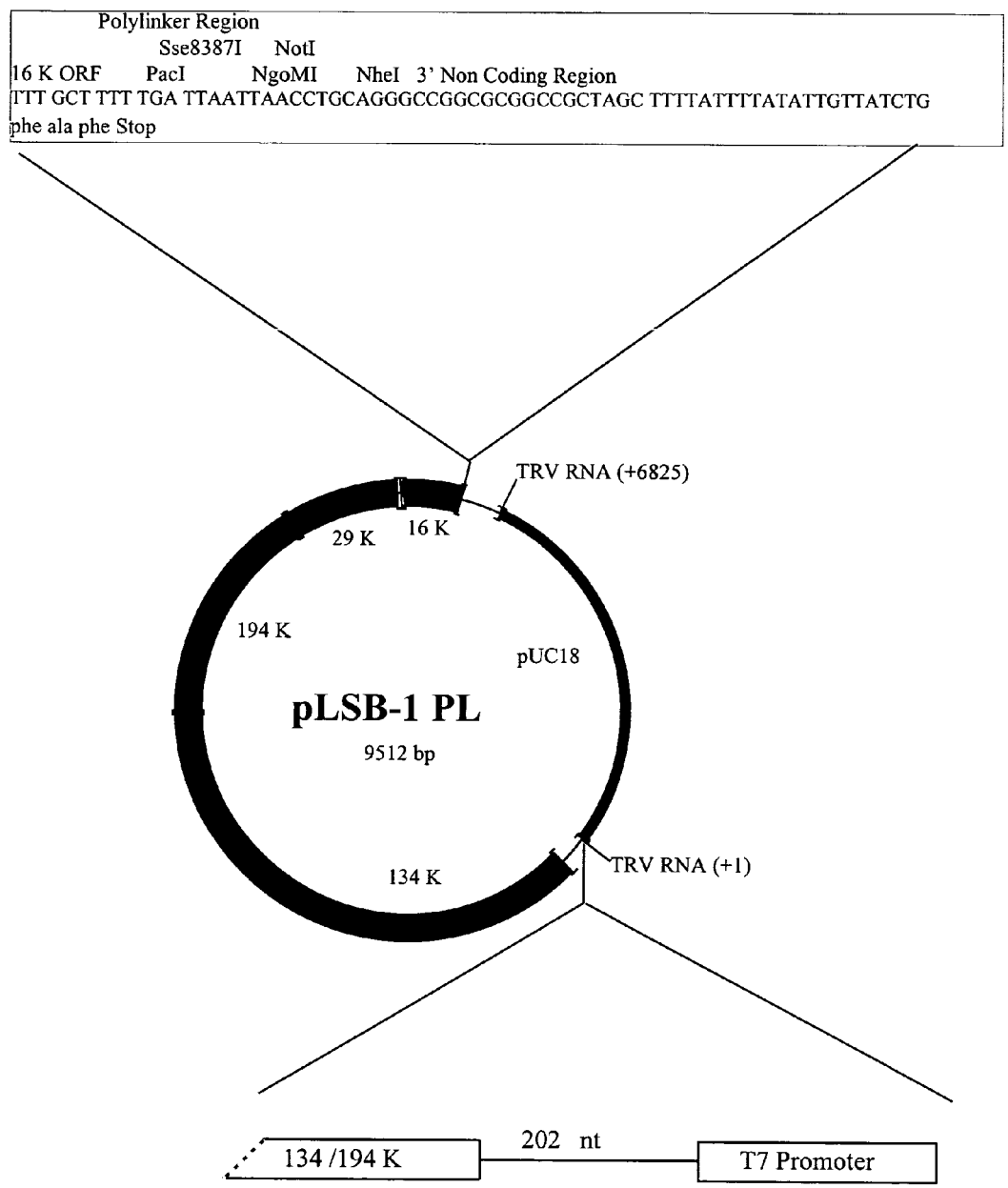
FIG. 9 depicts the plasmid pLSB-1 PL. This plasmid contains the T7 promoter, the TRV RNA-1 134-, 194-, 29-, 16-kDa ORFs, multiple cloning sites PacI, Sse8387I, NotI, NgoMI and NheI, and part of the pUC18 plasmid. (SEQ ID NO: 6).

Development of an RNA-1 Modified Tobraviral Vector for Cytoplamic Inhibition of Gene Expression in Transfected Plants The first step to making the monopartite silencing system was to insert a polylinker into pLSB-1. The polylinker was inserted at the 3' end of the CRP by splice overlap PCR (Horton, R. M. Hunt, et al., Gene 77:61-8s (1989)). A 1594 bp fragment from the Afl II site (at 5401 in pLSB-1) to the polylinker region at the 3' end of CRP was amplified using the oligonucleotides 5'-AAGTTCTTGCTTAAGACGTCATCG-3' (upstream) (o33, SEQ ID NO: 43) and 5'-GCCGGCCCT-GCAGGTTAATTAATCAAAAAGCAAA-CAAACGATCAATC-3' (downstream) (o37, SEQ ID NO: 44). A 359 bp fragment from polylinker region at the 3' end of CRP to downstream of the BamHI site (at 7221 in pLSB-1) was amplified using the oligonucleotides 5'-TTAATTAAC-CTGCAGGGCCGGCGCGGCCGCTAGCTTTTA TTT-TATATTGTTATCTGTTTCTG-3' (upstream) (o38, SEQ ID NO: 45), and 5'-CGGATAACAATTTCACACAGGA-3' (downstream) (30B 7792 R, SEQ ID NO: 46). Biology) and cleaned up using a Strataprep spin column (Stratagene), then joined together using the oligonucleotides 5'-AAGTTCT-TGCTTAAGACGTCATCG-3' (upstream) (o33, SEQ ID NO: 47) and 5'-CGGATAACAATTTCACACAGGA-3' (downstream) (30B 7792 R, SEQ ID NO: 48). The splice overlap PCR product was subcloned into pLSB-1 at AflII/BamHI, creating pLSB-1 PL (FIG. 9). The polylinker region of pLSB-1 PL was verified by DNA sequencing. When N. benthamiana plants were coinoculated with pLSB-1 PL and either TRV-2b-PDS or TRV-2b-GFP, there was little discernible difference in the symptoms displayed by the plant hosts compared to plants coinoculated with the parental construct pLSB-1 and either TRV-2b-PDS or TRV-2b-GFP.

Figure 10:
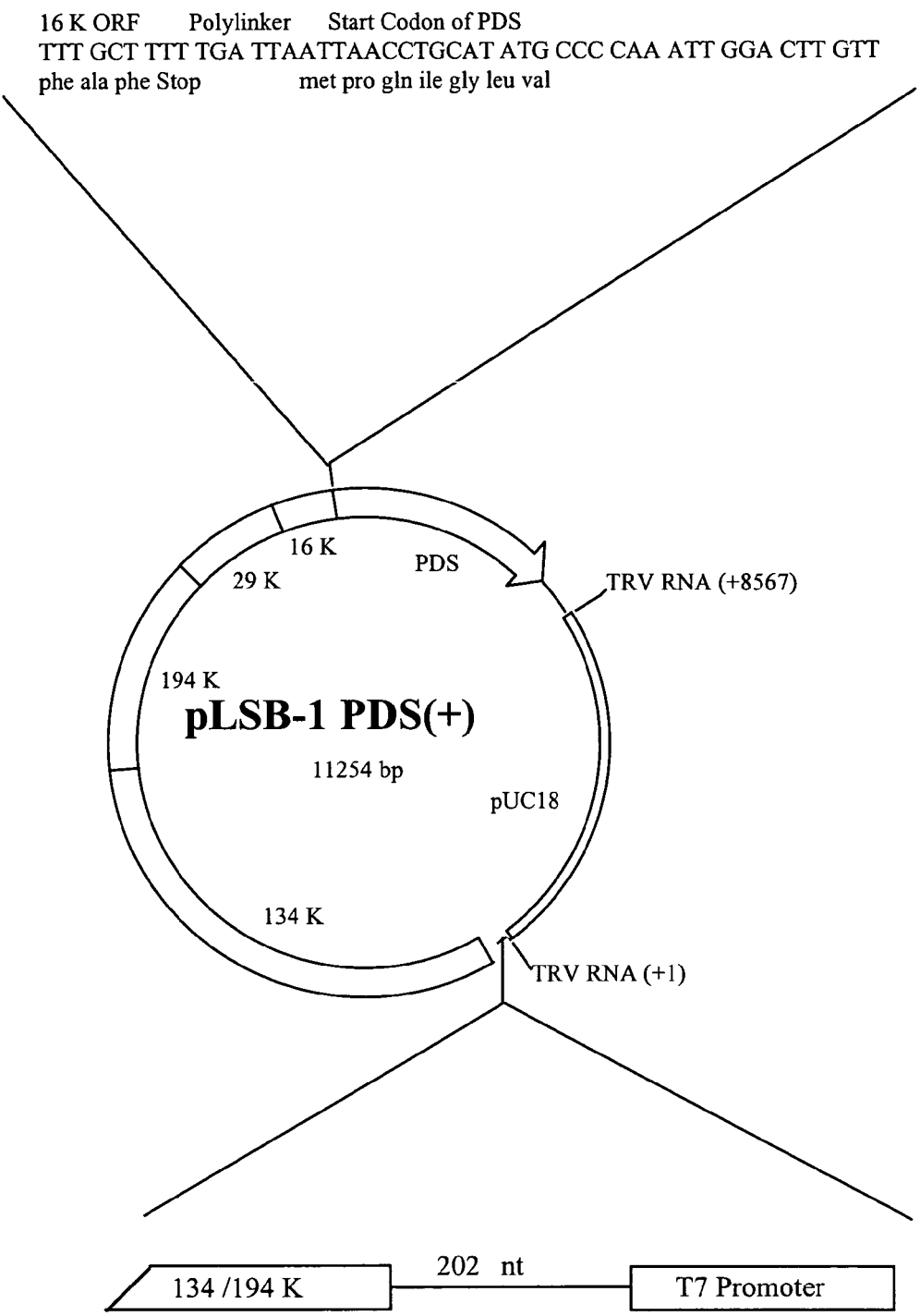
FIG. 10 depicts the plasmid pLSB-1 PDS(+). This plasmid contains the T7 promoter, the TRV RNA-1 134-, 194-, 29-, 16-kDa ORFs, the N. benthamiana Phytoene Desaturase ORF in the sense orientation, and part of the pUC18 plasmid. (SEQ ID. NOS. 7 and 8).

The next step to making a monopartite silencing vector was to insert a plant gene to silence into pLSB-1 PL at the polylinker region. Phytoene desaturase (PDS) was chosen for its distinctive visual phenotype when expression of this gene is knocked out due to viral induced gene silencing. The N. benthamiana PDS allele 2 cDNA was PCR amplified from the plasmid pWPF187 containing this PDS gene (U.S. Pat. No. 5,539,093, Fitzmaurice et al., 1996) using the following oligonucleotides 5'- TGGTTCTGCAGTTATGCATGC-CCCAAA TTGGACTTG-3' (upstream) (SEQ ID NO: 49) and 5'- TTTTCCTTTTGCGGCCGCTAA ACTACGCT-TGCTTCTG-3' (downstream) (SEQ ID NO: 50). The 5' overhangs of these oligonucleotides contain unique Nsi I and Not I sites, which were incorporated upstream and downstream, respectively, of the PDS gene. The phytoene desaturase cDNA was then subcloned into the Sse 8387 I/Not I sites of pLSB-1 PL to make pLSB-1 PDS (+) (FIG. 10). Note that Sse 8387 I (Amersham Pharmacia Biotech Inc., Piscataway, NJ 08855) and Nsi I produce compatible cohesive ends.

Example 3

Development of a Monopartite Tobraviral Vector for Cytoplamic Inhibition of Gene Expression in Transfected Plants DNA template for RNA transcription was made by digesting the plasmid pLSB-1 PDS (+) with SmaI to linearize it at the 3' end of the virus. Infectious RNA transcripts were made using components of the mMessage mMachine large scale in vitro transcription kit (Ambion Inc., Austin Tex. 78744) in a total volume of 4.3 µl. RNA-1 template transcriptions were done using 0.4 µl 10× Transcription Buffer, 2.0 µl 2× Ribonucleotide Mix, 0.2 µl 30 mM GTP, 1.3 µl DNA template (at roughly 100 ng/µl concentration), and 0.4 µl T7 RNA polymerase enzyme mix. The mixture was inculated 1 to 2 hours at 37° C., then used to inoculate N. benthamiana plants as follows. The RNA transcripts were mixed with 50 µl FES (7.5 g/L glycine, 10.5 g/L dibasic potassium phosphate, 10 g/L sodium pyrophosphate, 10 g/L bentonite, 10 g/L celite), then pipetted on the top surface of two opposite leaves of the plant. Transcript RNA was manually rubbed into the leaves. Inoculated plants were maintained in an indoor greenhouse.

Figure 11:
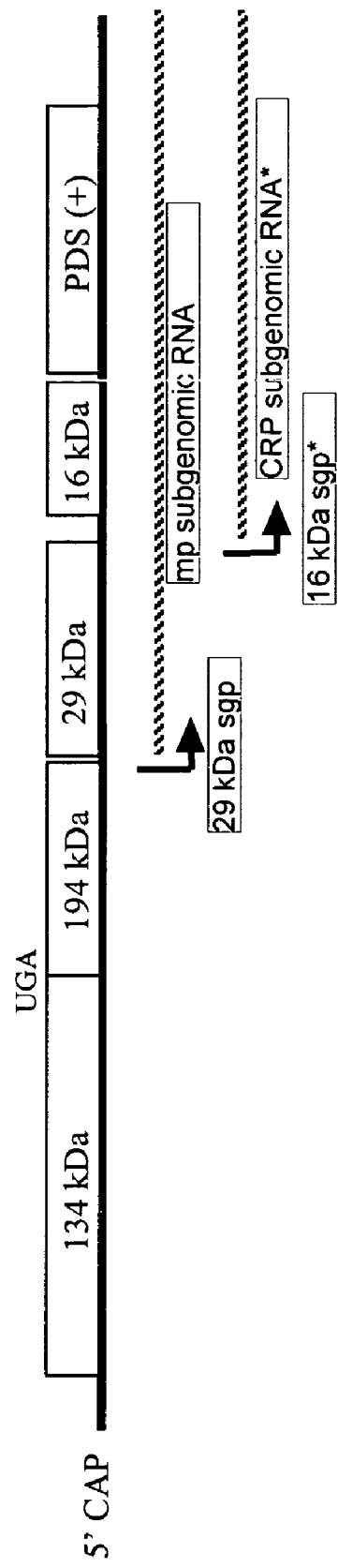
FIG. 11 depicts the putative subgenomic promoters in the tobraviral vector LSB-1 PDS(+).

When N. benthamiana plants were inoculated with the RNA-1 pLSB-1 PDS(+) alone, there was bleaching of systemic leaves, starting at 2-2.5 weeks post inoculation. Thus pLSB-1 PDS (+) is acting as a monopartite silencing vector. Unlike previous viral vectors that were developed for gene silencing in plants, this construct does not contain an additional subgenomic promoter. The phytoene desaturase inhibitor RNA is expressed on a subgenomic RNA that is operationally linked to the endogenous CRP RNA (FIG. 11).

Example 4

Development of a Multifunctional Heterologous Gene Expression/Silencing Tobraviral Vector Being able to simultanously silence one gene in TRV RNA-1 and overexpress or silence others in TRV RNA-2 would provide several benefits. It would greatly expand the number of biological products that could be produced in plants.

To coinoculate plants with both RNA-1 and RNA-2, transcription reactions were set up as indicated in Example 4, with the following differences. The 4.3 µl RNA-2 transcription reaction was set up without added GTP, using 0.4 µl 10×

Transcription Buffer, 2.0 µl 2× Ribonucleotide Mix, 0.2 µl water, 1.3 µl DNA template (at roughly 100 ng/µl concentration), and 0.4 µl T7 RNA polymerase enzyme mix. 4.3 µl RNA-1 transcripts and 4.3 µl RNA-2 transcripts were mixed together, then with 50 µl FES and pipetted to plant leaves as indicated in Example 3.

When *N. benthamiana* plants were coinoculated with pLSB-1 PDS (+) and TRV-2b-GFP, there was a delay of about two days in GFP expression and bleaching of systemic leaves due to PDS silencing compared to coinoculation with pLSB-1 and TRV-2b-GFP. There was simultaneous expression of GFP and silencing of PDS on the same systemic leaves by 8 days post inoculation. This indicated that the two RNAs of TRV could be used in a dual gene expression/silencing vector system. When *N. benthamiana* plants were coinoculated with the RNA-1 construct pLSB-1 PDS(+), and the RNA-2 construct pK20-2b-PDS(+), there was no delay in PDS silencing.

Example 5

*Arabidopsis thaliana* cDNA Library Construction in a Dual Subgenomic Promoter Vector

*Arabidopsis thaliana* cDNA libraries obtained from the Arabidopsis Biological Resource Center (ABRC). The four libraries from ABRC were size-fractionated to inserts of 0.5-1 kb (CD4-13), 1-2 kb (CD4-14), 2-3 kb (CD4-15), and 3-6 kb (CD4-16). All libraries are of high quality and have been used by several dozen groups to isolate genes. The pBluescript® phagemids from the Lambda ZAP II vector were subjected to mass excision and the libraries were recovered as plasmids according to standard procedures.

Figure 12:
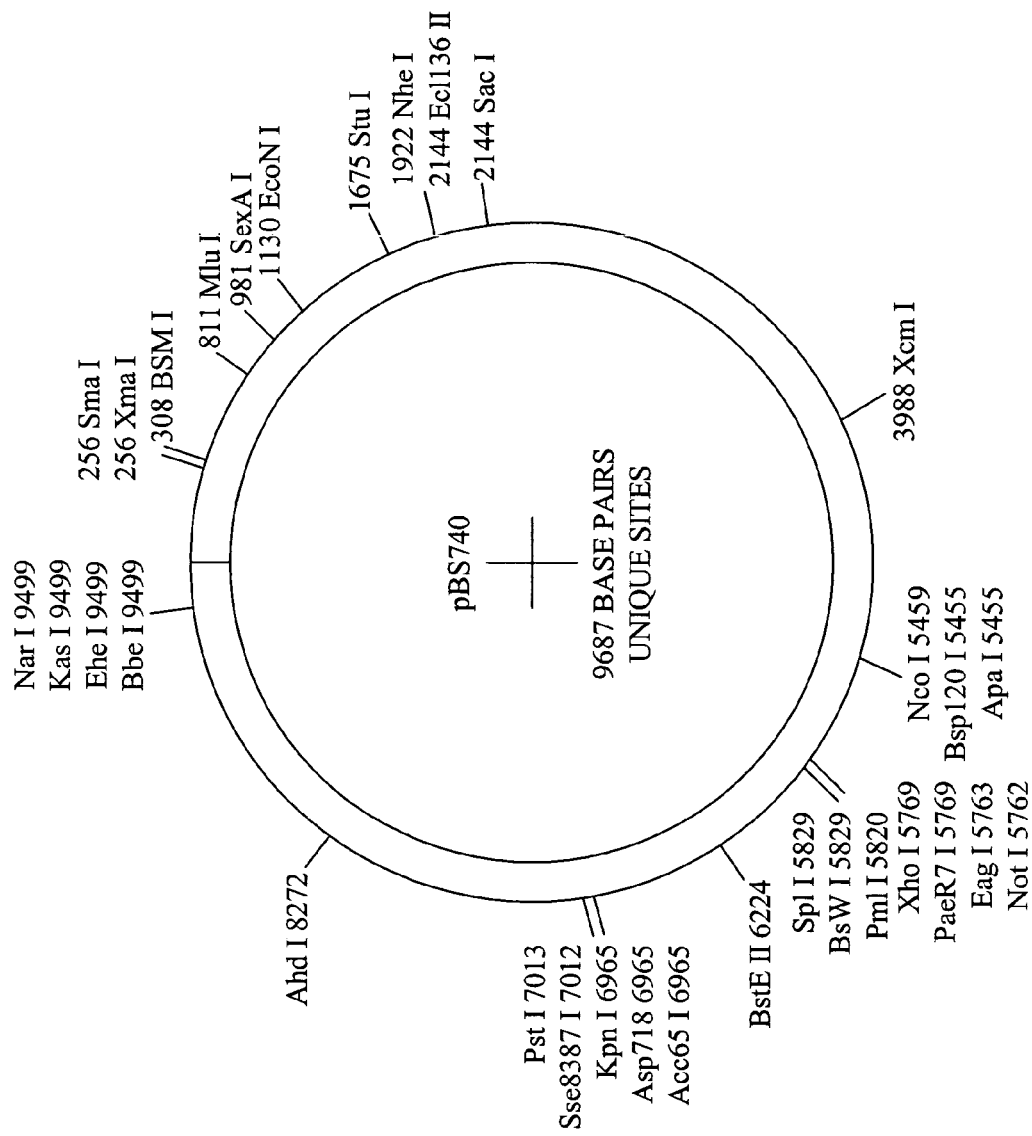
FIG. 12 depicts the plasmid pBS740.

Alternatively, the cDNA inserts in the CD4-13 (Lambda ZAP II vector) were recovered by digestion with NotI. Digestion with NotI in most cases liberated the entire *Arabidopsis thaliana* cDNA insert because the original library was assembled with NotI adapters. NotI is an 8-base cutter that infrequently cleaves plant DNA. In order to insert the NotI fragments into a transcription plasmid, the pBS735 transcription plasmid was digested with PacI/XhoI and ligated to an adapter DNA sequence created from the oligonucleotides 5'-TCGAGCGGCCGCAT-3' (SEQ ID NO: 51) and 5'-GCG-GCCGC-3'. The resulting plasmid pBS740 (FIG. 12) contains a unique NotI restriction site for bi-directional insertion of NotI fragments from the CD4-13 library. Recovered colonies were prepared from these for plasmid minipreps with a Qiagen BioRobot 9600®. The plasmid DNA preps performed on the BioRobot 9600® were done in 96-well format and yield transcription quality DNA. An Arabidopsis cDNA library was transformed into the plasmid and analyzed by agarose gel electrophoresis to identify clones with inserts. Clones with inserts were transcribed in vitro and inoculated onto *N. benthamiana* or *Arabidopsis thaliana*. Selected leaf disks from transfected plants were then taken for biochemical analysis.

Example 6

Identification of Nucleotide Sequences Involved in the Regulation of Plant Growth by Cytoplasmic Inhibition of Gene Expression in an Antisense Orientation Using Viral Derived RNA (GTP Binding Proteins)

In this example, we show: (1) a method for producing antisense RNA using an RNA viral vector, (2) a method to produce viral-derived antisense RNA in the cytoplasm, (3) a method to inhibit the expression of endogenous plant proteins in the cytoplasm by viral antisense RNA, and (4) a method to produce transfected plants containing viral antisense RNA, such method is much faster than the time required to obtain genetically engineered antisense transgenic plants. Systemic infection and expression of viral antisense RNA occurs as short as several days post inoculation, whereas it takes several months or longer to create a single transgenic plant. This example demonstrates that novel positive strand viral vectors, which replicate in the cytoplasm, can be used to identify genes involved in the regulation of plant growth by inhibiting the expression of specific endogenous genes. This example enables one to characterize specific genes and biochemical pathways in transfected plants using an RNA viral vector.

Figure 13:
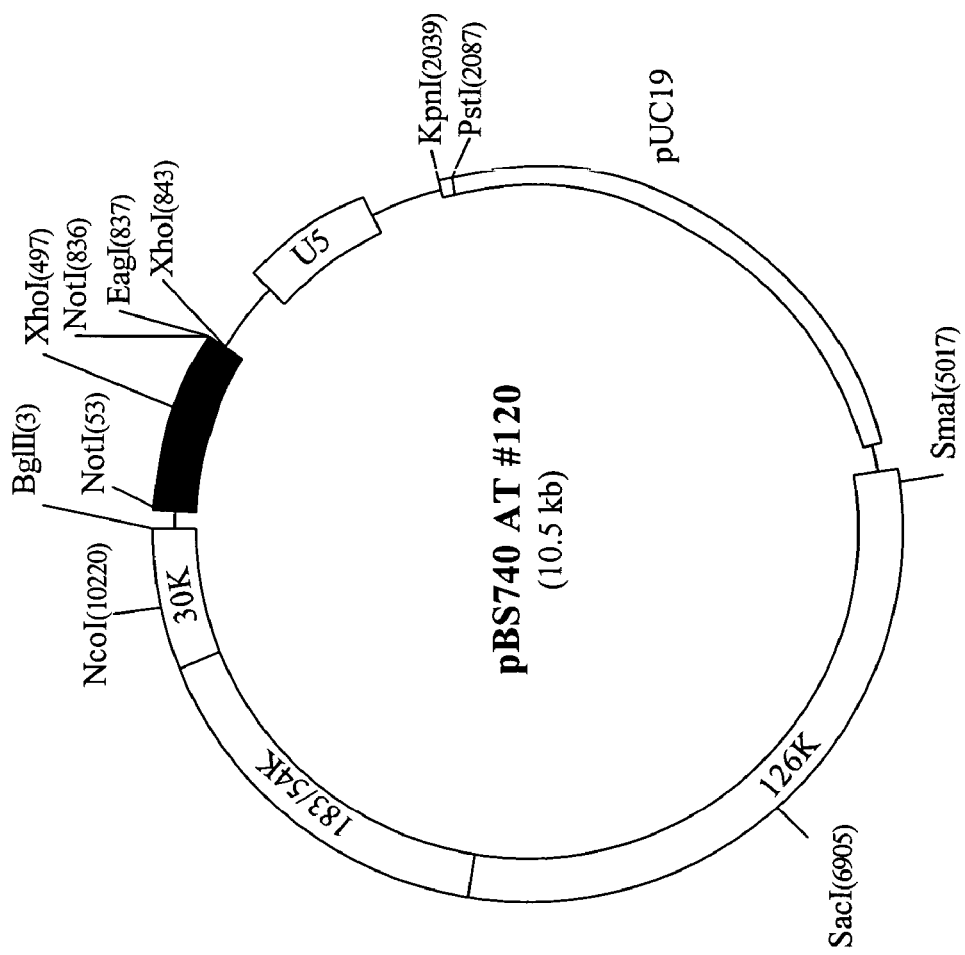
FIG. 13 depicts the plasmid 740 AT #120.

Tobamoviral vectors have been developed for the heterologous expression of uncharacterized nucleotide sequences in transfected plants. A partial *Arabidopsis thaliana* cDNA library was placed under the transcriptional control of a tobamovirus subgenomic promoter in a RNA viral vector. Colonies from transformed *E. coli* were automatically picked using a Flexys robot and transferred to a 96 well flat bottom block containing terrific broth (TB) Amp 50 µg/ml. Approximately 2000 plasmid DNAs were isolated from overnight cultures using a BioRobot and infectious RNAs from 430 independent clones were directly applied to plants. One to two weeks after inoculation, transfected *Nicotiana benthamiana* plants were visually monitored for changes in growth rates, morphology, and color. One set of plants transfected with 740 AT #120 (FIG. 13) were severely stunted. DNA sequence analysis revealed that this clone contained an Arabidopsis GTP binding protein open reading frame (ORF) in the antisense orientation. This demonstrates that an episomal RNA viral vector can be used to deliberately alter the metabolic pathway and cause plant stunting. In addition, our results suggest that the Arabidopsis antisense transcript can turn off the expression of the *N. benthamiana* gene.

Construction of an *Arabidopsis thaliana* cDNA Library in an RNA Viral Vector

An *Arabidopsis thaliana* CD4-13 cDNA library was digested with NotI. DNA fragments between 500 and 1000 bp were isolated by trough elution and subcloned into the NotI site of pBS740. *E. coli* C600 competent cells were transformed with the pBS740 AT library and colonies containing Arabidopsis cDNA sequences were selected on LB Amp 50 µg/ml. Recombinant C600 cells were automatically picked using a Flexys robot and then transferred to a 96 well flat bottom block containing terrific broth (TB) Amp 50 µg/ml. Approximately 2000 plasmid DNAs were isolated from overnight cultures using a BioRobot (Qiagen) and infectious RNAs from 430 independent clones were directly applied to plants.

Isolation of a Gene Encoding a GTP Binding Protein

One to two weeks after inoculation, transfected *Nicotiana benthamiana* plants were visually monitored for changes in growth rates, morphology, and color. Plants transfected with 740 AT #120 were severely stunted. Plasmid 740 AT #120 contains the TMV-U1 126-, 183-, and 30-kDa ORFs, the TMV-U5 coat protein gene (U5 cp), the T7 promoter, an *Arabidopsis thaliana* CD4-13 NotI fragment, and part of the pUC19 plasmid. The TMV-U1 subgenomic promoter located within the minus strand of the 30-kDa ORF controls the synthesis of the CD4-13 antisense subgenomic RNA.

DNA Sequencing and Computer Analysis

A 782 bp NotI fragment of 740 AT #120 containing the ADP-ribosylation factor (ARF) cDNA was characterized. DNA sequence of NotI fragment of 740 AT #120 (774 base pairs) is as follows:

(SEQ ID NO: 52)
```
5'-CCGAAACATTCTTCGTAGTGAAGCAAAATGGGGTTGAGTTTCGCCAA
GCTGTTTAGCAGGCTTTTTGCCAAGAAGGAGATGCGAATTCTGATGGTTG
GTCTTGATGCTGCTGGTAAGACCACAATCTTGTACAAGCTCAAGCTCGGA
GAGATTGTCACCACCATCCCTACTATTGGTTTCAATGTGGAAACTGTGGA
ATACAAGAACATTAGTTTCACCGTGTGGGATGTCGGGGGTCAGGACAAGA
TCCGTCCCTTGTGAGACACTACTTCCAGAACACTCAAGGTCTAATCTTTG
TTGTTGATAGCAATGACAGAGACAGAGTTGTTGAGGCTCGAGATGAACTC
CACAGGATGCTGAATGAGGACGAGCTGCGTGATGCTGTGTTGCTTGTGTT
TGCCAACAAGCAAGATCTTCCAAATGCTATGAACGCTGCTGAAATCACAG
ATAAGCTTGGCCTTCACTCCCTCCGTCAGCGTCATTGGTATATCCAGAGC
ACATGTGCCACTTCAGGTGAAGGGCTTTATGAAGGTCTGGACTGGCTCTC
CAACAACATCGCTGGCAAGGCATGATGAGGGAGAAATTGCGTTGCATCGA
GATGATTCTGTCTGCTGTGTTGGGATCTCTCTCTGTCTTGATGCAAGAGA
GATTATAAATATTATCTGAACCTTTTTGCTTTTTTGGGTATGTGAATGTT
TCTTATTGTGCAAGTAGATGGTCTTGTACCTAAAAATTTACTAGAAGAAC
CCTTTTAAATAGCTTTCGTGTATTGT-3'.
```

The nucleotide sequencing of 740 AT #120 was carried out by dideoxy termination using double stranded templates. Nucleotide sequence analysis and amino acid sequence comparisons were performed using DNA Strider, PCGENE and NCBI Blast programs. 740 AT #120 contained an open reading frame (ORF) in the antisense orientation that encodes a protein of 181 amino acids with an apparent molecular weight of 20,579 Daltons.

Sequence Comparison

FIG. 14 shows a nucleotide sequence comparison of *A. thaliana* 740 AT #120 and *A. thaliana* est AA042085 (SEQ ID NOs: 9 and 10 respectively). The nucleotide sequence from 740 AT #120 is also compared with a rice (*Oryza sativa*) ADP ribosylation factor D17760, SEQ ID NOs: 11 and 12 (FIG. 15); which shows 82% (456/550) positives and identities.

The nucleotide sequence from 740 AT #120 exhibits a high degree of homology (81-84% identity and positive) to rice, barley, carrot, corn and *A. thaliana* DNA encoding2 ARFs; and also a high degree of homology (71-87% identity and positive) to yeast, plants, insects such as fly, amphibian such as frog, mammalian such as bovine, human, and mouse DNA encoding ARFs (Table 2).

The amino acid sequence derived from 740 AT #120 exhibits an even higher degree of homology (96-98% identity and 97-98% positive) to ARFs from rice, carrot, corn and *A. thaliana* and a high degree of homology (61-98% identity and 78-98% positive; higher than nucleotide sequence homology) to ARFs from yeast, plants, insects such as fly, mammalian such as bovine, human, and mouse (Table 3).

The high homology of DNAs encoding GTP binding proteins from yeast, plants, insects, human, mice, and amphibians indicates that DNAs from one donor organism can be transfected into another host organism and silence the endogenous gene of the host organism.

TABLE 2

740 AT #120 Nucleotide Sequence Comparison

| | Score | Expect | Identities | Positives |
|---|---|---|---|---|
| barley E10542 | 540.8 bits (1957) | 1.4e−157 | 461/548 (84%) | 461/548 (84%) |
| *A. thaliana* M95166 | 538.5 bits (1949) | 7.4e−157 | 461/550 (83%) | 461/550 (83%) |
| rice AF012896 | 537.7 bits (1946) | 1.3e−156 | 462/553 (83%) | 462/553 (83%) |
| carrot D45420 | 531.4 bits (1923) | 9.8e−155 | 471/579 (81%) | 471/579 (81%) |
| corn X80042 | 512.3 bits (1854) | 6.8e−149 | 450/549 (81%) | 450/549 (81%) |
| *C. reinhardtii* U27120 | 480.0 bits (1740) | 1.6e−139 | 436/546 (79%) | 436/546 (79%) |
| mouse brain ARF3 D87900 | 431.1 bits (1560) | 1.7e−124 | 416/546 (76%) | 416/546 (76%) |
| Bovine J03794 | 426.9 bits (1545) | 3.6e−123 | 409/534 (76%) | 409/534 (76%) |
| Human ARF3 M33384 | 433.5 bits (1569) | 4.9e−123 | 417/546 (76%) | 417/546 (76%) |
| *S. pombe* ARF1 L09551 | 430.2 bits (1557) | 1.1e−121 | 409/531 (77%) | 409/531 (77%) |
| Human ARF1 AF05502 | 428 bits (1549) | 5.8e−121 | 405/524 (77%) | 405/524 (77%) |
| frog U31350 | 414.5 bits (1500) | 1.7e−119 | 412/552 (74%) | 412/552 (74%) |
| Human ARF5 M57567 | 387.4 bits (1402) | 1.0e−107 | 390/527 (74%) | 390/527 (74%) |
| *S. cerevisiae* J03276 | 362.8 bits (1313) | 1.6e−99 | 381/529 (72%) | 381/529 (72%) |
| Human ARF4 M36341 | 358.4 bits (1297) | 4.3e−98 | 377/524 (71%) | 377/524 (71%) |
| *C. elegans* M36341 | 149.8 bits (542) | 2.0e−90 | 154/211 (72%) | 154/211 (72%) |
| *N. tabacum* NTGB1 U46927 | 285.7 bits (1034) | 4.8e−78 | 234/268 (87%) | 234/268 (87%) |
| Human cosmid AC000357 | 107.5 bits (389) | 9.7e−73 | 93/112 (83%) | 93/112 (83%) |
| fly S62079 | 211.9 bits (767) | 2.8e−72 | 195/247 (78%) | 195/247 (78%) |

TABLE 3

Amino acid sequence comparison of 740 AT #120 with ARFs from other organisms.

| | Score | Expect | Identities | Positives |
|---|---|---|---|---|
| *A. thaliana* ARF1 g543841 | 365 bits (928) | e−101 | 179/181 (98%) | 179/181 (98%) |
| rice g1703380 | 363 bits (921) | e−100 | 177/181 (97%) | 179/181 (98%) |
| corn g1351974 | 356 bits (905) | 3e−98 | 174/181 (96%) | 179/181 (98%) |
| carrot g1703375 | 362 bits (919) | e−100 | 177/181 (97%) | 178/181 (97%) |

TABLE 3-continued

Amino acid sequence comparison of
740 AT #120 with ARFs from other organisms.

|  | Score | Expect | Identities | Positives |
|---|---|---|---|---|
| C. reinhardtii g1703374 | 354 bits (898) | 2e−97 | 172/180 (95%) | 174/180 (96%) |
| Bovine | 327 bits (829) | 2e−89 | 160/177 (90%) | 166/177 (93%) |
| Human ARF1 | 326 bits (827) | 4e−89 | 160/177 (90%) | 166/177 (93%) |
| mouse | 326 bits (827) | 4e−89 | 160/177 (90%) | 166/177 (93%) |
| fly | 325 bits (825) | 7e−89 | 158/177 (89%) | 166/177 (93%) |
| Human ARF3 P16587 | 321 bits (813) | 1e−87 | 157/180 (87%) | 164/180 (90%) |
| Human ARF5 g114127 | 305 bits (774) | 7e−83 | 145/178 (81%) | 161/178 (89%) |
| Human ARF4 g114123 | 304 bits (770) | 2e−82 | 145/178 (81%) | 160/178 (89%) |
| yeast ARF1 g171072 | 298 bits (754) | 2e−80 | 139/177 (78%) | 161/177 (90%) |
| A. thaliana ARF3 | 241 bits (608) | 2e−63 | 109/177 (61%) | 140/177 (78%) |

The protein encoded by 740 AT #120, 120P, contained three conserved domains: the phosphate binding loop motif, GLDAAGKT SEQUENCE ID NO: 53, (consensus GXXXXGKS/T); the G' motif. DVGGQ, SEQUENCE ID NO: 54 (consensus DXXGQ), a sequence which interacts with the gamma-phosphate of GTP; and the G motif NKQD (consensus NKXD), which is specific for guanidinyl binding. The 120 P contains a putative glycine-myristoylation site at position 2, a potential N-glycosylation site (NXS) at position 60, and several putative serine/threonine phosphorylations sites.

Isolation of an *Arabidopsis thaliana* ARF Genomic Clone

Figure 16:
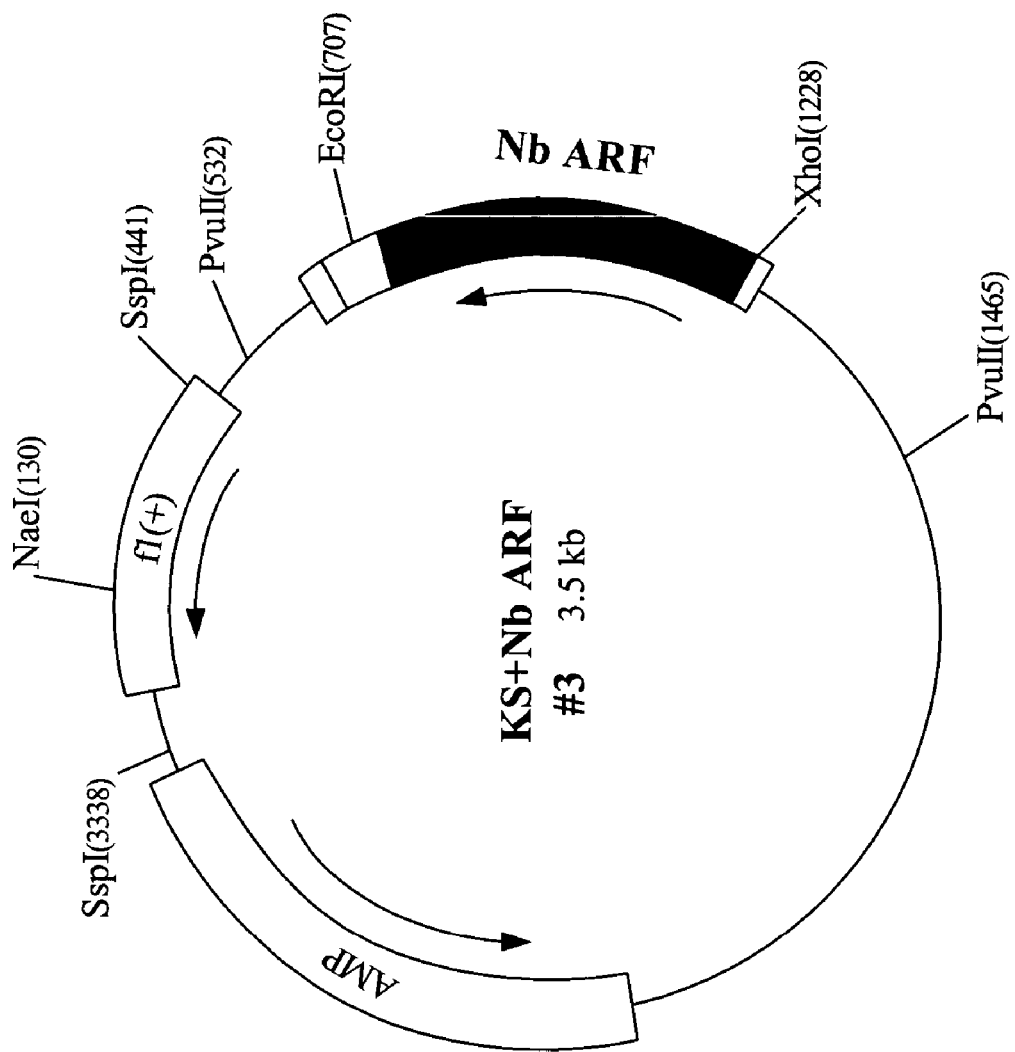
FIG. 16 depicts the plasmid KS+Nb ARF #3.

A genomic clone encoding *A. thaliana* ARF can be isolated by probing filters containing *A. thaliana* BAC clones using a $^{32}$P-labeled 740 AT #120 NotI insert. Other members of the *A. thaliana* ARF multigene family have been identified using programs of the University of Wisconsin Genetic Computer Group. The BAC clone T08I13 located on chromosome II has a high degree of homology to 740 AT #120 (78% to 86% identity at the nucleotide level).

chloroform, and the PCR product was directly cloned into the HincII site in Bluescript KS+ (Strategene). The plasmid map of KS+Nb ARF #3, which contains the *N. benthamiaca* ARE ORF in pBluescript KS+ is shown in FIG. 16. The nucleotide sequence of *N. benthamiana* KS+Nb ARF#3, which contains partial ADP-ribosylation factor ORF, was determined by dideoxynucleotide sequencing. The nucleotide sequence from KS+Nb ARF#3 had a strong similarity to other plant ADP-ribosylation factor sequences (82 to 87% identities at the nucleotide level). The nucleotide sequence comparison of *N. benthamiana* KS+Nb ARE#3 and *A. thaliana* 740 AT #120 shows a high homology between them (FIG. 17, SEQ ID NOs: 13and 14respectively). The nucleotide sequence of KS+NbARF #3 exhibits a high degree of homology (77-87% identities and positives) to plant, yeast and mammalian DNA encoding ARFs (Table 4). Again, the high homology of DNAs encoding GTP binding proteins from yeast, plants, human, bovine and mice indicates that DNAs from one donor organism can be transfected into another host organism and effectively silence the endogenous gene of the host organism.

TABLE 4

KS+ Nb ARF #3 Nucleotide sequence comparison

|  | Score | Expect | Identities | Positives |
|---|---|---|---|---|
| A. thaliana M95166 | 448.2 bits (1622) | 1.2e−129 | 366/418 (87%) | 366/418 (87%) |
| C. roseus AF005238 | 446.0 bits (1614) | 5.3e−129 | 368/427 (86%) | 370/427 (86%) |
| S. bakko AB003377 | 444.9 bits (1610) | 1.1e−128 | 366/421 (86%) | 366/421 (86%) |
| rice AF012896 | 425.8 bits (1541) | 5.1e−121 | 357/418 (85%) | 357/418 (85%) |
| V. unguiculata AF022389 | 425.8 bits (1541) | 5.1e−121 | 857/418 (85%) | 357/418 (85%) |
| barley E10542 | 413.4 bits (1496) | 1.2e−115 | 356/427 (83%) | 356/427 (83%) |
| S. tuberosum X74461 | 405.9 bits (1469) | 3.5e−115 | 353/427 (82%) | 353/427 (82%) |
| carrot D45420 | 408.4.4 bits (1478) | 3.3e−114 | 354/427 (82%) | 354/427 (82%) |
| corn X80042 | 400.1 bits (1448) | 2.3e−113 | 348/421 (82%) | 348/421 (82%) |
| rice D17760 | 403.4 bits (1460) | 3.7e−112 | 352/427 (82%) | 352/427 (82%) |
| C. reinhardtii U27120 | 373.6 bits (1352) | 5.0e−103 | 340/427 (79%) | 340/427 (79%) |
| Human ARF3 M33384 | 367.5.5 bits (1330) | 7.1e−101 | 334/419 (79%) | 334/419 (79%) |
| mouse brain ARF3 D87900 | 355.3 bits (1286) | 1.3e−97 | 330/421 (78%) | 330/421 (78%) |
| Bovine J03794 | 342.6 bits (1240) | 1.4e−95 | 324/419 (77%) | 324/419 (77%) |

Isolation and Characterization of a cDNA Encoding *Nicotiana benthamiana* ARF

A 488 bp cDNA from *N. benthamiana* stem cDNA library was isolated by polymerase chain reaction (PCR) using the following oligonucleotides: ATARFK15, 5' AAG AAG GAG ATG CGA ATT CTG ATG GT 3' (upstream) (SEQ ID NO:55), ATARFN176, 5' ATG TTG TTG GAG AGC CAG TCC AGA CC 3' (downstream) (SEQ ID NO: 56). The vent polymerase in the reaction was inactivated using phenol/

A full-length cDNA encoding ARF is isolated by screening the *N. benthamiana* cDNA library by colony hybridization using a $^{32}$P-labeled *N. benthamiana* KS+/Nb ARF #3 probe. Hybridization is carried out at 42° C. for 48 hours in 50% formamide, 5×SSC, 0.02 M phosphate buffer, 5× Denhart's solution, and 0.1 mg/ml sheared calf thymus DNA. Filters are washed at 65° C. in 0.1×SSC, 0.1% SDS prior to autoradiography.

Example 7

Transfecting *N. Benthamiana* Using pK20-2b-120(+)-RZ

The 740AT #120 *A. thaliana* ARF cDNA was cloned into the Not I site of plasmid pK20-2b-P/N-RZ in the positive orientation. The resulting construct, pK20-2b-120(+)-RZ (FIG. 18) was transcribed using T7 RNA polymerase (Ambion mMessage mMachine), mixed with TRV RNA-1 (pLSB-1) transcripts, and inoculated onto *N. benthamiana*.

After 7 days, plants transfected with pK20-2b-120(+)-RZ were severely stunted and induced severe necrosis in the systemic leaves.

Example 8

Genomic DNA Library Construction in a Recombinant Viral Nucleic Acid Vector

Genomic DNAs represented in BAC (bacterial artificial chromosome) or YAC (yeast artificial chromosome) libraries are obtained from the Arabidopsis Biological Resource Center (ABRC). The BAC/YAC DNAs are mechanically size-fractionated, ligated to adapters with cohesive ends, and shotgun-cloned into recombinant viral nucleic acid vectors. Alternatively, mechanically size-fractionated genomic DNAs are blunt-end ligated into a recombinant viral nucleic acid vector. Recovered colonies are prepared for plasmid minipreps with a Qiagen BioRobot 9600®. The plasmid DNA preps done on the BioRobot 9600® are assembled in 96-well format and yield transcription quality DNA. The recombinant viral nucleic acid/Arabidopsis genomic DNA library is analyzed by agarose gel electrophoresis (template quality control step) to identify clones with inserts. Clones with inserts are then transcribed in vitro and inoculated onto *N. benthamiana* or *Arabidopsis thaliana*. Selected leaf disks from transfected plants are then be taken for biochemical analysis.

Genomic DNA from Arabidopsis typically contains a gene every 2.5 kb (kilobases) on average. Genomic DNA fragments of 0.5 to 2.5 kb obtained by random shearing of DNA were shotgun assembled in a recombinant viral nucleic acid expression/knockout vector library. Given a genome size of Arabidopsis of approximately 120,000 kb, a random recombinant viral nucleic acid genomic DNA library would need to contain minimally 48,000 independent inserts of 2.5 kb in size to achieve 1× coverage of the Arabidopsis genome. Alternatively, a random recombinant viral nucleic acid genomic DNA library would need to contain minimally 240,000 independent inserts of 0.5 kb in size to achieve 1× coverage of the Arabidopsis genome. Assembling recombinant viral nucleic acid expression/knockout vector libraries from genomic DNA rather than cDNA has the potential to overcome known difficulties encountered when attempting to clone rare, low-abundance mRNA's in a cDNA library. A recombinant viral nucleic acid expression/knockout vector library made with genomic DNA would be especially useful as a gene silencing knockout library. In addition, the Dual Heterologous Subgenomic Promoter Expression System (DHSPES) expression/knockout vector library made with genomic DNA would be especially useful for expression of genes lacking introns. Furthermore, other plant species with moderate to small genomes (e.g. rose, approximately 80,000 kb) would be especially useful for recombinant viral nucleic acid expression/knockout vector libraries made with genomic DNA. A recombinant viral nucleic acid expression/knockout vector library can be made from existing BAC/YAC genomic DNA or from newly-prepared genomic DNAs for any plant species.

Example 9

Construction of a *Nicotiana benthamiana* NB08 cDNA Library

Vegetative *N. benthamiana* plants were harvested 3.3 weeks after sowing and sliced up into three groups of tissue: leaves, stems and roots. Each group of tissue was flash frozen in liquid nitrogen and total RNA was isolated from each group separately using the following hot borate method. Frozen tissue was ground to a fine powder with a pre-chilled mortar and pestle, and then further homogenized in a pre-chilled glass tissue grinder. Immediately thereafter, added 2.5 ml/g tissue hot (~82° C.) XT Buffer (0.2 M borate decahydrate, 30 mM EGTA, 1% (w/v) SDS, 1% (w/v) deoxycholate (sodium salt) was added. Adjusted pH to 9.0 with 5 N NaOH, treated with 0.1% DEPC and autoclaved. Before use, added 10 mM dithiothreitol, 15 Nonidet P-40 (NP-40) and 2% (w/v) polyvinylpyrrolidone, MW 40,000 (PVP-40)) was added to the ground tissue. The tissue was homogenized 1-2 minutes and quickly decanted to a pre-chilled Oak Ridge centrifuge tube containing 105 µl of 20 mg/ml proteinase K in DEPC treated water. The tissue grinder was rinsed with an additional 1 ml hot XT Buffer per g tissue, which was then added to rest of the homogenate. The homogenate was incubated at 42° C. at 100 rpm for 1.5 h. 2 M KCl was added to the homogenate to a final concentration of 160 mM, and the mixture was incubated on ice for 1 h to precipitate out proteins. The homogenate was centrifuged at 12,000×g for 20 min at 4° C., and the supernatant was filtered through sterile miracloth into a DEPC-treated 250 ml centrifuge tube. 8 M LiCl was added to a final concentration of 2 M LiCl and incubated on ice overnight. Precipitated RNA was collected by centrifugation at 12,000×g for 20 min at 4° C. The pellet was washed three times in 10-20 ml 4° C. 2 M LiCl. Each time the pellet was resuspended with a glass rod mM Tris-HCl (pH 7.5), and purified from insoluble cellular components by spinning at 12,000×g for 20 min at 4° C. The RNA containing supernatant was transferred to a 50 ml DEPC-treated Oak Ridge tube and precipitated overnight at −20° C. with 2.5 volumes of 100% ethanol. The RNA was pelleted by centrifugation at 9,800×g for 30 min at 4° C. The RNA pellet was washed in 1-2 ml cold 70° C. ethanol and centrifuged at 9,800×g for 5 min at 4° C. Residual ethanol was removed from the RNA pellet by drying at 37° C., and the RNA was resuspended in 1-2 mL DEPC treated dd-water and transferred to a 1.5 ml microfuge tube. The Oak Ridge tube was rinsed in 500 µl DEPC-treated dd-water, which was then added to the rest of the RNA. The RNA was quantitated by spectrophotometry and quality was assessed by gel electrophoresis. The RNA was then aliquoted into 2 mg aliquots and precipitatation was initiated with 1/10 volume of 3 M sodium acetate, pH 6.0 and 2.5 volumes of cold 100% ethanol. RNA was stored long-term at −80° C. and precipitated when needed. Precipitation was done by centrifuging for 30 min at 16,000×g, and the RNA pellet washed with cold 70% ethanol, and centrifuged for 5 min at 16,000× g. After drying the pellet under vacuum at 37° C., the RNA was resuspended in DEPC-treated water. This is the total RNA.

Messenger RNA was purified from total RNA using a MACS mRNA isolation kit (Miltenyi Biotec, Auburn Calif.), following the manufacturer's instructions. A reverse transcription reaction was used to synthesize cDNA from the mRNA template using the Gibco BRL cDNA synthesis and cloning kits (Gaithersburg, Md.). Resulting cDNAs were then digested with Sal I and Not I.

Example 10

Utility of TRV in Silencing Endogenous Plant Genes

To further assess the ability of TRV to silence endogenous plant genes, a cDNA library (NB08) from *N. benthamiana* seedlings was subcloned into the Xho I and Not I sites of pK20-2b-X/N-PmeI in the positive orientation. Resulting clones were transcribed and coinoculated with TRV RNA-1 transcripts onto individual *N. benthamiana* plants. Out of 384 clones inoculated, 125 (33%) produced a phenotype different from the TRV-2b-GFP control. These phenotypes ranged from stunting, chlorosis, necrosis, leaf distortion, or death of the plant. These 384 clones were sequenced and annotated by BLAST X and BLAST N analysis.

Several clones analyzed produced a phenotype that would be predicted if the corresponding endogenous gene was inhibited or silenced. For example, for a TRV RNA2 clone containing sequence homologous to α-tubulin induced severe shoot and root stunting, as expected since a-tubulin is involved in cell division in the meristematic tissue. Inhibition of α-tubulin with herbicides in the dinitroaniline family has been shown to also to result a similar phenotype in plants see Purdue University Cooperative Extension Work in Agriculture and Home Economics web page, Herbicide Mode-Of-Action Summary, Ross, et al.). An RNA-2 clone containing sequence homologous to uroporphyrinogen decarboxylase, an enzyme involved in porphyrin and chlorophyll metabolism, induced necrosis on infected leaves similar to that seen in a hypersensitive response in plants. It has been previously reported that expression of the antisense RNA for this enzyme resulted in the production of "necrotic leaf lesions" (Mock, et al. *J Biol. Chem.* 12:4231-8 (1999)).Collectively, these results strongly show the utility of TRV in silencing endogenous plant genes using homologous gene sequences. Information gained from studies in *N. benthamiana* could be extended and applied to identifying novel genes in *Arabidopsis*.

Example 11

GC/MS Analysis of a Sample from Infected Plants

A selected set of samples from infected plants was analyzed by gas chromatography/mass spectroscopy (GC/MS). Several clones produced a biochemical profile that would be predicted if the corresponding endogenous gene were inhibited or silenced. For example, for a TRV clone contained a homolog to putrescine N-methyltransferase, an enzyme in the nicotine biosynthesis pathway; GC/MS analysis showed that there w as an 8-fold decrease in nicotine levels in leaves of plants infected with this clone.

Example 12

Purification and Analysis of Metabolites from Transfected Plants

Leaf tissue was harvested in triplicate (30-40 mg) from transfected plants at 13 days post-inoculation, placed in 1.5 ml Eppendorf tubes, and dried in a Speedvac (SC210A, Savant) overnight. Controls used were uninoculated leaf tissue and tissue from TRV-2b-GFP infected plants. The controls for extraction were deuterium(d)-labeled internal standard compounds with 50 l water. Samples were stored at 4° C. until processed. Samples were quickly frozen in liquid nitrogen and crushed with a motorized plastic pestle in Eppendorf tubes. HPLC-grade methanol (300 l) containing internal standards (10 ng/l of nicotine-d3, phenol-d5, and pyridine-d5) was added and samples were further ground. Samples were then heated to 60° C. for 30 minutes. Samples were centrifuged for 10 minutes at 14,000 rpm at 4° C. Supernatant containing the methanol phase (200 l) was transferred to a microvial insert (0.25 ml conical glass with Ki. Western Analytical Products, Inc) and placed in a 2 ml GC vial (Agilent) and sealed with 11 mm silver crimp cap (Agilent) and stored at 4° C. until GC/MS analysis.

GC/MS analysis was carried out using a GC/MS system consisting of a Hewlett-Packard (HP) 7683 auto-sampler, a HP 6890 gas chromatograph, and a HP 5973 mass selective detector. Chromatography was performed using a 30 m ×0.25 μm DB-1701 column with a 0.25 μm film thickness (J&W Scientific, Folsom, Calif.). The temperatures for injection, interface, and ion source were 200° C., 250° C., and 230° C., respectively. Helium flow was 1.2 ml/min. Mass spectra were recorded from 35 to 700 amu at 2.24 scans/sec. Tuning was done according to the instrument manual using Tris(perfluorobutyl)amine as the reference compound.

Aliquots of 20 μl of the samples were injected into a pre-column separation injector (ProSep 800, Apex Technologies, Inc.). The ProSep was set at an initial GC split mode followed by a splitless mode at 0.02 minutes, and then a GC split mode after 2.0 minutes. The temperature for the pre-column was held at 200° C. for 1 minute, and then increased to 350° C. at 200° C./min, and held for 112 minutes. The column oven temperature was held for 5 minutes at 50° C., then increased at 2.5° C./min to 299° C., and held for 10 minutes. The total run time was 114 minutes.

A compound list (quantitation database) was generated using HP enhanced data analysis software from the library search report. The putative identity of each compound was made by comparison with the spectrum from the Wiley library. The quality of the identification and quantity of the integration of registered compound was examined. The spectrum from each sample was calculated against this compound list to yield the compound list and their amount. Approximately 415 compounds were identified. The integration accuracy was edited manually. The registered compounds were normalized against the internal controls and then averaged from triplicate samples. The compounds were then analyzed by ranking and clustering. Ranking involved calculating the ratio between the amount of each compound detected in TRV-infected samples and the control samples and ordering the ratios in increasing and decreasing order. Clustering was done by grouping compounds from TRV-infected samples according to their trend to increase or decrease when compared to the controls and deriving a phylogenetic tree linking all the compounds.

Example 13

Positive Sense Inhibition of EPSPS

Figure 19:
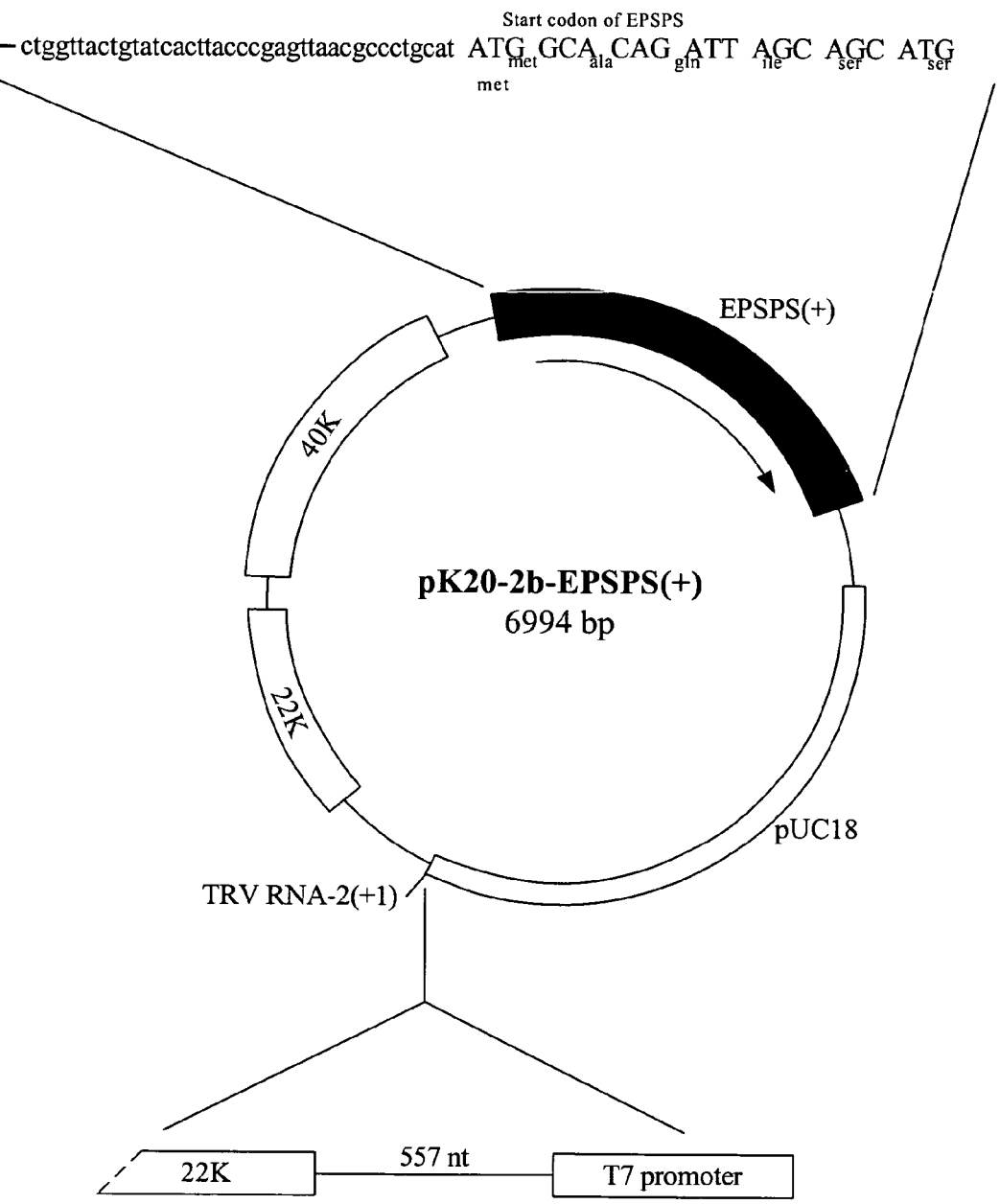
FIG. 19 depicts the plasmid pK20-2b-EPSP(+). (SEQ ID NOS: 15 and 16).

The 5-enolpyruvyl-shikimate-3 phosphate synthase (EPSPS) gene encodes an enzyme involved in the conversion of shikimic acid to chorismic acid and is the enzyme target of the herbicide Roundup®. The EPSPS gene from *N. tabacum* was PCR amplified from the plasmid 736.1 using the following oligonucleotides: 5'- TGGTTCTGCAG TTATGCATG-GCACAGATTAGCAGCATG-3' (upstream) (SEQ ID NO: 57) and 5'-GGTACCAAGCTTGCGGCCGCTTAATGCT- TGGAGTACTCCTG-3' (downstream) (SEO ID NO:58). This PCR product was subcloned into pK20-2b-P/N-SmaI in the positive orientation to result in the construct pK20-2b-EPSPS(+). (FIG. 19) When transcripts from pK20-2b-EPSPS (+) were coinoculated with pLSB-1 transcripts onto *N benthamiana*, chlorotic patches on the systemic leaves were observed after 10-14 days. Samples from infected plants were analyzed using GC/MS. GC/MS analysis revealed that there was a 47-fold increase in shikimic acid accumulation compared to the TRV-GFP control, as expected from a positive sense inhibition of the EPSPS enzyme and an accumulation of the enzyme substrate. Plants treated with Roundup ® showed a 69-fold increase in shikimic acid.

Example 14

Figure 20:
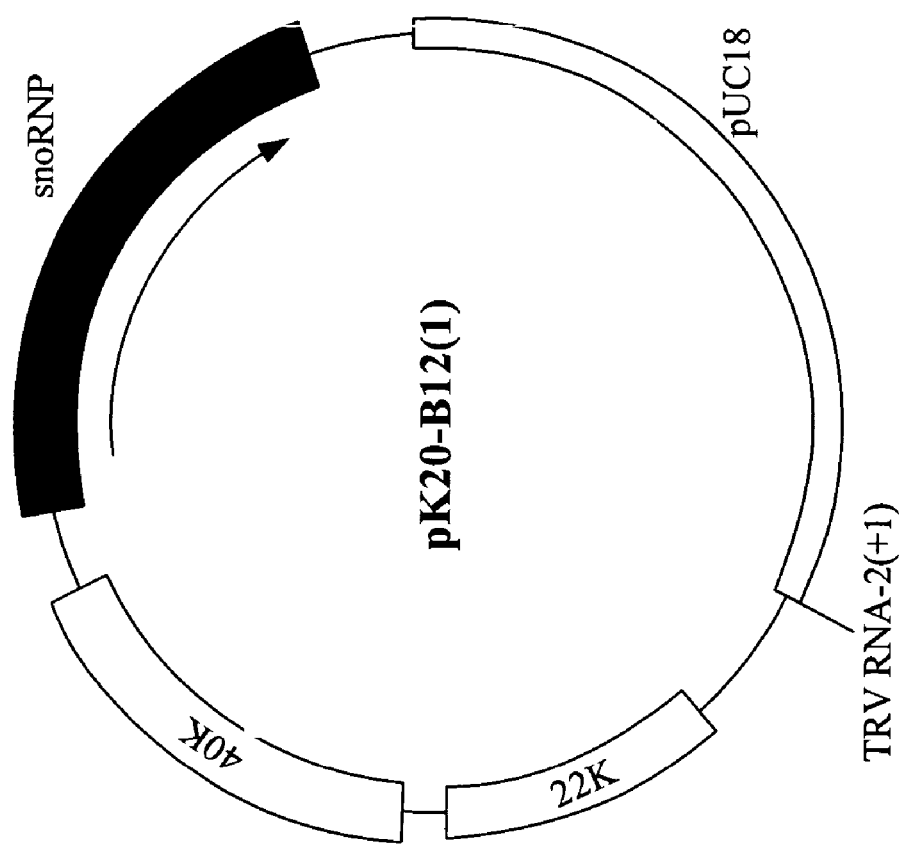
FIG. 20 depicts the plasmid pK20-B12(1).

Identification of a Nop10-Like Small Nucleolar Ribonucleoprotein Gene Involved in The Regulation of Plant Growth by Cytoplasmic Inhibition of Gene Expression Using Viral Derived RNA One to two weeks after inoculation, transfected *Nicotiana benthamiana* plants were visually monitored for changes in growth rates, morphology, and color. One set of plants transfected with pK20-B12 (FIG. 20) had an increase in stem circumference, distorted leaves and were severely stunted, DNA sequence analysis (FIG. 21, SEQ ID NO: 17) revealed that this clone contained a *Nicotiana benthamiana* Nop 10-like ribonucleoprotein open reading frame (ORF) in the positive orientation. The pK20-B12 encoded protein sequence exhibited a high degree of homology (62-68% and 76-78%, identities and positives, respectively) to yeast, insect and human Nop 10 small nucleolar ribonucleoproteins proteins (Table 5). The increase in stem circumference may be a desired trait for the forest industry.

TABLE 5 pK20-B12 Amino acid Sequence Comparison

| | Score | Expect | Identities | Positives |
|---|---|---|---|---|
| *A. thaliana* AC007109 | 103.5 bits (294) | 3.9e–25 | 56/64 (87%) | 59/64 (92%) |
| Drosophila AE003828 | 78.9 bits (224) | 1.0e–17 | 44/64 (68%) | 50/64 (78%) |
| Human AB043103 | 77.4 bits (220) | 2.7e–17 | 40/60 (66%) | 49/60 (81%) |
| *S. pombe* AL157917 | 74.3 bits (211) | 2.4e–16 | 40/64 (62%) | 49/64 (76%) |
| *S. cerevisiae* NP_058135.1 | 66.9 bits (190) | 4.5e–14 | 36/58 (62%) | 45/58 (77%) |

Example 15

Figure 22:
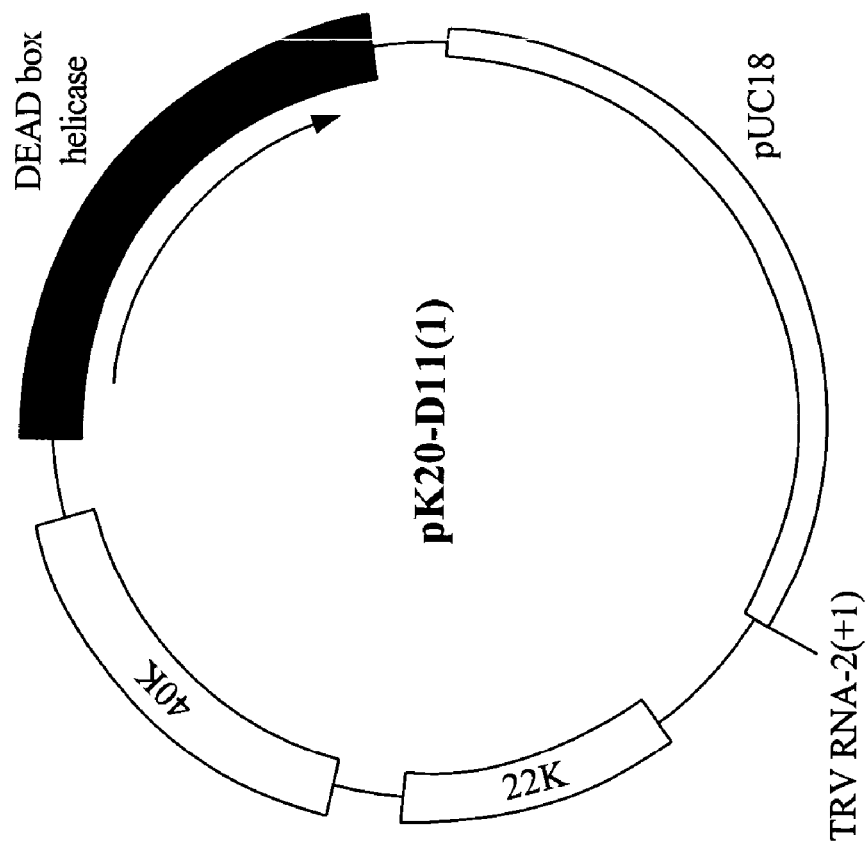
FIG. 22 depicts the plasmid pK20-D11(1)

Identification of a DEAD Box RNA Helicase Gene Involved in The Regulation of Plant Growth by Cytoplasmic Inhibition of Gene Expression Using Viral Derived RNA One to two weeks after inoculation, transfected *Nicotiana benthamiana* plants were visually monitored for changes in growth rates, morphology, and color. One set of plants transfected with pK20-D 11(1) (FIG. 22) were stunted and had necrotic leaves. DNA sequence analysis (FIG. 23, SEQ ID NO: 18) revealed that this clone contained a *Nicotiana benthamiana* DEAD box RNA helicase open reading frame (ORF) in the positive orientation. The pK20-D 11(1) encoded protein sequence exhibited a high degree of homology (70-74% and 82-85%, identities and positives, respectively) to yeast, insect and human DEAD box RNA helicase proteins (Table 6). The DEAD box RNA helicase family containing the highly conserved residues, Asp-Glu-Ala-Asp, are involved in diverse biological functions such as ribosome assembly, translation initiation, and RNA splicing. They modulate regulatory factors during organ maturation, cell growth and differentiation. Although the DEAD box RNA helicase family has been described in *Arabidopsis thaliana*, the actual function of the genes encoding "putative 20 computer-predicted helicases" has not been determined experimentally.

TABLE 6 pK20-D11(1) Amino acid sequence comparison

| | Score | Expect | Identities | Positives |
|---|---|---|---|---|
| *A. thaliana* AL360314 | 293.2 bits (833) | 4.5e–83 | 163/174 (93%) | 170/174 (97%) |
| *S. pombe* Z99162 | 241.1 bits (685) | 2.1e–67 | 130/175 (74%) | 149/175 (85%) |
| *S. cerevisiae* D89270 | 241.1 bits (685) | 2.7e–67 | 130/175 (74%) | 149/175 (85%) |
| Drosophila Q27268 | 224.2 bits (637) | 2.7e–62 | 123/175 (70%) | 144/175 (82%) |
| Human AK026614 | 221.8 bits (630) | 1.4e–61 | 121/172 (70%) | 144/172 (83%) |

Example 16

Figure 24:
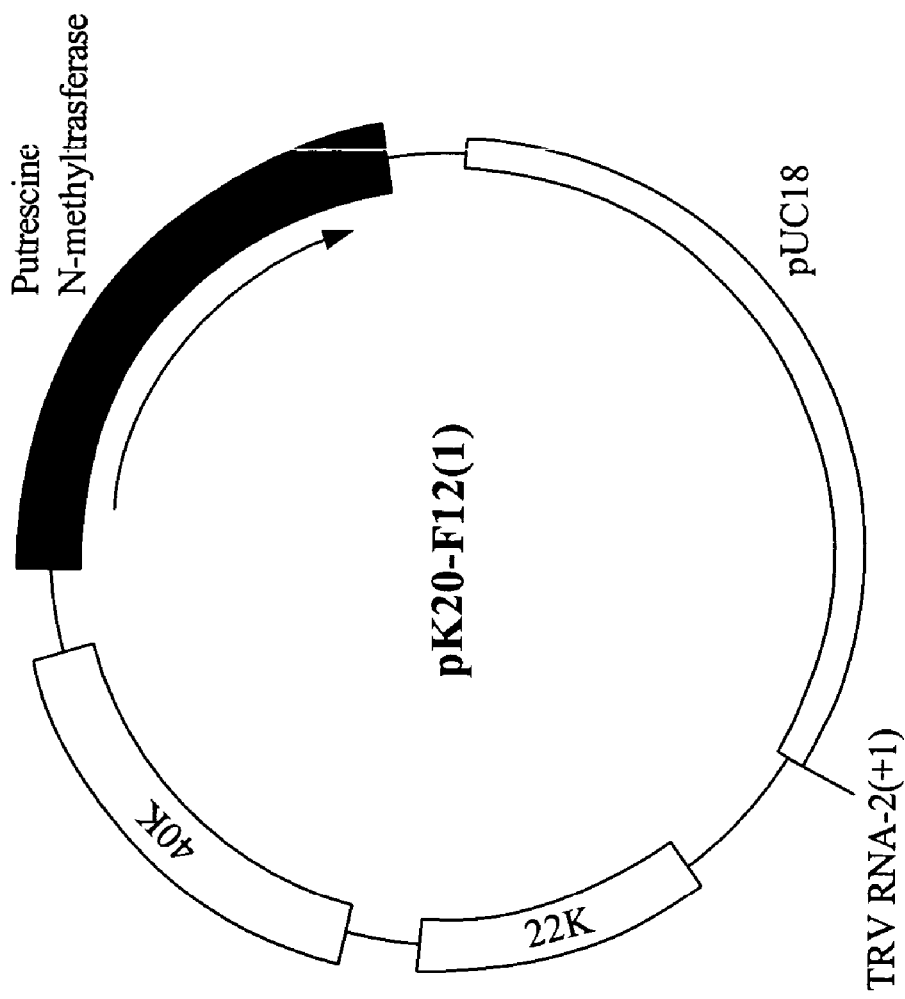
FIG. 24 depicts the plasmid pK20-F12(1).

Identification of a Putative Putrescine N-Methyltransferase Gene by Cytoplasmic Inhibition of Alkaloid Biosynthesis Using Viral Derived RNA One to two weeks after inoculation, transfected *Nicotiana benthamiana* plants were visually monitored for changes in growth rates, morphology, and color. One set of plants transfected with pK20-F12(1) (FIG. 24) had an 8-fold decrease in the accumulation of the alkaloid nicotine (when compared with TRV-2b-GFP control (11.5 ng nicotine/mg tissue and 97.5 ng/mg tissue, respectively). DNA sequence analysis (FIG. 25, SEQ ID NO: 19) revealed that this clone contained a *Nicotiana benthamiana* putrescine N-methyltransferase open reading frame (ORF) in the positive orientation. The pK20-F12(1) encoded protein sequence was compared to *N. tabacum* putrescine N-methyltransferase AF126809 (96% and 96%, identities and positives, respectively).

Example 17

Figure 26:
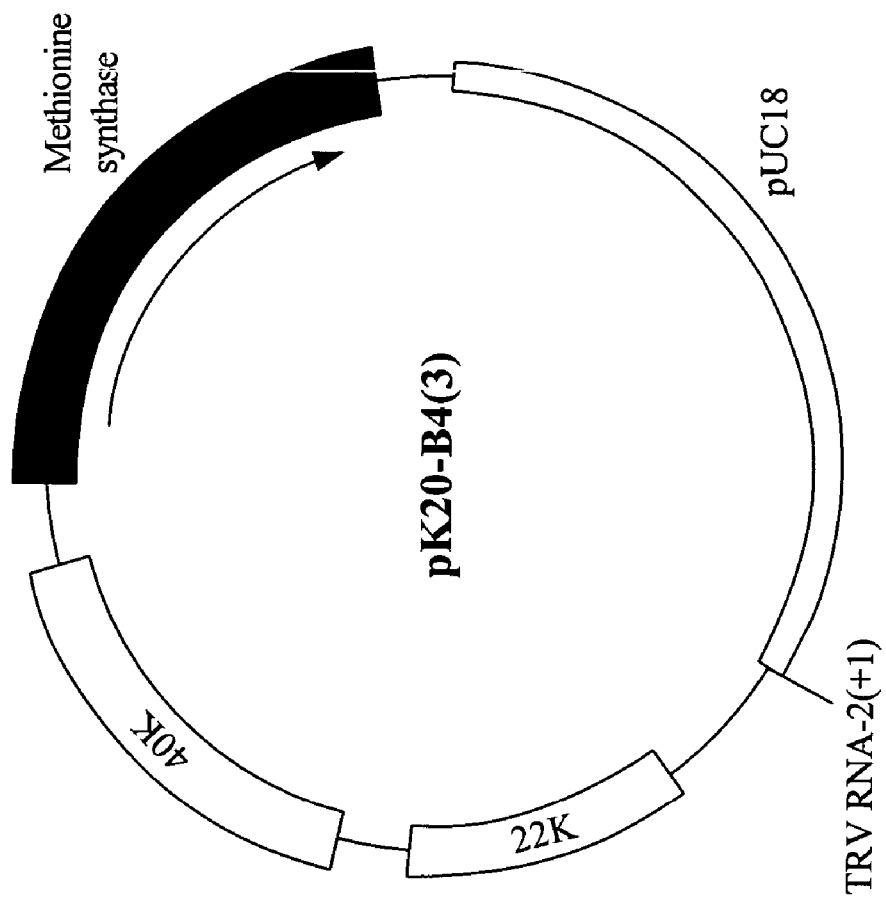
FIG. 26 depicts the plasmid pK20-B4(3).

Identification of a Methionine Synthase Gene Involved in the Regulation of Plant Growth by Cytoplasmic Inhibition of Gene Expression Using Viral Derived RNA One to two weeks after inoculation, transfected *Nicotiana benthamiana* plants were visually monitored for changes in growth rates, morphology, and color. One set of plants transfected with pK20-B4(3) (FIG. 26) were extremely stunted, had chlorotic and necrotic leaves, and had short spacing between the internodes. DNA sequence analysis (FIG. 27, SEQ ID NO: 20) revealed that this clone contained a *Nicotiana benthamiana* methionine synthase open reading frame (ORF) in a positive orientation. The pK20-B4(3) encoded protein sequence exhibited a high degree of homology (87-96% and 93-97%, identities and positives, respectively) to potato, coffee, periwinkle, *A. thaliana*, and common ice plant methionine synthase/—homocysteine S-methyltransferase proteins (Table 7).

TABLE 7 pK20-B4(3) Amino acid sequence comparison

|  | Score | Expect | Identities | Positives |
|---|---|---|---|---|
| S. tuberosum AF082893 | 258.4 bits (734) | 7.8e−73 | 140/145 (96%) | 142/145 (97%) |
| Coffea arabica AF220054 | 255.6 bits (726) | 1.9e−71 | 138/145 (95%) | 142/145 (97%) |
| periwinkle Q42699 | 251.7 bits (715) | 8.0e−71 | 136/145 (93%) | 141/145 (97%) |
| A. thaliana AB011480 | 243.9 bits (693) | 1.7e−68 | 131/145 (90%) | 139/145 (95%) |
| ice plant U84889 | 239.7 bits (681) | 3.2e−67 | 126/144 (87%) | 135/144 (93%) |

Example 18

Figure 28:
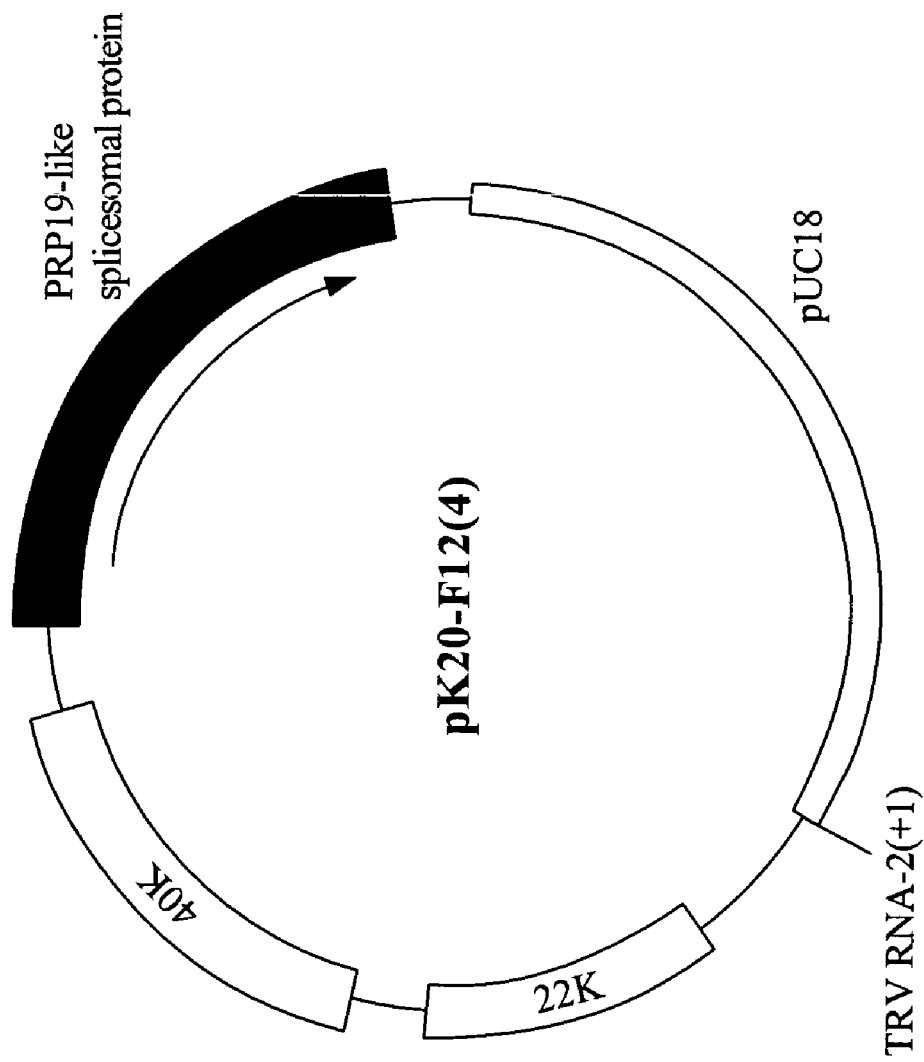
FIG. 28 depicts the plasmid pK20-F12(4).

Identification of a PRP19-like Spliceosomal Protein Gene Involved in the Regulation of Plant Growth by Cytoplasmic Inhibition of Gene Expression Using Viral Derived RNA One to two weeks after inoculation, transfected Nicotiana benthamiana plants were visually monitored for changes in growth rates, morphology, and color. One set of plants transfected with pK20-F12(4) (FIG. 28) were extremely stunted. DNA sequence analysis (FIG. 29, SEQ ID NO: 21) revealed that this clone contained a Nicotiana benthamiana PRP19-like spliceosomal protein open reading frame (ORF) in the positive orientation. The pK20-F12(4) encoded protein sequence had homology (33-71% and 55-86%, identities and positives, respectively) to A. thaliana, human nuclear matrix protein NMP200, rat and Drosophila proteins (Table 8).

TABLE 8 pK20-F12(4) Amino Acid Sequence Comparison

|  | Score | Expect | Identities | Positives |
|---|---|---|---|---|
| A. thaliana AC002332 | 180.9 bits (514) | 8.8e−68 | 98/138 (71%) | 119/138 (86%) |
| Human NMP200 AJ131186 | 120.7 bits (343) | 3.7e−31 | 83/216 (38%) | 122/216 (56%) |
| rat AB020022 | 120.7 bits (343) | 3.7e−31 | 83/216 (38%) | 122/216 (56%) |
| Drosophila AE003799 | 106.3 bits (302) | 2.0e−26 | 73/216 (33%) | 120/216 (55%) |

Example 19

Figure 30:
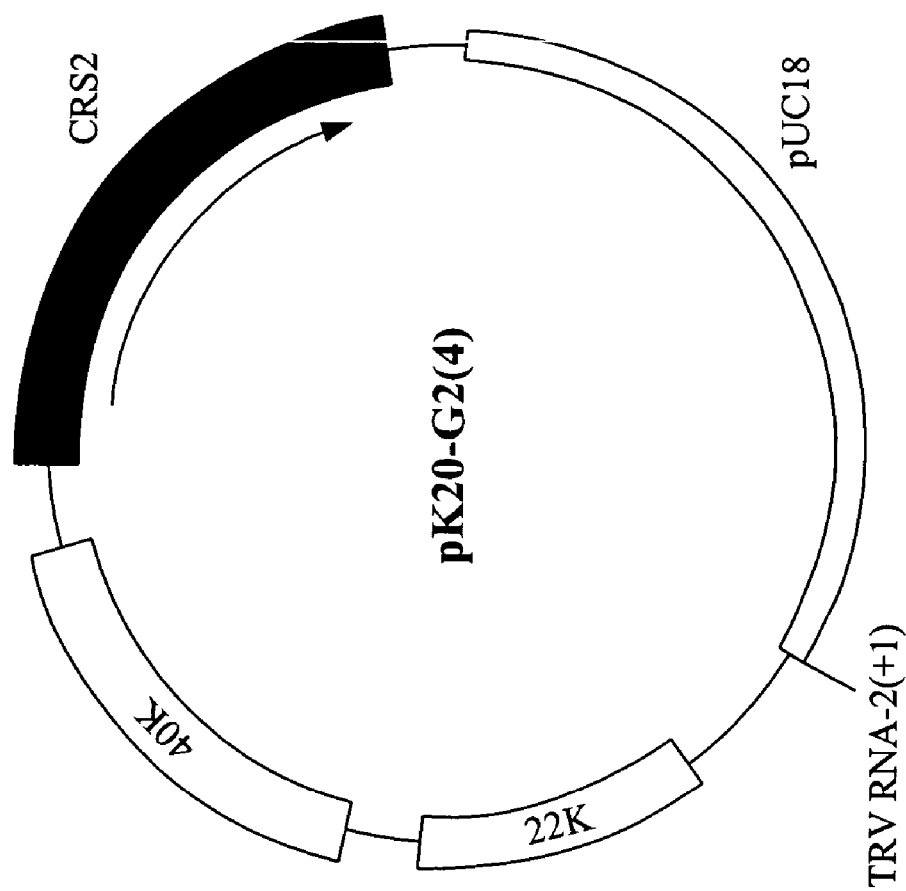
FIG. 30 depicts the plasmid pK20-G2(4).

Identification of a CRS2 Chloroplast Gene Involved in the Regulation of Plant Color by Cytoplasmic Inhibition of Gene Expression Using Viral Derived RNA One to two weeks after inoculation, transfected Nicotiana benthamiana plants were visually monitored for changes in growth rates, morphology, and color. One set of plants transfected with pK20-G2(4) (FIG. 30) developed white bleached leaves containing a slight yellow tinge. DNA sequence analysis (FIG. 31, SEQ ID NO: 22) revealed that this clone contained a Nicotiana benthamiana CRS2-like protein open reading frame (ORF) in the positive orientation. The CRS2 protein is involved in splicing the chloroplast group II introns. The pK20-G2(4) encoded protein sequence had homology (71-73% and 85-86%, identities and positives, respectively) to corn and A. thaliana CRS2 proteins (Table 9).

TABLE 9 pK20-G2(4) Amino Acid Sequence Comparison

|  | Score | Expect | Identities | Positives |
|---|---|---|---|---|
| Zea mays AF225708 | 293.9 bits (835) | 4.6e−83 | 149/208 (71%) | 180/208 (86%) |
| A. thaliana AL391148 | 288.7 bits (820) | 1.9e−81 | 151/206 (73%) | 178/206 (86%) |
| A. thaliana AB011481 | 287.6 bits (817) | 3.9e−81 | 147/202 (72%) | 173/202 (85%) |

Example 20

Multigene Silencing Using Both TRV RNA-1 And RNA-2

When one gene is silenced using TRV RNA-1 and one or more genes are silenced using RNA-2, many parts of a biochemical pathway can be affected, allowing for more complex pathway manipulation than silencing only one gene. When N. benthamiana plants are coinoculated with the RNA-1 construct pLSB-1 PDS(+) and the TRV RNA-2 construct pK20-2b-120(+)-RZ (from Example 7), a combination of phenotypes is expected: white leaf bleaching from PDS silencing and severe stunting and necrosis from 740AT #120 cDNA silencing. When N. benthamiana plants are coinoculated with the RNA-1 construct pLSB-1 PDS(+) and the TRV RNA-2 construct pK20-2b-EPSPS(+) (from Example 11), a combination of phenotypes is expected: white leaf bleaching from the PDS silencing along with chlorotic patches on the systemic leaves, and an increase in the accumulation of both phytoene and shikimic acid compared to the TRV-GFP control.

Example 21

Multigene Expression by Further Modification of TRV RNA-2

The native 2b subgenomic promoter (sgp) is used to drive the expression of one gene, while the heterologous PEBV sgp drives expression of another. GUS (beta-glucuronidase) is inserted into the 2b slot and GFP into the PEBV slot. When the resulting construct, pK20-GUS-GFP, is coinoculated with the RNA-1 construct pLSB-1 onto *N. benthamiana* plants, both GFP and GUS expression are expected simultaneously throughout the plant.

Example 22

Simultaneous Silencing by RNA-1 and Multigene Expression by RNA-2

When *N. benthamiana* plants are coinoculated with the RNA-1 construct pLSB-1 PDS (+) and the RNA-2 construct pK20-Gus-GFP, both GFP and Gus expression and PDS silencing are expected simultaneously throughout the plant.

Example 23

Multigene Expression by Further Modification of TRV RNA-2

The 2b sgp is used to drive the expression of one gene. the PEBV sgp is used to drive the expression of a second, and the original 2c sgp is used to drive the expression of a third gene. GUS is inserted into the 2b slot, GFP into the PEBV slot, and luciferase into the 2c slot. When the resulting construct, pK20-GUS-GFP-luciferase, is coinoculated with the RNA-1 construct pLSB-1 onto *N. benthamiana* plants, simultaneous expression of GFP, GUS, and luciferase is expected throughout the plant.

Example 24

Simultaneous Silencing by RNA-1 and Multigene Expression by RNA-2

After *N. benthamiana* plants are coinoculated with the RNA-1 construct pLSB-1 PDS (+) and the RNA-2 construct pK20-GUS-GFP-luciferase. simultaneous expressing of GFP, GUS and luciferase and silencing of PDS are expected throughout the plant.

Although the invention has been described with reference to the presently preferred embodiments, it should be understood that various modifications can be made without departing from the spirit of the invention.

What is claimed is:

1. A bipartite RNA viral vector, comprising:
   (a) a modified tobravirus RNA-1 comprising a first foreign RNA sequence, operably linked to 3'-end of the stop codon of the RNA sequence that codes for a cysteine-rich protein of RNA-1; and
   (b) a modified tobravirus RNA-2 comprising a promoter-gene construct, which comprises a subgenomic promoter operably linked to the 5' end of a second foreign RNA sequence, wherein said promoter-gene construct is inserted in place of the 2C gene.

2. The viral RNA vector according to claim 1, wherein said first or said second foreign RNA is either a complete open reading frame or a partial open reading frame.

3. The viral RNA vector according to claim 1, wherein said first or said second foreign RNA is in either a positive sense or an antisense orientation.

4. The RNA viral vector according to claim 2, wherein said first or said second foreign RNA codes for part of a protein.

5. The RNA viral vector according to claim 4, wherein said vector is a silencing vector.

6. The RNA viral vector according to claim 2, wherein said second foreign RNA codes for a protein.

7. The RNA viral vector according to claim 6, wherein said vector is a silencing vector or an expression vector.

8. The RNA viral vector according to claim 1, wherein said first or said second foreign RNA sequence is obtained from any member of a library of RNA sequences taken from a eukaryotic or prokaryotic species.

9. The viral RNA vector according to claim 2, wherein said first or said second foreign RNA encodes for all or part of putrescine N-methyltransferase.

10. A method of expressing one or more foreign gene in a plant host, comprising:
    infecting a plant host with the RNA viral vector of claim 1, whereby said second foreign gene is expressed in the plant host.

11. The method according to claim 10, furthering comprising allowing the viral vector to infect the plant systemically.

12. A method of silencing one or more plant host genes, comprising:
    infecting a plant host with the RNA viral vector of claim 1, whereby the expression of said first or said second foreign RNA sequence causes silencing of an endogenous plant host gene.

13. The method according to claim 12, furthering comprising allowing the viral vector to infect the plant systemically.

14. A method of simultaneously silencing a plant host gene and expressing a foreign gene, comprising:
    infecting a host with the bipartite RNA viral vector of claim 1, whereby the first foreign RNA sequence causes silencing of an endogenous gene of a plant host, and the second foreign RNA is expressed in the plant host.

15. The method according to claim 14, further comprising allowing the viral vector to infect the plant systemically.

16. A plant host infected by a viral RNA vector according to claim 1.

17. A method of changing the phenotype or biochemistry of a plant host, comprising:
    (a) infecting a plant host with the RNA viral vector of claim 1,
    (b) expressing transiently said foreign RNA sequence in said plant host; and
    (c) changing one or more phenotypic or biochemical characteristics in said plant host.

* * * * *

```
                         SEQUENCE LISTING

<160> NUMBER OF SEQ ID NOS: 58

<210> SEQ ID NO 1
<211> LENGTH: 6791
<212> TYPE: DNA
<213> ORGANISM: Tobravirus

<400> SEQUENCE: 1
ataaaacatt tcaatccttt gaacgcggta gaacgtgcta attggatttt ggtgagaacg      60
cggtagaacg tacttatcac ctacagtttt attttgtttt tcttttttggt ttaatctatc    120 cagcttagta ccgagtgggg gaaagtgact ggtgtgccta aaaccttttc tttgatactt    180
tgtaaaaata catacagata caatggcgaa cggtaacttc aagttgtctc aattgctcaa    240
tgtggacgag atgtctgctg agcagaggag tcatttctttt gacttgatgc tgactaaacc    300
tgattgtgag atcgggcaaa tgatgcaaag agttgttgtt gataaagtcg atgacatgat    360
tagagaaaga aagactaaag atccagtgat tgttcatgaa gttctttctc agaaggaaca    420
gaacaagttg atggaaattt atcctgaatt caatatcgtg tttaaagacg acaaaaacat    480
ggttcatggg tttgcggctg ctgagcgaaa actacaagct ttattgcttt tagatagagt    540
tcctgctctg caagaggtgg atgacatcgg tggtcaatgg tcgttttggg taactagagg    600
tgagaaaagg attcattcct gttgtccaaa tctagatatt cgggatgatc agagagaaat    660
ttctcgacag atatttctta ctgctattgg tgatcaagct agaagtggta agagacagat    720
gtcggagaat gagctgtgga tgtatgacca atttcgtgaa aatattgctg cgcctaacgc    780
ggttaggtgc aataatacat atcagggttg tacatgtagg ggttttttctg atggtaagaa    840 gaaaggcgcg cagtatgcga tagctcttca cagcctgtat gacttcaagt tgaaagactt    900
gatggctact atggttgaga agaaaactaa agtggttcat gctgctatgc ttttttgctcc    960
```

```
tgaaagtatg ttagtggacg aaggtccatt accttctgtt gacggttact acatgaagaa    1020
gaacgggaag atctatttcg gttttgagaa agatccttcc ttttcttaca ttcatgactg    1080
ggaagagtac aagaagtatc tactggggaa gccagtgagt taccaagggg atgtgttcta    1140
cttcgaaccg tggcaggtga gaggagacac aatgcttttt tcgatctaca ggatagctgg    1200
agttccgagg aggtctctat catcgcaaga gtactaccga agaatatata tcagtagatg    1260
ggaaaacatg gttgttgtcc caattttcga tctggtcgaa tcaacgcgag agttggtcaa    1320
gaaagacctg tttgtagaga aacaattcat ggacaagtgt ttggattaca tagctaggtt    1380
atctgaccag cagctgacca taagcaatgt taaatcatac ttgagttcaa ataattgggt    1440
cttattcata aacggggcgg ccgtgaagaa caagcaaagt gtagattctc gagatttaca    1500
gttgttggct caaactttgc tagtgaagga caagtggcg agacctgtca tgagggagtt     1560
gcgtgaagca attctgactg agacgaaacc tatcacgtca ttgactgatg tgctgggttt    1620
aatatcaaga aaactgtgga agcagtttgc taacaagatc gcagtcggcg gattcgttgg    1680
catggttggt actctaattg gattctatcc aaagaaggta ctaacctggg cgaaggacac    1740
accaaatggt ccagaactat gttacgaaga ctcgcacaaa accaaggtga tagtatttct    1800
gagtgttgtg tatgccattg gaggaatcac gcttatgcgt cgagacatcc gagatggact    1860
ggtgaaaaaa ctatgtgata tgtttgatat caaacggggg gcccatgtct tagacgttga    1920
gaatccgtgc cgctattatg aaatcaacga tttctttagc agtctgtatt cggcatctga    1980
gtccggtgag accgttttac cagatttatc cgaggtaaaa gccaagtctg ataagctatt    2040
gcagcagaag aaagaaatcg ctgacgagtt tctaagtgca aaattctcta actattctgg    2100
cagttcggtg agaacttctc caccatcggt ggtcggttca tctcgaagcg gactgggtct    2160
gttgttggaa gacagtaacg tgctgaccca agctagagtt ggagtttcaa gaaaggtaga    2220
cgatgaggag atcatggagc agtttctgag tggtcttatt gacactgaag cagaaattga    2280
cgaggttgtt tcagcctttt cagctgaatg tgaaagaggg gaaacaagcg gtacaaaggt    2340
gttgtgtaaa cctttaacgc caccaggatt tgagaacgtg ttgccagctg tcaaaccttt    2400
ggtcagcaaa ggaaaaacgg tcaaacgtgt cgattacttc caagtgatgg gaggtgagag    2460
attaccaaaa aggccggttg tcagtggaga cgattctgtg gacgctagaa gagagtttct    2520
gtactactta gatgcggaga gagtcgctca aaatgatgaa attatgtctc tgtatcgtga    2580
ctattcgaga ggagttattc gaactggagg tcagaattac ccgcacggac tgggagtgtg    2640
ggatgtggag atgaagaact ggtgcatacg tccagtggtc actgaacatg cttatgtgtt    2700
ccaaccagac aaacgtatgg atgattggtc gggatactta aagtggctg tttgggaacg     2760 aggtatgttg gtcaacgact tcgcggtcga aggatgagt gattatgtca tagttttgcga    2820 tcagacgtat cttttgcaata acaggttgat cttggacaat ttaagtgccc tggatctagg    2880
accagttaac tgttctttg aattagttga cggtgtacct ggttgtggta agtcgacaat     2940
gattgtcaac tcagctaatc cttgtgtcga tgtggttctc tctactggga gcagcaac     3000 cgacgacttg atcgagagat cgcgagcaa aggttttcca tgcaaattga aaaggagagt     3060
gaagacggtt gattctttt tgatgcattg tgtcgatggt tctttaaccg gagacgtgtt     3120
gcatttcgac gaagctctca tggcccatgc tggtatggtg acttttgcg ctcagatagc     3180 tggtgctaaa cgatgtatct gtcaaggaga tcagaatcaa atttctttca agcctagggt    3240
atctcaagtt gatttgaggt tttctagtct ggtcggaaag tttgacattg ttacagaaaa    3300
aagagaaact tacagaagtc cagcagatgt ggctgccgta ttgaacaagt actatactgg    3360
```

```
agatgtcaga acacataacg cgactgctaa ttcgatgacg gtgaggaaga ttgtgtctaa     3420
agaacaggtt tctttgaagc ccggtgctca gtacataact ttccttcagt ctgagaagaa     3480
ggagttggta aatttgttgg cattgaggaa agtggcagct aaagtgagta cagtacacga     3540
gtcgcaagga gagacattca aagatgtagt cctagtcagg acgaaaccta cggatgactc     3600
aatcgctaga ggtcgggagt acttaatcgt ggcgttgtcg cgtcacacac aatcacttgt     3660
gtatgaaact gtgaaagagg acgatgtaag caaagagatc agggaaagtg ccgcgcttac     3720
gaaggcggct ttggcaagat tttttgttac tgagaccgtc ttatgacggt ttcggtctag     3780
gtttgatgtc tttagacatc atgaagggcc ttgcgccgtt ccagattcag gtacgattac     3840
ggacttggag atgtggtacg acgctttgtt tccgggaaat tcgttaagag actcaagcct     3900
agacgggtat ttggtggcaa cgactgattg caatttgcga ttagacaatg ttacgatcaa     3960
aagtggaaac tggaaagaca gtttgctga aaagaaacg tttctgaaac cggttattcg     4020
tactgctatg cctgacaaaa ggaagactac tcagttggag agtttgttag cattgcagaa     4080
aaggaaccaa gcggcacccg atctacaaga aaatgtgcac gcgacagttc taatcgaaga     4140
gacgatgaag aagctgaaat ctgttgtcta cgatgtggga aaaattcggg ctgatcctat     4200
tgtcaataga gctcaaatgg agagatggtg gagaaatcaa agcacagcgg tacaggctaa     4260
ggtagtagca gatgtgagag agttacatga aatagactat tcgtcttaca tgtatatgat     4320
caaatctgac gtgaaaccta agactgattt aacaccgcaa tttgaatact cagctctaca     4380
gactgttgtg tatcacgaga agttgatcaa ctcgttgttc ggtccaattt tcaaagaaat     4440
taatgaacgc aagttggatg ctatgcaacc acattttgtg ttcaacacga gaatgacatc     4500
gagtgattta aacgatcgag tgaagttctt aaatacggaa gcggcttacg actttgttga     4560
gatagacatg tctaaattcg acaagtcggc aaatcgcttc catttacaac tgcagctgga     4620
gatttacagg ttatttgggc tggatgagtg ggcggccttc ctttgggagg tgtcgcacac     4680
tcaaactact gtgagagata ttcaaaatgg tatgatggcg catatttggt accaacaaaa     4740
gagtggagat gctgatactt ataatgcaaa ttcagataga acactgtgtg cgctcttgtc     4800
tgaattacca ttggagaaag cagtcatggt tacatatgga ggagatgact cactgattgc     4860
gtttcctaga ggaacgcagt ttgttgatcc gtgtccaaag ttggctacta agtgaatt     4920 cgagtgcaag attttaagt acgatgtccc aatgttttgt gggaagttct tgcttaagac     4980
gtcatcgtgt tacagttcg tgccagatcc ggtaaaagtt ctgacgaagt tggggaaaaa     5040
gagtataaag gatgtgcaac atttggccga gatctacatc tcgctgaatg attccaatag     5100
agctcttggg aactacatgg tggtatccaa actgtccgag tctgtttcag accggtattt     5160
gtacaaaggt gattctgttc atgcgctttg tgcgctatgg aagcatatta agagttttac     5220
agctctgtgt acattattcc gagacgaaaa cgataaggaa ttgaacccgg ctaaggttga     5280
ttggaagaag gcacagagag ctgtgtcaaa cttttacgac tggtaatatg aagacaagt     5340 cattggtcac cttgaagaag aagactttcg aagtctcaaa attctcaaat ctaggggcca     5400
ttgaattgtt tgtggacggt aggaggaaga gaccgaagta ttttcacaga agaagagaaa     5460
ctgtcctaaa tcatgttggt gggaagaaga gtgaacacaa gttagacgtt tttgaccaaa     5520
gggattacaa aatgattaaa tcttacgcgt ttctaaagat agtaggtgta caactagttg     5580
taacatcaca tctacctgca gatacgcctg ggttcattca aatcgatctg ttggattcga     5640
gacttactga gaaaagaaag agaggaaaga ctattcagag attcaaagct cgagcttgcg     5700
```

```
ataactgttc agttgcgcag tacaaggttg aatacagtat ttccacacag gagaacgtac    5760
ttgatgtctg gaaggtgggt tgtatttctg agggcgttcc ggtctgtgac ggtacatacc    5820
ctttcagtat cgaagtgtcg ctaatatggg ttgctactga ttcgactagg cgcctcaatg    5880
tggaagaact gaacagttcg gattacattg aaggcgattt taccgatcaa gaggttttcg    5940
gtgagttcat gtctttgaaa caagtggaga tgaagacgat tgaggcgaag tacgatggtc    6000
cttacagacc agctactact agacctaagt cattattgtc aagtgaagat gttaagagag    6060
cgtctaataa gaaaaactcg tcttaatgca taaagaaatt tattgtcaat atgacgtgtg    6120
tactcaaggg ttgtgtgaat gaagtcactg ttcttggtca cgagcgtgt agtatcggtc     6180 atgctaacaa attgcgaaag caagttgctg acatggttgg tgtcacacgt aggtgtgcgg    6240
aaaataattg tggatggttt gtctgtgttg ttatcaatga ttttactttt gatgtgtata    6300
attgttgtgg ccgtagtcac cttgaaaagt gtcgtaaacg tgttgaaaca agaaatcgag    6360
aaatttggaa acaaattcga cgaaatcaag ctgaaaacat gtctgcgaca gctaaaaagt    6420
ctcataattc gaagacctct aagaagaaat tcaaagagga cagagaattt gggacaccaa    6480
aaagattttt aagagatgat gttcctttcg ggattgatcg tttgtttgct ttttgatttt    6540 atttatatt gttatctgtt tctgtgtata gactgtttga gattggcgct tggccgactc     6600
attgtcttac catagggaa cggactttgt ttgtgttgtt attttatttg tattttatta     6660
aaattctcaa tgatctgaaa aggcctcgag gctaagagat tattgggggg tgagtaagta    6720
cttttaaagt gatgatggtt acaaaggcaa aaggggtaaa acccctcgcc tacgtaagcg    6780
ttattacgcc c                                                         6791

<210> SEQ ID NO 2
<211> LENGTH: 133
<212> TYPE: DNA
<213> ORGANISM: Pea Early Browning Virus

<400> SEQUENCE: 2
ataattatac tgatttgtct ctcgttgata gagtctatca ttctgttact aaaaatttga    60
caactcggtt tgctgaccta ctggttactg tatcacttac ccgagttaac gccctgcagg    120
atatcgcggc cgc                                                       133

<210> SEQ ID NO 3
<211> LENGTH: 133
<212> TYPE: DNA
<213> ORGANISM: Pea Early Browning Virus

<400> SEQUENCE: 3
ataattatac tgatttgtct ctcgttgata gagtctatca ttctgttact aaaaatttg     60 caactcggtt tgctgaccta ctggttactg tatcactt acc cga gtt aac gcc ct    116 ca gctcgaggcg ccgc                                                   133

<210> SEQ ID NO 4
<211> LENGTH: 138
<212> TYPE: DNA
<213> ORGANISM: Pea Early Browning Virus
<220> FEATURE:
<221> NAME/KEY: CDS
<222> LOCATION: (118)...(138)

<400> SEQUENCE: 4
ataattatac tgattgtctc tcgttgatag agtctatcat tctgttacta aaaatttgac    60
```

-continued

```
aactcggttt gctgacctac tggttactgt atcacttacc gagttaacgc cctgcag atg    120
                                                                Met
                                                                1 ccc caa att gga ctt gtt                                                138
Pro Gln Ile Gly Leu Val
        5
```

<210> SEQ ID NO 5
<211> LENGTH: 7
<212> TYPE: PRT
<213> ORGANISM: Pea Early Browning Virus

<400> SEQUENCE: 5

Met Pro Gln Ile Gly Leu Val
1               5

<210> SEQ ID NO 6
<211> LENGTH: 61
<212> TYPE: DNA
<213> ORGANISM: Nicotiana benthamiana

<400> SEQUENCE: 6

```
tttgctttt gattaattaa cctgcagggc cggcgcggcc gctagctttt atattgttat    60
c                                                                   61
```

<210> SEQ ID NO 7
<211> LENGTH: 48
<212> TYPE: DNA
<213> ORGANISM: Nicotiana benthamiana
<220> FEATURE:
<221> NAME/KEY: CDS
<222> LOCATION: (28)...(48)

<400> SEQUENCE: 7

```
tttgcttttt gattaattaa cctgcat atg ccc caa att gga ctt gtt           48
                            Met Pro Gln Ile Gly Leu Val
                            1               5
```

<210> SEQ ID NO 8
<211> LENGTH: 7
<212> TYPE: PRT
<213> ORGANISM: Nicotiana benthamiana

<400> SEQUENCE: 8

Met Pro Gln Ile Gly Leu Val
1               5

<210> SEQ ID NO 9
<211> LENGTH: 400
<212> TYPE: DNA
<213> ORGANISM: Arabidopsis thaliana

<400> SEQUENCE: 9

```
tccgaaacat tcttcgtagt gaagcaaaat ggggttgagt ttcgccaagc tgtttagcag    60
gcttttgcc aagaaggaga tgcgaattct gatggttggt cttgatgctg ctggtaagac   120
cacaatcttg tacaagctca agctcggaga gattgtcacc accatccta ctattggttt   180
caatgtggaa actgtggaat acaagaacat tagtttcacc gtgtgggatg tcggggtca   240
ggacaagatc cgtcccttgt ggagacacta cttccagaac actcaaggtc taatctttgt   300
tgttgatagc aatgacagag acagagttgt tgaggctcga gatgaactcc acaggatgct   360
gaatgaggac gagctgcgtg atgctgtgtt gcttgtgttt                          400
```

<210> SEQ ID NO 10
<211> LENGTH: 400
<212> TYPE: DNA
<213> ORGANISM: Arabidopsis thaliana
<220> FEATURE:
<221> NAME/KEY: misc_feature
<222> LOCATION: (1)...(400)
<223> OTHER INFORMATION: n = A,T,C or G

<400> SEQUENCE: 10

| | | | | | |
|---|---|---|---|---|---|
| tccgaaacat | tcttcgtagt | gaagcaaaat | ggggttgagt | ttcgccaagc | tgtttagcag | 60 |
| gctttttgcc | aagaaggaga | tgcgaattct | gatggttggt | cttgatgctg | ctggtaagac | 120 |
| cacaatcttg | tacaagctca | agctcggaga | gattgtcacc | accatcccta | ctattggttt | 180 |
| caatgtggaa | actgtggaat | acaagaacat | tagtttcacc | gtgtgggatg | tcggggtca | 240 |
| ggacaagatc | cgtcccttgt | ggagacacta | cttccagaac | actcaaggtc | taatctttgt | 300 |
| tgttgatagc | aatgacagag | acagagttgt | tgaggctcga | gatgaactcc | acaggatgct | 360 |
| gnatgagnac | gagctgcgtg | atgctgtgtt | gcttgtgttt | | | 400 |

<210> SEQ ID NO 11
<211> LENGTH: 550
<212> TYPE: DNA
<213> ORGANISM: Arabidopsis thaliana

<400> SEQUENCE: 11

| | | | | | |
|---|---|---|---|---|---|
| aaatggggtt | gagtttcgcc | aagctgttta | gcaggctttt | tgccaagaag | gagatgcgaa | 60 |
| ttctgatggt | tggtcttgat | gctgctggta | agaccacaat | cttgtacaag | ctcaagctcg | 120 |
| gagagattgt | caccaccatc | cctactattg | gtttcaatgt | ggaaactgtg | aatacaaga | 180 |
| acattagttt | caccgtgtgg | gatgtcgggg | gtcaggacaa | gatccgtccc | ttgtggagac | 240 |
| actacttcca | gaacactcaa | ggtctaatct | ttgttgttga | tagcaatgac | agagacagag | 300 |
| ttgttgaggc | tcgagatgaa | ctccacagga | tgctgaatga | ggacgagctg | cgtgatgctg | 360 |
| tgttgcttgt | gtttgccaac | aagcaagatc | ttccaaatgc | tatgaacgct | gctgaaatca | 420 |
| cagataagct | tggccttcac | tccctccgtc | agcgtcattg | gtatatccag | agcacatgtg | 480 |
| ccacttcagg | tgaagggctt | tatgaaggtc | tggactggct | ctccaacaac | atcgctggca | 540 |
| aggcatgatg | | | | | | 550 |

<210> SEQ ID NO 12
<211> LENGTH: 550
<212> TYPE: DNA
<213> ORGANISM: Oryza sativa

<400> SEQUENCE: 12

| | | | | | |
|---|---|---|---|---|---|
| agatggggct | cacgttcacg | aagctgttca | gccgcctctt | cgccaagaag | gagatgagga | 60 |
| tcctcatggt | cggtctcgat | gcggccggta | aaaccaccat | cctctacaag | ctcaagctcg | 120 |
| gcgagatcgt | caccactatc | cccaccatcg | gttttaatgt | cgaaactgtt | gagtacaaga | 180 |
| acattagctt | caccgtttgg | gatgttggtg | gtcaggacaa | gatcaggccc | ctgtggaggc | 240 |
| actatttcca | gaacacccag | ggcctcattt | ttgttgtgga | cagcaatgac | agagagcgtg | 300 |
| ttgttgaggc | cagggatgag | ctccaccgta | tgctgaatga | ggatgagcta | cgtgatgctg | 360 |
| tgctgctggt | gtttgcaaac | aaacaagatc | ttcctaatgc | catgaacgct | gctgagatca | 420 |
| ccgacaagct | tggtctgcac | tccttgcgcc | agcggcactg | gtacatccag | agcacatgtg | 480 |

```
ctacctctgg tgaggggttg tatgaggggc ttgactggct ttccaacaac attgccaaca    540
aggcttgaag                                                          550

<210> SEQ ID NO 13
<211> LENGTH: 389
<212> TYPE: DNA
<213> ORGANISM: Arabidopsis thaliana

<400> SEQUENCE: 13
tggtcttgat gctgctggta agaccacaat cttgtacaag ctcaagctcg gagagattgt     60
caccaccatc cctactattg gtttcaatgt ggaaactgtg gaatacaaga acattagttt    120
caccgtggga tgtcgggggt caggacaaga tccgtccctt gtggagacac tacttccaga    180
acactcaagg tctaatcttt gttgttgata gcaatgacag agacagagtt gttgaggctc    240
gagatgaact ccacaggatg ctgaatgagg acgagctgcg tgatgctgtg ttgcttgtgt    300
ttgccaacaa gcaagatctt ccaaatgcta tgaacgctgc tgaaatcaca gataagcttg    360
gccttcactc cctccgtcag cgtcattgg                                     389

<210> SEQ ID NO 14
<211> LENGTH: 391
<212> TYPE: DNA
<213> ORGANISM: Nicotiana benthamiana

<400> SEQUENCE: 14
cggtcttgat gcagctggta aaaccaccat attgtacaag ctcaagctgg gagagatagt     60
taccactatt cctaccattg gattcaatgt ggagactgtt gaatacaaga acataagctt    120
cacggtctgg gatgttggtg gtcaggacaa gatccgacca ttgtggaggc attacttcca    180
aaacacacaa ggacttatct tgtggtcga tagtaatgat cgtgatcgtg ttgttgaggc    240
tagagatgag ctgcaccgga tgttaatga ggatgaactg agggatgctg tgctgcttgt    300
gtttgctaac aagcaagatc ttccaaatgc tatgaatgct gctgagatta ctgacaagct    360
tggtcttcat tctctccgtc aacgtcactg g                                  391

<210> SEQ ID NO 15
<211> LENGTH: 140
<212> TYPE: DNA
<213> ORGANISM: Pea Early Browning Virus
<220> FEATURE:
<221> NAME/KEY: CDS
<222> LOCATION: (120)...(140)

<400> SEQUENCE: 15
ataattatac tgatttgtct ctcgttgata gagtctatca ttctgttact aaaaatttga     60
caactcggtt tgctgaccta ctggttactg tatcacttac ccgagttaac gccctgcat    119 atg gca cag att agc agc atg                                         140
Met Ala Gln Ile Ser Ser Met
  1               5

<210> SEQ ID NO 16
<211> LENGTH: 7
<212> TYPE: PRT
<213> ORGANISM: Pea Early Browning Virus

<400> SEQUENCE: 16

Met Ala Gln Ile Ser Ser Met
  1               5
```

<210> SEQ ID NO 17
<211> LENGTH: 360
<212> TYPE: DNA
<213> ORGANISM: Nicotiana benthamiana

<400> SEQUENCE: 17

| | | | | | |
|---|---|---|---|---|---|
| gaaaccggcg | aagcagctca | ggtcacaatt | tagcgaggat | gtatctccag | ttttacatca | 60 |
| atgagaatgg | tgacaaagtt | tacaccacta | agaaagagtc | accactgggt | ttggccacag | 120 |
| aatccgctca | cccagcccgc | ttttcccccg | atgataaata | ttcaaggcaa | agagtgcttc | 180 |
| tgaagaagcg | atttggtttg | cttccaaccc | aaaagccacc | tcaaaagtac | taaaagtttt | 240 |
| tgctattgtg | tattgctttc | tactcatggt | tattatgttt | ctctgtcttg | tcgttgttga | 300 |
| cgtgactctt | gtattgcaac | tcaaattgca | tggcagcaat | tcaaacctca | tatctaattg | 360 |

<210> SEQ ID NO 18
<211> LENGTH: 667
<212> TYPE: DNA
<213> ORGANISM: Nicotiana benthamiana

<400> SEQUENCE: 18

| | | | | | |
|---|---|---|---|---|---|
| gcccacgcgt | ccgatgaggc | caagttgacc | cttcatggac | ttgtacagca | ctacattaaa | 60 |
| ttgagtgaaa | ccgagaaaaa | ccggaaacta | atgatctgc | tggacgcctt | aaacttcaac | 120 |
| caagttgtta | tatttgtcaa | gagtgtaagt | cgggcagcac | agctggataa | attactagtg | 180 |
| gagtgtaatt | ttccatctat | ctgcatccac | tctggcatga | tcttgtcgca | actgatctgg | 240 |
| ttggtagggg | cattgacatc | gaaagggtca | acattgttat | taactatgac | atgccagatt | 300 |
| ctgcagacac | gtatcttcac | agagtgggtc | gagctggtag | gtttggaact | aaaggccttg | 360 |
| ccatcacatt | tgtgtcatct | gcatcagatt | ctgatgttct | aaatcaggtt | caagaaaggt | 420 |
| ttgaagtaga | cataaaagag | cttcctgagc | agattgatac | ttctacgtac | atgccatctt | 480 |
| agcgatctcg | agagcttcca | gcaatatcaa | gtcatttaaa | agatggggggg | aactgacagg | 540 |
| tgttttgcta | ttgttgttaa | tttgaagaat | tggggggctc | ctactatatg | ctcttgcact | 600 |
| gctgagctgc | tgtaccccttg | ttgaactact | ctttctcctc | cagtttaaga | ggagcaccta | 660 |
| agaaatg | | | | | 667 |

<210> SEQ ID NO 19
<211> LENGTH: 331
<212> TYPE: DNA
<213> ORGANISM: Nicotiana benthamiana

<400> SEQUENCE: 19

| | | | | | |
|---|---|---|---|---|---|
| ggtcaaatcc | aaattagcac | ctctcaagtt | ctacaactct | gatattcaca | aagcaccatt | 60 |
| cattttgcca | tctttcgcca | gaagtatgat | cgagtcttta | tcaagtgaat | aatgaacact | 120 |
| ggtggtacaa | tcattggacc | aagatcgagt | ctttatcaag | tgaataaata | aagtgaaatg | 180 |
| caacgcattg | tatgaatcca | gtagtaatta | tcataattcg | gattcaccaa | ttagtgtaaa | 240 |
| ttcttctctgt | ggtgtttggt | tttttcatat | aaattttctt | gctgttgttt | tgatatgacg | 300 |
| tttcaactca | atccacgcaa | atcatttcat | t | | | 331 |

<210> SEQ ID NO 20
<211> LENGTH: 649
<212> TYPE: DNA
<213> ORGANISM: Nicotiana benthamiana

<400> SEQUENCE: 20

```
ggcctttttac ttgaactggg ctgtccactc cttcagaatc accaacgtcg gcattcaaga      60
caccacccag atccacacac acatgtgcta ctccaacttc aatgacatta tccactctat     120
cattgacatg gatgctgatg tgatcacaat tgagaactca cggtccgatg agaagctcct     180
ctcagttttc agggagggag ttaagtatgg tgctggaatt ggccccggtg tctatgatat     240
ccactcccct agaataccat caacggaaga gattgctgac agagttaaca agatgcttgc     300
tgttcttgac accaacatct tgtgggtcaa cccagattgt ggtctcaaga ctcgcaagta     360
cgctgaggta aagccagccc tcgagaacat ggtttctgct gccaaggcca tccgcaccca     420
acttgccagc accaagtgag tcagatgaag gagtcgcgac atatcaagat tcccttttc      480 atgaaacaga aaattctatg ttgatttta atcattgtgt tggcaacaaa tattgttgtg      540
taggttagct ctgcccgctg gcatttttct tcttgtgttt gagccatttc cttttcggaa     600
gaaaatatat ccaatgtatt atgatgtttt atgggtcgat tttggttac                 649
```

<210> SEQ ID NO 21
<211> LENGTH: 727
<212> TYPE: DNA
<213> ORGANISM: Nicotiana benthamiana

<400> SEQUENCE: 21

```
ggatgtgttg atcaatggga aaagagctgc tgaggacgag gagatgggtc ctgatggcaa      60
gaaaattcgc cctggaatat caaactctgt cattgagact cttacggaat gtaatgctgc     120
tctttcacag caaaggaaaa gacgacagat accggcaaca ctggcctctg tggatgctct     180
ggaaagatat acccaactga atagttatcc tcttcacaaa accaacaaac ctggtatttt     240
gtctttggat attcattatc ctaaggactt aattgctact ggtggtgttg attcaaatgc     300
tgtggtcttt gatcgtcctt caggacaaat catatcaaca ctaactggtc atttaaagag     360
ggttaccagt gtaaaatttg cgtctgaggg tgaactagtg gtctctggct cagcagataa     420
gacagttcgt ttgtggcaaa gttctgaaaa tgggaactat gactgtaggc atgtcttgaa     480
agatcataca gcagaggtgc aagctgtcac tgtccatgca accaataact attttgtgac     540
tgcttctctt gatagcacat ggtgctttta tgatcttgct tctggcttat gccttgcaca     600
ggtggcagat gctacagaat ctgagggtta cacatccgca agctttccca ccctgattgg     660
tcttgatcct tgggaacagg gacctcaggg tctctggttc agatttttggg attgtaaaaa     720 gtccagg                                                              727
```

<210> SEQ ID NO 22
<211> LENGTH: 720
<212> TYPE: DNA
<213> ORGANISM: Nicotiana benthamiana
<220> FEATURE:
<221> NAME/KEY: misc_feature
<222> LOCATION: (57)...(57)
<223> OTHER INFORMATION: n = A, T, C OR G

<400> SEQUENCE: 22

```
gctcccagag cctaatgggg ttaagtttga gtacactcct tggttaattg tcggatnggg      60
aaatcccggt aacaagtatc atgggactcg ccacaatgtt ggttttgaaa tgattgatcg     120
agtttctcaa gaggagggaa tcgtattaaa cacaatacag tcaaaggctt tgataggaat     180
aggttcgata ggggaggtac ctgtggtatt ggcaaagcct caagcctaca tgaatttcag     240
tggagaatcg gtcggaccac ttgctgcata ttatcaggtg cctctgcgtc acatccttct     300
ggtttatgat gagatgagct taccaaatgg tgttctgagg cttcagccta aaggaggaca     360
```

```
tggccagcat aatggggtga aaagtgtgat ggagcatttg gattgtcgca gggaatttcc        420
ccgattttgc ataggcatag gaaatccacc tggaactatg gacatgaagg catatcttct        480
acagaaattc agtgatacag agcggaagca ggtggatgca gcacttaatc aaggagttga        540
tgctgtcagg acgtagtat tggaaggctt tggtagtaaa atttcacgat ttaatatagg         600
acagaaatac aagtatcaca aagtttgatg aaattgaatc taaaatgaag gtgtaaaaga        660
gcacgaagat ttactgataa cttcaagtct aaaaattaag ggtgtaaaaa gaccccaagg        720

<210> SEQ ID NO 23
<211> LENGTH: 61
<212> TYPE: DNA
<213> ORGANISM: Nicotiana benthamiana.

<400> SEQUENCE: 23
ttaattaagc atgcggatcc cgtacgggcg taataacgct tacgtaggcg aggggttta         60 c                                                                        61

<210> SEQ ID NO 24
<211> LENGTH: 57
<212> TYPE: DNA
<213> ORGANISM: Nicotiana benthamiana

<400> SEQUENCE: 24
atgaagagca tgctaatacg actcactata gataaaacat ttcaatcctt tgaacgc           57

<210> SEQ ID NO 25
<211> LENGTH: 39
<212> TYPE: DNA
<213> ORGANISM: Nicotiana benthamiana

<400> SEQUENCE: 25
ttcatctgga tcccgggcgt aataacgctt acgtaggcg                               39

<210> SEQ ID NO 26
<211> LENGTH: 24
<212> TYPE: DNA
<213> ORGANISM: Pea Early Browning Virus

<400> SEQUENCE: 26
gtcctaatcc ctagggattt aagg                                               24

<210> SEQ ID NO 27
<211> LENGTH: 19
<212> TYPE: DNA
<213> ORGANISM: Pea Early Browning Virus

<400> SEQUENCE: 27
ctttggaaat tgcagaaac                                                     19

<210> SEQ ID NO 28
<211> LENGTH: 19
<212> TYPE: DNA
<213> ORGANISM: Pea Early Browning Virus

<400> SEQUENCE: 28
gtttctgcaa tttccaaag                                                     19

<210> SEQ ID NO 29
<211> LENGTH: 44
<212> TYPE: DNA
```

-continued

<213> ORGANISM: Pea Early Browning Virus

<400> SEQUENCE: 29
gaattcgggg taccgcggcc gcgatatcct gcagggcgtt aact 44

<210> SEQ ID NO 30
<211> LENGTH: 45
<212> TYPE: DNA
<213> ORGANISM: Pea Early Browning Virus

<400> SEQUENCE: 30
gaattcggta ccctgcagga tatcgcggcc gcggcgttaa ctcgg 45

<210> SEQ ID NO 31
<211> LENGTH: 27
<212> TYPE: DNA
<213> ORGANISM: Pea Early Browning Virus

<400> SEQUENCE: 31
aaggaaaaaa gcggccgcgg taccccg 27

<210> SEQ ID NO 32
<211> LENGTH: 42
<212> TYPE: DNA
<213> ORGANISM: Pea Early Browning Virus

<400> SEQUENCE: 32
cggatccccc gggtttaaac gggcgtaata acgcttacgt ag 42

<210> SEQ ID NO 33
<211> LENGTH: 35
<212> TYPE: DNA
<213> ORGANISM: Pea Early Browning Virus

<400> SEQUENCE: 33
aaactgcagc tcgagctgat ttaacaaatt ttaac 35

<210> SEQ ID NO 34
<211> LENGTH: 42
<212> TYPE: DNA
<213> ORGANISM: Pea Early Browning Virus

<400> SEQUENCE: 34
ttttcctttt gcggccgcgc acgtgtcagt cctgctcctc gg 42

<210> SEQ ID NO 35
<211> LENGTH: 27
<212> TYPE: DNA
<213> ORGANISM: Pea Early Browning Virus

<400> SEQUENCE: 35
aaggaaaaaa gcggccgcgg taccccg 27

<210> SEQ ID NO 36
<211> LENGTH: 83
<212> TYPE: DNA
<213> ORGANISM: Pea Early Browning Virus

<400> SEQUENCE: 36
gtttaaaccc gggcccgttt cgtcctcacg gactcatcag cccggaaaac acatccgggg 60
acgggcgtaa taacgttacg tag 83

```
<210> SEQ ID NO 37
<211> LENGTH: 36
<212> TYPE: DNA
<213> ORGANISM: Nicotiana benthamiana

<400> SEQUENCE: 37
tggttctgca gttatgcatg ccccaaattg gacttg                          36

<210> SEQ ID NO 38
<211> LENGTH: 37
<212> TYPE: DNA
<213> ORGANISM: Nicotiana benthamiana

<400> SEQUENCE: 38
ttttcctttt gcggccgcta aactacgctt gcttctg                         37

<210> SEQ ID NO 39
<211> LENGTH: 37
<212> TYPE: DNA
<213> ORGANISM: Nicotiana benthamiana

<400> SEQUENCE: 39
cgataacctg caggatgccc caaattggac ttgtttc                         37

<210> SEQ ID NO 40
<211> LENGTH: 38
<212> TYPE: DNA
<213> ORGANISM: Nicotiana benthamiana

<400> SEQUENCE: 40
tgtgtaatgg cggccgcaat atgtgcaacc cagtctcg                        38

<210> SEQ ID NO 41
<211> LENGTH: 38
<212> TYPE: DNA
<213> ORGANISM: Nicotiana benthamiana

<400> SEQUENCE: 41
cgataacctg caggacagaa aactgaagaa cacatctg                        38

<210> SEQ ID NO 42
<211> LENGTH: 38
<212> TYPE: DNA
<213> ORGANISM: Nicotiana benthamiana

<400> SEQUENCE: 42
tgtgtaatgg cggccgccta aactacgctt gcttctgc                        38

<210> SEQ ID NO 43
<211> LENGTH: 24
<212> TYPE: DNA
<213> ORGANISM: Nicotiana benthamiana

<400> SEQUENCE: 43
aagttcttgc ttaagacgtc atcg                                       24

<210> SEQ ID NO 44
<211> LENGTH: 47
<212> TYPE: DNA
<213> ORGANISM: Nicotiana benthamiana

<400> SEQUENCE: 44
gccggccctg caggttaatt aatcaaaaag caaacaaacg atcaatc               47
```

<210> SEQ ID NO 45
<211> LENGTH: 62
<212> TYPE: DNA
<213> ORGANISM: Nicotiana benthamiana

<400> SEQUENCE: 45
ttaattaacc tgcagggccg gcgcggccgc tagcttttat tttatattgt tatctgtttc    60
tg                                                                  62

<210> SEQ ID NO 46
<211> LENGTH: 22
<212> TYPE: DNA
<213> ORGANISM: Nicotiana benthamiana

<400> SEQUENCE: 46
cggataacaa tttcacacag ga                                            22

<210> SEQ ID NO 47
<211> LENGTH: 24
<212> TYPE: DNA
<213> ORGANISM: Nicotiana benthamiana

<400> SEQUENCE: 47
aagttcttgc ttaagacgtc atcg                                          24

<210> SEQ ID NO 48
<211> LENGTH: 22
<212> TYPE: DNA
<213> ORGANISM: Nicotiana benthamiana

<400> SEQUENCE: 48
cggataacaa tttcacacag ga                                            22

<210> SEQ ID NO 49
<211> LENGTH: 36
<212> TYPE: DNA
<213> ORGANISM: Nicotiana benthamiana

<400> SEQUENCE: 49
tggttctgca gttatgcatg ccccaaattg gacttg                             36

<210> SEQ ID NO 50
<211> LENGTH: 37
<212> TYPE: DNA
<213> ORGANISM: Nicotiana benthamiana

<400> SEQUENCE: 50
ttttcctttt gcggccgcta aactacgctt gcttctg                            37

<210> SEQ ID NO 51
<211> LENGTH: 14
<212> TYPE: DNA
<213> ORGANISM: Nicotiana benthamiana

<400> SEQUENCE: 51
tcgagcggcc gcat                                                     14

<210> SEQ ID NO 52
<211> LENGTH: 773
<212> TYPE: DNA
<213> ORGANISM: Arabidopsis thaliana

<400> SEQUENCE: 52

```
ccgaaacatt cttcgtagtg aagcaaaatg gggttgagtt tcgccaagct gtttagcagg      60 cttttttgcca agaaggagat gcgaattctg atggttggtc ttgatgctgc tggtaagacc    120
acaatcttgt acaagctcaa gctcggagag attgtcacca ccatccctac tattggtttc    180
aatgtggaaa ctgtggaata caagaacatt agtttcaccg tgtgggatgt cgggggtcag    240
gacaagatcc gtcccttgtg agacactact tccagaacac tcaaggtcta atctttgttg    300
ttgatagcaa tgacagagac agagttgttg aggctcgaga tgaactccac aggatgctga    360
atgaggacga gctgcgtgat gctgtgttgc ttgtgtttgc caacaagcaa gatcttccaa    420
atgctatgaa cgctgctgaa atcacagata agcttggcct tcactccctc cgtcagcgtc    480
attggtatat ccagagcaca tgtgccactt caggtgaagg gctttatgaa ggtctggact    540
ggctctccaa caacatcgct ggcaaggcat gatgagggag aaattgcgtt gcatcgagat    600
gattctgtct gctgtgttgg gatctctctc tgtcttgatg caagagagat tataaatatt    660
atctgaacct ttttgctttt tgggtatgtg aatgtttct tattgtgcaa gtagatggtc    720
ttgtacctaa aaatttacta gaagaaccct tttaaatagc tttcgtgtat tgt            773
```

```
<210> SEQ ID NO 53
<211> LENGTH: 8
<212> TYPE: PRT
<213> ORGANISM: Arabidopsis thaliana

<400> SEQUENCE: 53

Gly Leu Asp Ala Ala Gly Lys Thr
1               5

<210> SEQ ID NO 54
<211> LENGTH: 5
<212> TYPE: PRT
<213> ORGANISM: Arabidopsis thaliana

<400> SEQUENCE: 54

Asp Val Gly Gly Gln
1               5

<210> SEQ ID NO 55
<211> LENGTH: 26
<212> TYPE: DNA
<213> ORGANISM: Nicotiana benthamiana

<400> SEQUENCE: 55
aagaaggaga tgcgaattct gatggt                                           26

<210> SEQ ID NO 56
<211> LENGTH: 26
<212> TYPE: DNA
<213> ORGANISM: Nicotiana benthamiana

<400> SEQUENCE: 56
atgttgttgg agagccagtc cagacc                                           26

<210> SEQ ID NO 57
<211> LENGTH: 38
<212> TYPE: DNA
<213> ORGANISM: N. tabacum

<400> SEQUENCE: 57
tggttctgca gttatgcatg gcacagatta gcagcatg                              38
```

```
<210> SEQ ID NO 58
<211> LENGTH: 41
<212> TYPE: DNA
<213> ORGANISM: N. tabacum

<400> SEQUENCE: 58
ggtaccaagc ttgcggccgc ttaatgcttg gagtactcct g                    41
```